United States Patent
Nandabalan et al.

(10) Patent No.: US 6,573,364 B1
(45) Date of Patent: Jun. 3, 2003

(54) ISOLATION AND CHARACTERIZATION OF HERMANSKY PUDLAK SYNDROME (HPS) PROTEIN COMPLEXES AND HPS PROTEIN-INTERACTING PROTEINS

(75) Inventors: Krishnan Nandabalan, Guilford, CT (US); Meijia Yang, East Lyme, CT (US)

(73) Assignee: Curagen Corporation, New Haven, CT (US)

( * ) Notice: Subject to any disclaimer, the term of this patent is extended or adjusted under 35 U.S.C. 154(b) by 0 days.

(21) Appl. No.: 09/266,225

(22) Filed: Mar. 10, 1999

(51) Int. Cl.[7] .................. C07K 14/47; A61K 38/17; C12N 5/00
(52) U.S. Cl. .................. 530/350; 514/2; 435/317.1
(58) Field of Search ............... 520/350, 827; 514/2; 435/317.1

(56) References Cited

U.S. PATENT DOCUMENTS 5,283,173 A    2/1994  Fields et al. .................... 435/6

FOREIGN PATENT DOCUMENTS

DE   198 18 619 A 1   10/1999
WO   WO 98/46757      10/1998

OTHER PUBLICATIONS

Chamberlain, L. H., D. Roth, et al. (1995). "Distinct effects of alpha–SNAP, 14–3–3 proteins, and calmodulin on priming and triggering of regulated exocytosis." *J Cell Biol* 130(5): 1063–70.

Data, K. V., G. Dreyfuss, et al. (1993). "The human hnRNP M proteins: identification of a methionine/arginine– rich repeat motif in ribonucleoproteins." *Nucleic Acids Res* 21(3): 439–46.

Lee and e. al. (1995). *Biochem. Biophys. Res. Commun.* 213(2): 715–724.

Lu and e. al. (1998). *Gene* 213: 125–132.

Spritz, R. A. (1998). "Genetic defects in Chediak–Higashi syndrome and the beige mouse." *J. Clin Immunol* 18(2): 97–105.

Swank, R. T., E. K. Novak, et al. (1998). "Mouse models of Hermansky Pudlak syndrome: a review." *Pigment Cell Res* 11(2): 60–80.

Tang, W., Y. H. Lai, et al. (1997). "Murine Hn1 on chromosome 11 is expressed in hemopoietic and brain tissues." *Mamm Genome* 8(9); 695–6.

Aitken et al. (1995). "14–3–3 proteins on the MAP." *Trends Biochem Sci* 20(3): 95–7.

Banik et al. (1997). "Interaction of phosphorylated tryptophan hydroxylase with 14–3–3 proteins." *J Biol Chem* 272(42): 26219–25.

Chien et al. (1991). "The two–hybrid system: a method to identify and clone genes for proteins that interact with a protein of interest." *Proc Natl Acad Sci U S A* 88(21): 9578–82.

Gardner et al. (1997). "The mouse pale ear (ep) mutation is the homologue of human Hermansky–Pudlak syndrome." *Proc Natl Acad Sci U S A* 94(17): 9238–43.

Gong et al. (1996). "A transcription map of the DiGeorge and velo–cardio–facial syndrome minimal critical region on 22q11." *Hum Mol Genet* 5(6): 789–800.

Harmon et al. (1994). "Pathogenesis of pulmonary fibrosis: platelet–derived growth factor precedes structural alterations in the Hermansky–Pudlak syndrome." *J Lab Clin Med* 123(4): 617–27.

Ichimura–Ohshima et al. (1992). "cDNA cloning and chromosome assignment of the gene for human 14–3–3 protein eta chain." *J. Neurosci. Res* 31: 600–605.

Kao et al. (1994 "Cloning and expression of cyclosporin A– and FK506–sensitive nuclear factr of activated T–cells: NF45 and NF90.". *J. Biol. Chem.* 269: 20691–20699.

Komada et al. (1995). "Growth factor–induced tyrosine phosphorylation of Hrs, a novel 115– kilodalton protein with a structurally conserved putative zinc finger domain." *Mol Cell Biol* 15(11): 6213–21.

Margolis et al. (1996). "DRPLA gene (atrophin–1) sequence and mRNA expression in human brain." *Brain Res Mol Brain Res* 36(2): 219–26.

Morgan et al. (1992). "Ex01 and Exo2 proteins stimulate calcium–dependent exocytosis in permeabilized adrenal chromaffin cells." *Nature* 355(6363): 833–6.

Oh et al. (1996). "Positional cloning of a gene for Hermansky–Pudlak syndrome, a disorder of cytoplasmic organelles." *Nat. Genet.* 14: 300–306.

Okabe et al. (1992). "Calmodulin is involved in catecholamine secretion from digitonin– permeabilized bovine adrenal medullary chromaffin cells." *Biochem Biophys Res Commun* 186(2): 1006–11.

(List continued on next page.)

*Primary Examiner*—Gabrielle Bugaisky
(74) *Attorney, Agent, or Firm*—Mintz Levin; Ivor R. Elrifi; Cynthia A. Kozakiewicz

(57) ABSTRACT

The present invention relates to complexes of the HPS protein with proteins identified as interacting with HPS protein by a modified yeast two hybrid assay system. The proteins identified to interact with HPS protein are 14-3-3 protein, Hrs, atrophin-1, DGS-I, nuclear factor NF90, HPIP1 and human HN1 homolog protein. Accordingly, the present invention discloses complexes of HPS protein and 14-3-3 protein, Hrs, atrophin-1, DGS-I, nuclear factor NF90, HPIP1 and human HN1 homolog protein, and derivatives, fragments and analogs thereof. Additionally, the present invention also discloses nucleic acids encoding the HPIP1 and human HN1 homolog protein, or derivatives, fragments and analogs thereof. Methods of screening the complexes or proteins for efficacy in treating and/or preventing certain diseases and disorders, particularly atopic diseases, autoimmune diseases, neurodegenerative disease, cancer, pigmentation disorders, platelet dysfunction and viral diseases, are also disclosed herein.

31 Claims, 3 Drawing Sheets

OTHER PUBLICATIONS

Roth et al. (1995). "Stimulation of catecholamine secretion from adrenal chromaffin cells by 14–3–3 proteins is due to reorganization of the cortical actin network." *FEBS Letters* 374: 77–81.

Shimkets et al (1999) "Gene expression analysis by transcript profiling coupled to a gene database query." *Nat. Biotech.* 17:796–803.

NCI–CGAP: *National Cancer Institute, Cancer Genome Anatomy Project (GDAP), Tumor Gene Index*, Oct. 1, 1998; EMBL Database Entry AI51537.

Oh, J., et al: *The Hermansky–Pudlak syndrome (HPS) protein is part of a high molecular weight complex involved in biogenesis of early melanosomes*, 2000 Human Molecular Genetics 9: 375–385.

Sugano S., et al. *Homo sapiens cDNA FLJ20530 fis, clone KAT10776*, Feb. 22, 2000; EMBL Database Entry AK000537.

```
  1 GGCACGAGACTCAGTATAAATCCAAATAACCATTCTTGGTTAATT
    G  T  R  L  S  I  N  P  N  N  H  S  W  L  I
 46 ATCCAGGCAGATATTTACTTTGCAACGAATCAGTATTCAGCAGCT
    I  Q  A  D  I  Y  F  A  T  N  Q  Y  S  A  A
 91 CTTCACTATTACCTCCAGGCAGGAGCTGTGTGTTCTGACTTCTTT
    L  H  Y  Y  L  Q  A  G  A  V  C  S  D  F  F
136 AACAAGGCTGTGCCCCCTGATGTTTATACAGACCAGGTAATAAAA
    N  K  A  V  P  P  D  V  Y  T  D  Q  V  I  K
181 CGAATGATAAAATGTTGTTCTTTGCTGAATTGCCACACACAGGTG
    R  M  I  K  C  C  S  L  L  N  C  H  T  Q  V
226 GCTATTTTATGTCAGTTCCTCAGAGAAATTGACTACAAAACAGCG
    A  I  L  C  Q  F  L  R  E  I  D  Y  K  T  A
271 TTTAAATCTCTGCAAGAACAAAACAGTCATGATGCTATGGACTCC
    F  K  S  L  Q  E  Q  N  S  H  D  A  M  D  S
316 TACTACGACTACATATGGGATGTTACCATTTTGGAATACTTGACT
    Y  Y  D  Y  I  W  D  V  T  I  L  E  Y  L  T
361 TATCTTCATCATAAAAGAGGAGAAACAGATAAAAGACAAATTGCA
    Y  L  H  H  K  R  G  E  T  D  K  R  Q  I  A
406 ATCAAAGCCATCGGCCAGACAGAGTTGAATGCAAGCAATCCAGAA
    I  K  A  I  G  Q  T  E  L  N  A  S  N  P  E
451 GAAGTGTTACAGCTGGCAGCGCAGAGAAGGAAAAAAAAGTTTCTC
    E  V  L  Q  L  A  A  Q  R  R  K  K  K  F  L
496 CAAGCAATGGCAAAACTTTACTTTTAAGCAGTTAAATTTTTTTAA
    Q  A  M  A  K  L  Y  F
541 CTTTTATTTTTTAAACAATGGGCTAAAAATAAACAGTATTAAAAG
586 GGTAAGTTTATATAATACAAAAAAAAAAAAAAAAA
```

Fig. 1

```
1   CTCCTGCAGCGGTGGTCGGCTGTTGGGTGTGGAGTTTCCCAGCGC
46  CCCTCGGGTCCGACCCTTTGAGCGTTCTGCTCCGGCGCCACTACC

91  TCGCTCCTCGGCGCCATGACCACAACCACCACCTTCAAGGGAGTC
              MetThrThrThrThrThrPheLysGlyVal

136 GACCCCAACAGCAGGAATAGCTCCCGAGTTTTGCGGCCTCCAGGT
    AspProAsnSerArgAsnSerSerArgValLeuArgProProGly

181 GGTGGATCCAATTTTTCATTAGGTTTTGATGAACCAACAGAACAA
    GlyGlySerAsnPheSerLeuGlyPheAspGluProThrGluGln

226 CCTGTGAGGAAGAACAAAATGGCCTCTAATATCTTTGGGACACCT
    ProValArgLysAsnLysMetAlaSerAsnIlePheGlyThrPro

271 GAAGAAAATCAAGCTTCTTGGGCCAAGTCAGCAGGTGCCAAGTCT
    GluGluAsnGlnAlaSerTrpAlaLysSerAlaGlyAlaLysSer

316 AGTGGTGGCAGGGAAGACTTGGAGTCATCTGGACTGCAGAGAAGG
    SerGlyGlyArgGluAspLeuGluSerSerGlyLeuGlnArgArg

361 AACTCCTCTGAAGCAAGCTCCGGAGACTTCTTAGATCTGAAGGGA
    AsnSerSerGluAlaSerSerGlyAspPheLeuAspLeuLysGly

406 GAAGGTGATATTCATGAAAATGTGGACACAGACTTGCCAGGCAGC
    GluGlyAspIleHisGluAsnValAspThrAspLeuProGlySer

451 CTGGGGCAGAGTGAAGAGAAGCCCGTGCCTNTGCGCCTGTGCCCA
    LeuGlyGlnSerGluGluLysProValProXaaArgLeuCysPro

496 GCCCGGTGCCCCGGCCCCAGTGCCATCCAGAAGAAATCCCCTGGC
    AlaArgCysProGlyProSerAlaIleGlnLysLysSerProGly

541 GGCAAGTCCAGCCTCGTCTTGGGTTAGCTCTGACTGTCCTGAACG
    GlyLysSerSerLeuValLeuGly

586 CTGTCGTTCTGTCTGTTTCCTCCATGCTTGTGAACTGCACAACTT
631 GAGCCTGACTGTACATCTCTTGGATTTGTTTCATTAAAAAGAAGC
676 ACTTTANGTAAAAAAAAAAAAAAAAAAAAAAAAAAAAAAAAAAAA
721 AAAAAACAA
```

Fig. 2

|  | HPS (forward) | HPS (reverse) |
|---|---|---|
| 14-3-3 eta | - | + |
| Hrs | - | + |
| BMK1 alpha | - | + |
| CDK2 | - | + |
| Nuclear factor NF90 | - | + |
| Atrophin-I | - | + |
| DGS-I | - | + |
| HPIP-1 (cg49368.b1, cg49367.h11, cg49424.c10) | + | - |
| HN1 homolog (cgHs2950_0) | + | - |
| Retinoblastoma | - | - |
| p27(Kip1) | - | - |
| RGL-2 | - | - |
| Vector control | - | - |

Fig. 3

ISOLATION AND CHARACTERIZATION OF HERMANSKY PUDLAK SYNDROME (HPS) PROTEIN COMPLEXES AND HPS PROTEIN-INTERACTING PROTEINS

GRANT SUPPORT

The invention disclosed herein was made utilizing United States Government support under Grant Number 70NANB5H1066 awarded by the National Institute of Standards and Technology. Accordingly, the United States Government has certain rights in the invention.

FIELD OF THE INVENTION

The present invention disclosed herein relates to complexes of the Hermansky-Pudlak Syndrome (HPS) protein with other proteins including, but not limited to, complexes of HPS with: 14-3-3 eta, Hrs, BMK1 alpha kinase, CDK2, Nuclear factor NF90, Atrophin-1, DGS-1, HPIP1 and human HN1 homolog protein. The present invention further relates to antibodies specific for HPS complexes, and their use in, inter alia, screening, diagnosis, prognosis and therapy. The present invention further relates to the HPIP1 and human HN1 homolog protein nucleic acid, protein and derivatives, fragments and analogs thereof.

BACKGROUND OF THE INVENTION

(1) Hermansky-Pudlak Syndrome (HPS) and Chediak Higashi Syndrome (CHS)

Hermansky-Pudlak syndrome (HPS) is a genetic disorder characterized by defective lysosome-related organelles. Although the frequency of HPS is quite low in the general population, the frequency is markedly higher in certain genetically-isolated population groups. For example, HPS occurs in northwest Puerto Rico with a prevalence of 1 in 1800. In humans, HPS is characterized by the symptomatic triad of oculocutaneous albinsim, platelet dysfunction (i.e., mild to moderate bleeding diathesis), and ceroid deposition. Tissue accumulation of ceroid pigment (ceroid desposition) is considered to cause several serious complications, including progressive pulmonary fibrosis leading to death in the fourth or fifth decades. The primary defect in HPS involves affects on the contents and/or the secretion of several subcellular organelles, including lysosomes, melanosomes, and platelet-dense granules. See e.g., Swank, et al., 1998. *Pigment Cell Res.* 11:60–80; Erickson, 1997. *Proc. Natl. Acad. Sci. USA* 94:8924–8925. The synthesis of pigmented melanosomes is compromised in HPS patients, wherein functional melanocytes are quantitatively reduced in number and/or are qualitatively abnormal, thus resulting in albinism of both dermal and keratinized tissues (e.g., the skin and hair). See e.g., Gardner, et al., 1997. *Proc. Natl. Acad. Sci. USA* 94:9238–9243. The prolonged bleeding time associated with HPS is due to the lack of the storage organelles, platelet-dense granules, which are required for ADP-release and platelet aggregation. See e.g., Holmsen, et al., 1979. *Ann. Rev. Med.* 30:119–134. The pulmonary fibrosis and granulomatous colitis demonstrated in some cases of HPS is due to the accumulation of ceroid lipofuscin in lysosomes of reticuloendothelial cells, bone marrow and lung macrophages, gastrointestinal mucosal cell, and other cell types. See e.g., Harmon, et al., 1994. *J. Lab. Clin. Med.* 123:617–627.

Similar physiological abnormalities have been shown to occur in the pale ear (ep) mouse. See Lane & Green, 1967. *J. Heredity* 58:17–20. Homozygous recessive ep mice have decreased skin and eye pigment at birth, as well as abnormal organelle function resulting in an increase of serum lysosomal enzymes. See Novak & Swank, 1979. *Genetics* 92:189–204. Similar deleterious physiological symptomology was also described in a murine model of Chediak-Higashi Syndrome (CHS), within the beige mouse. CHS is, like HPS, an autosomal recessive genetic disorder. Symptoms in affected patients involve hypopigmentation, immunological deficiency, a bleeding tendency and a neurological disorder, probably due to protein sorting defects, especially in secretory lysosomes of granular cells. See Spritz, 1998, *J. Clin. Immunol.* 18:97–105. Chediak-Higashi syndrome proteins (LYST and LYST-2) have been identified in mouse and in man. LYST interacting proteins include 14-3-3 protein, HS1 (14-3-3 beta) protein, Hrs, BMK1 alpha kinase, KB07, Efs, OS9, casein kinase II beta SU, calmodulin, Troponin, Importin beta, Fte-1, estrogen-receptor related protein, Imogen 38, Atrophin-1, GBDR1, DGS-I, noHPSin (KIAA0607), OPA containing protein, M4 protein, LIP1 (Tcp-10 homolog), LIP2 (L17 homolog), LIP3 (Roaz protein homolog), LIP4 (hnRNP-e2 homolog), LIP5, LIP6 (Ns2-3 homolog), LIP7 (TCP10A homolog), LIP8 (KAP4L homolog), LIP9 (etr-1 homolog), and LIP10, as described in U.S. patent application Ser. No. 09/054,956.

The gene encoding a HPS-related protein has recently been cloned in both humans and mice. See Oh, et al., 1996. *Nat. Genet.* 14:300–306; Gardner, et al., 1997. *Proc. Natl. Acad. Sci. USA* 94:9238–9243. Sequence analysis has predicted this polypeptide (hereinafter the "HPS protein") to be a component of cytoplasmic organelles due to the presence of a putative transmembranal region. The mRNA encoded by the HPS gene in ep mice appears to be very widely expressed.

In summary, it is most likely that both human and murine HPS symptoms results from a defect in a protein which is required for the normal assembly, maturation, and/or structure of numerous, diverse subcellular organelles. Accordingly, HPS is likely to be centrally implicated in pathological processes, including but not limited to, oculocutaneous albinism, fibrotic lung disease, and various clotting, bleeding, and neurodegenerative disorders.

(2) HPS Protein-Interacting Proteins of the Present Invention

As previously discussed, HPS patients have been reported to suffer from several serious medical conditions, including oculocutaneous albinsim, a bleeding diathesis, and ceroid deposition, often accompanied by severe fibrotic lung disease and granulomatous colitis. However, despite the recognition of these HPS-associated syndromes, no curative therapeutic intervention currently exists for this disease. Currently, only symptomatic treatment can be offered. One potential area of difficulty involves a lack of understanding regarding the interaction of the HPS protein with other cellular proteins. The elucidation of these potential interactions may provide the means for the subsequent development of an diagnostic assay and/or a therapeutic modality for HPS and its associated diseases.

The following sections will discuss the various proteins which have been shown to interact with the HPS protein. These HPS protein-interacting-proteins hereinafter "HPS-IP" may be differentiated into proteins which are involved in signaling processes and protein trafficking (14-3-3 eta, Hrs, BMK1 alpha, CDK2, NF90), those proteins involved in neurodegenerative and developmental disorders (Atrophin I, DGS-1) and those previously-uncharacterized, novel proteins (HPIP1, HN1 homolog). Interestingly, five of these nine interacting proteins, or similar proteins, were found to interact as well with the LYST protein, as described by Nandabalan and Kingsmore in U.S. patent application Ser. No. 09/054,956 (Apr. 3, 1998): 14-3-3 protein, HS1 (14-3-3 beta) protein, Hrs, BMK1 alpha kinase, Atrophin-1, and DGS-I. CDK2, NF 90, HPIP1, and HN1 homolog were not found to interact with LYST. Table I provides an overview of all HPS interacting proteins and their interacting domains as disclosed in by the present invention.

It should be noted that the citation of a reference in this or in any other section of the specification should not be construed as an admission that such reference is prior art to the present invention disclosed herein.

(A) Proteins Involved Signaling Processes and Protein Trafficking (i) 14-3-3 eta The caHPSoxy-terminal region (starting at nucleotide 764) of the 14-3-3 protein eta isoform (GenBank Accession Number X80536; Ichimura-Ohshima, et al., 1992. *J. Neurosci. Res.* 31:600–605) was found to interact with HPS protein in this invention. The nucleotide and amino acid sequences of a Hermansky-Pudlak Syndrome Protein sequence provided in GenBank Accession Number U65676 are as follows:

```
   1 gggcgctgtg cgcgccgcga tccggtacgt gggcctccgg gctgtccoct ctggggggcga  (SEQ ID NO:5)
  61 tcctccctcc ggagccoccc ttcaaccctc ccggaagtga ggaccaggga tgctgtgctg
 121 ctctcccatg agccagtcac cgagtcggtc tgctgcagcc ctttctgaac ctctggccgt
 181 ctggatgctc cactgtgctt gccaagatga agtgcgtctt ggtggccact gagggcgcag
 241 aggtcctctt ctactggaca gatcaggagt ttgaagagag tctccggctg aagttcgggc
 301 agtcagagaa tgaggaagaa gagctccctg ccctggagga ccagctcagc accctcctag
 361 ccccggtcat catctcctcc atgacgatgc tggagaagct ctcggacacc tacacctgct
 421 tctccacgga aaatggcaac ttcctgtatg tccttcacct gtttggagaa tgcctgttca
 481 ttgccatcaa tggtgaccac accgagagcg aggggggacct gcggcggaag ctgtatgtgc
 541 tcaagtacct gtttgaagtg cactttgggc tggtgactgt ggacggtcat cttatccgaa
 601 aggagctgcg gcccccagac ctggcgcagc gtgtccagct gtgggagcac ttccagagcc
 661 tgctgtggac ctacagccgc ctgcgggagc aggagcagtg cttcgccgtg gaggccctgg
 721 agcgactgat tcacccccag ctctgtgagc tgtgcataga ggcgctggag cggcacgtca
 781 tccaggctgt caacaccagc cccgagcggg gaggcgagga ggccctgcat gccttcctgc
 841 tcgtgcactc caagctgctg gcattctact ctagccacag tgccagctcc ctgcgcccgg
 901 ccgacctgct tgccctcatc ctcctggttc aggacctcta ccccagcgag agcacagcag
 961 aggacgacat tcagccttcc ccgcggaggg cccggagcag ccagaacatc cccgtgcagc
1021 aggcctggag ccctcactcc acgggcccaa ctgggggggag ctctgcagag acggagacag
1081 acagcttctc cctccctgag gagtacttca caccagctcc ttccctggc gatcagagct
1141 caggtagcac catctggctg gaggggggca cccccccccat ggatgcectt cagatagcag
1201 aggacaccct ccaaacactg gttccccact gccctgtgcc ttccggcccc agaaggatct
1261 tcctggatgc caacgtgaag gaaagctact gcccctagt gccccacacc atgtactgcc
1321 tgccoctgtg gcagggcatc aacctggtgc tcctgaccag gagcoccagc gcgcccctgg
1381 ccctggttct gtcccagctg atggatggct tctccatgct ggagaagaag ctgaaggaag
1441 ggccggagcc cggggcctcc ctgcgctccc agccectcgt gggagacctg cgccagagga
1501 tggacaagtt tgtcaagaat cgaggggcac aggagattca gagcacctgg ctggagttta
1561 aggccaaggc tttctccaaa agtgagcccg gatcctcctg ggagctgctc caggcatgtg
1621 ggaagctgaa gcggcagctc tgcgccatct accggctgaa ctttctgacc acagccccca
1681 gcaggggagg cccacacctg ccccagcacc tgcaggacca agtgcagagg ctcatgcggg
1741 agaagctgac ggactggaag gacttcttgc tggtgaagag caggaggaac atcaccatgg
1801 tgtcctacct agaagacttc ccaggcttgg tgcacttcat ctatgtggac cgcaccactg
1861 ggcagatggt ggcgccttcc ctcaactgca gtcaaaagac ctcgtcggag ttgggcaagg
```

-continued

```
1921 ggccgctggc tgcctttgtc aaaactaagg tctggtctct gatccagctg gcgcgcagat
1981 acctgcagaa gggctacacc acgctgctgt tccgggaggg ggatttctac tgctcctact
2041 tcctgtggtt cgagaatgac atggggtaca aactccagat gatcgaggtg cccgtcctct
2101 ccgacgactc agtgcctatc ggcatgctgg aggagacta ctacaggaag ctcctgcgct
2161 actacagcaa gaaccgccca accgaggctg tcaggtgcta cgagctgctg gccctgcacc
2221 tgtctgtcat ccccactgac ctgctggtgc agcaggccgg ccagctggcc cggcgcctct
2281 gggaggcctc ccgtatcccc ctgctctagg ccaaggtggc cgcagtctgc ctttgcatcc
2341 tgtcctccag ccaccettgc ttgccactgt tccccatgac gagagcctcc tgtctgcagt
2401 ggccatcctg aggatagggc agagtgccca gggtggcccc agggcttcta aacccccacc
2461 tagaccaccc tccatgtcag gtactgagca aggcccaga tccttctctc tggaggaaga
2521 gggaagccca ggggtcctgt ttgtaaaaca acggtggcaa cagctcctct tccagagctg
2581 cctctgcctt tatcctggga gatggggagg aagccccatc tctgctgttc cctgcgtgga
2641 ggaagcccac ccagcaagct ctctcctacc ccaggtaaaa ggtgctcctt tgcctgggtt
2701 tgaattccag cgctgccact tcctctctgc acctcctggc aagtttcttc tattccccac
2761 gtttaaagcg atggcacctc cgtcccaggg tggtgtgagg attacccagt gtggtaggtg
2821 ctcaataaat gttggtcatt gttatcactg aagcccaaca tgctagtgct tctagaccct
2881 tctgtcagtg ctgataagcc cttgctaagt cccagcccct tcatgcttgg ctggcgtctg
2941 ccctagggct ggggttctca agcccctggc cctggcccag agatttggat tcccttggcg
3001 gccgtggagc ccaggctttg atgtctttca aagcttctgt ggtgcgccct ggattgagaa
3061 ccaccacccg aggggtacag cccctctctt ccaaccgaga agttcctgtc cagaatggac
3121 ccagggacaa gagaccctga gagccctggg actgggagtg tctgctcctc tgagccagga
3181 ggccggtgct gggccagaga ggacggcgtg gcgaaagtca gcgtccactg cagcacagga
3241 tcagatggcc gtgtgctgtg catgcaggag cctcgccttc tgtgtcttta gtcttgagcc
3301 aaaatttgct caaaagactg atctcttcct tgcagggaac agctttgggg ctgggggaac
3361 tagaacccac atgttggtct aaaccctgag aaggtggcag tgaggaagta tcccctcagg
3421 tgactggatc tgtgttcctc cttaacatca tctgatggaa tggcaatgaa aagcgtggat
3481 tgtggaaaat acagaaaaac ataaaggaaa aaactccaat cccctgagcc caccactgtt
3541 caggacccct gcttttgtca cctactattt ccctttagtt tttagcagcg gctggatgtg
3601 atatgtctag tttaaccagt ccccttgatc tttctatata ataataaca caggagtgaa
3661 catcctgaat cag
```

```
  1 MKCVLVATEGAEVLFYWTDQEFEESLRLKFGQSENEEEELPALEDQLSTL         (SEQ ID NO:6)
 51 LAPVIISSMTMLEKLSDTYTCFSTENGNFLYVLHLFGECLFIAINGDHTE
101 SEGDLRRKLYVLKYLFEVHFGLVTVDGHLIRKELRPPDLAQRVQLWEHFQ
151 SLLWTYSRLREQEQCFAVEALERLIHPQLCELCIEALERHVIQAVNTSPE
201 RGGEEALHAFLLVHSKLLAFYSSHSASSLRPADLLALILLVQDLYPSEST
251 AEDDIQPSPRRARSSQNIPVQQAWSPHSTGPTGSSAETETDSFSLPEEY
301 FTPAPSPGDQSSGSTIWLEGGTPPMDALQIAEDTLQTLVPHCPVPSGPRR
351 IFLDANVKESYCPLVPHTMYCLPLWQGINLVLLTRSPSAPLALVLSQLMD
401 GFSMLEKKLKEGPEPGASLRSQPLVGDLRQRMDKFVKNRGAQEIQSTWLE
451 FKAKAFSKSEPGSSWELLQACGKLKRQLCAIYRLNFLTTAPSRGGPHLPQ
```

-continued

```
501 HLQDQVQRLMREKLTDWKDFLLVKSRRNITMVSYLEDFPGLVHFIYVDRT

551 TGQMVAPSLNCSQKTSSELGKGPLAAFVKTKVWSLIQLARRYLQKGYTTL

601 LFREGDFYCSYFLWFENDMGYKLQMIEVPVLSDDSVPIGMLGGDYYRKLL

651 RYYSKNRPTEAVRCYELLALHLSVIPTDLLVQQAGQLARRLWEASRIPLL
```

Interestingly, the highly homologous proteins 14-3-3 protein and HS1 (14-3-3 beta) protein were described as LYST interacting protein in U.S. patent application Ser. No. 09/054,956 (filed Apr. 3, 1998). The highly conserved 14-3-3 family of proteins is found in a broad range of organisms and tissues and have been associated with many diverse biological functions, including signal transduction, exocytosis and cell-cycle regulation. The 14-3-3 proteins have been demonstrated to associate with a wide-range of cellular and viral polypeptides involved in signal transduction, cell cycle regulation and/or oncogenesis, suggesting that they participate in cellular growth regulation. See e.g., Aitken, 1995. Trends Biochem. Sci. 20:95–97. For example, the eta isoform interacts with several kinases, implicating 14-3-3 eta proteins in intracellular signal transduction cascades and cellular protein networks. The nucleotide and amino acid sequences of a 14-3-3 eta sequence provided in GenBank Accession Number X80536 is as follows:

```
   1 gaattcgcgg cgccgagagg gcgcgagcgg cggcgctgcc tgcagcctgc agcctgcagc   (SEQ ID NO:7)

61 ctccggccgg ccggcgagcc agtgcgcgtg cgcggcggcg gcctccgcag cgaccgggga 121 gcggactgac cggcgggagg gctagcgagc cagcggtgtg aggcgcgagg cgaggccgag 181 ccgcgagcga catgggggac cgggagcagc tgctgcagcg ggcgcggctg gccgagcagg 241 cggagcgcta cgacgacatg gcctccgcta tgaaggcggt gacagagctg aatgaacctc 301 tctccaatga agatcgaaat ctcctctctg tggcctacaa gaatgtggtt ggtgccaggc 361 gatcttcctg gagggtcatt agcagcattg agcagaaaac catggctgat ggaaacgaaa 421 agaaattgga gaaagttaaa gcttaccggg agaagattga gaaggagctg gagacagttt 481 gcaatgatgt cctgtctctg cttgacaagt tcctgatcaa gaactgcaat gatttccagt 541 atgagagcaa ggtgttttac ctgaaaatga agggtgatta ctaccgctac ttagcagagg 601 tcgcttctgg ggagaagaaa aacagtgtgg tcgaagcttc tgaagctgcc tacaaggaag 661 cctttgaaat cagcaaagag cagatgcaac ccacgcatcc catccggctg ggcctggccc 721 tcaacttctc cgtgttctac tatgagatcc agaatgcacc tgagcaagcc tgcctcttag 781 ccaaacaagc cttcgatgat gccatagctg agctggacac actaaacgag gattcctata 841 aggactccac gctgatcatg cagttgctgc gagacaacct cacccttggt acgagcgacc 901 agcaggatga agaagcagga gaaggcaact gaagatcctt caggtcccct agcccttcct 961 tcacccacca cccccatcat caccgattct tccttgccac aatcactaaa tatctagtgc 1021 taaacctatc tgtattggca gcacagctac tcagatctgc actcctgtct cttgggaagc 1081 agtttcagat aaatcatggg cattgctgga ctgatggttg ctttgagccc acaggagctc 1141 ccttttttgaa ttgtgtggag aagtgtgttc tgatgaggca ttttactatg cctgttgatc 1201 tatgggaaat ctaggcgaaa gtaatgggga agattagaaa gaattagcca accaggctac 1261 agttgatatt taaaagatcc atttaaaaca agctgatagt gtttcgttaa gcagtacatc 1321 ttgtgcatgc aaaaatgaat tcacccctcc cacctctttc ttcaattaat ggaaaactgt 1381 taagggaagc tgatacagag agacaacttg ctcctttcca tcagctttat aataaactgt 1441 ttaacgtgag gtttcagtag ctccttggtt ttgcctcttt aaattatgac gtgcacaaac 1501 cttcttttca atgcaatgca tctgaaagtt ttgatacttg taactttttt tttttttgg 1561 ttgcaattgt ttaagaatca tggatttatt ttttgtaact ctttggctat tgtccttgtg 1621 tatcctgaca gcgccatgtg tgtcagccca tgtcaatcaa gatgggtgat tatgaaatgc
```

```
1681 cagacttcta aaataaatgt tttggaattc aatgggtaaa taaatgcgac

1 MGDREQLLQRARLAEQAERYDDMASAMKAVTELNEPLSNEDRNLLSVAYK                (SEQ ID NO:8)

51 NVVGARRSSWRVISSIEQKTMADGNEKKLEKVKAYREKIEKELETVCNDV

101 LSLLDKFLIKNCNDFQYESKVFYLKMKGDYYRYLAEVASGEKKNSVVEAS

151 EAAYKEAFEISKEQMQPTHPIRLGLALNFSVFYYEIQNAPEQACLLAKQA

201 FDDAIAELDTLNEDSYKDSTLIMQLLRDNLTLWTSDQQDEEAGEGN 246
```

In addition, calcium-dependent exocytosis in permeabilized adrenal chromaffin cells has been demonstrated to be mediated by several proteins, including, but not limited to, 14-3-3 proteins (see e.g., Morgan & Burgoyne, 1992. *Nature* 355:833–836); alpha-SNAP proteins (see e.g., Morgan & Burgoyne, 1995. *EMBO J.* 14:323–239); and protein kinase C (see e.g., Morgan & Burgoyne, 1992. *Nature* 355:833–836). Furthermore, 14-3-3 proteins may enhance catecholamine release in permeabilized cells by reorganizing the cortical actin-barrier to allow the increased availability of secretory vesicles for exocytotic release. See e.g., Roth & Burgoyne, 1995. *FEBS Letters* 374:77–81.

The 14-3-3 family of proteins (including the eta isoform), activate tryptophan and tryptophan hydroxylase in brain tissue, which is one of the rate-limiting steps in catechol amine and serotonin neurotransmitter biosynthesis (see e.g., Banik, et al., 1997. *J. Biol. Chem.* 272:26219–26225). 14-3-3 proteins have been demonstrated within the neurofibrillary tangles seen in Alzheimer's Disease. This association may be due to the 14-3-3 protein's affect on MAP kinase signaling, which causes hyper-phosphorylation of the tau protein. This tau protein hyper-phosphorylation is believed to lead to the formation of the paired helical filaments seen in the brains of Alzheimer's Disease victims. See e.g., Layfield, et al., 1996. *Neurosci. Lett.* 209:57–60. Moreover, 14-3-3 proteins have also been shown in the cerebrospinal fluid of patients with Creutzfeldt-Jakob disease. See e.g., Rosenmann, et al., 1997. *Neurol.* 49:593–595. In summary, there is a strong implication for the involvement of the 14-3-3 family of proteins, including the eta isoform, in neurodegenerative disorders. In addition, 14-3-3 eta plays roles in is signal tranduction, cell cycle regulation and oncogenesis.

(ii) Hrs Protein

Another protein which was found to interact with the HPS protein was Hrs (hepatocyte growth factor-regulated tyrosine kinase substrate) protein [GenBank Accession No. D84064; Lu et al., 1998. *Gene* 213:125–135]. In addition, Hrs was described as interactant of the Chediak-Higashi Protein LYST (see U.S. patent application Ser. No. 09/054, 956, filed Apr. 3, 1998). Hrs is a 115 Kdal cytoplasmic protein with a structurally-conserved, putative zinc-finger binding domain and several proline-rich regions. See e.g., Komada & Kitamura, 1995. *Mol. Cell. Biol.* 15:6213–6221. The phosphorylation of tyrosine residues within the Hrs protein may be induced by the treatment of cells with epidermal growth factor or platelet-derived growth factor. It is thus likely that Hrs plays a role in the intracellular signaling pathway of these aforementioned growth factors. The nucleotide and amino acid sequences of a Hrs sequence provided in GenBank Accession Number D84064 is as follows:

```
  1 gggcgcgcca gctcgtagca ggggagcgcc cgcggcgtcg ggtttgggct ggaggtcgcc  (SEQ ID NO:9)

61 atggggcgag gcagcggcac cttcgagcgt ctcctagaca aggcgaccag ccagctcctg 121 ttggagacag attgggagtc cattttgcag atctgcgacc tgatccgcca aggggacaca 181 caagcaaaat atgctgtgaa ttccatcaag aagaaagtca acgacaagaa cccacacgtc 241 gccttgtatg ccctggaggt catggaatct gtggtaaaga actgtggcca gacagttcat 301 gatgaggtgg ccaacaagca gaccatggag gagctgaagg acctgctgaa gagacaagtg 361 gaggtaaacg tccgtaacaa gatcctgtac ctgatccagg cctgggcgca tgccttccgg 421 aacgagccca agtacaaggt ggtccaggac acctaccaga tcatgaaggt ggaggggcac 481 gtctttccag aattcaaaga gagcgatgcc atgtttgctg ccgagagagc cccagactgg 541 gtggacgctg aggaatgcca ccgctgcagg gtgcagttcg gggtgatgac ccgtaagcac 601 cactgccggg cgtgtgggca gatattctgt ggaaagtgtt cttccaagta ctccaccatc 661 cccaagtttg gcatcgagaa ggaggtgcgc gtgtgtgagc cctgctacga gcagctgaac 721 aggaaagcgg agggaaaggc cacttccacc actgagctgc cccccgagta cctgaccagc 781 cccctgtctc agcagtccca gctgcccccc aagagggacg agacggccct gcaggaggag 841 gaggagctgc agctggccct ggcgctgtca cagtcagagg cggaggagaa ggagaggctg
```

-continued

```
 901 agacagaagt ccacgtacac ttcgtacccc aaggcggagc ccatgccctc ggcctcctca
 961 gcgcccccg ccagcagcct gtactcttca cctgtgaact cgtcggcgcc tctggctgag
1021 gacatcgacc ctgagctcgc acggtatctc aaccggaact actgggagaa gaagcaggag
1081 gaggctcgca agagccccac gccatctgcg cccgtgcccc tgacggagcc ggctgcacag
1141 cctggggaag gcacgcagc ccccaccaac gtggtggaga accccctccc ggagacagac
1201 tctcagccca ttcctccctc tggtggcccc tttagtgagc acagttcca caatggcgag
1261 tctgaggaga gccacgagca gttcctgaag gcgctgcaga acgccgtcac caccttcgtg
1321 aaccgcatga agagtaacca catgcggggc cgcagcatca ccaatgactc ggccgtgctc
1381 tcactcttcc agtccatcaa cggcatgcac ccgcagctgc tggagctgct caaccagctg
1441 gacgagcgca ggctgtacta tgaggggctg caggacaagc tggcacagat ccgcgatgcc
1501 cggggggcgc tgagtgccct gcgcgaagag caccgggaga gcttcgccg gcagccgag
1561 gaggcagagc gccagcgcca gatccagctg gcccagaagc tggagataat gcggcagaag
1621 aagcaggagt acctggaggt gcagaggcag ctggccatcc agcgcctgca ggagcaggag
1681 aaggagcggc agatgcggct ggagcagcag aagcagacgg tccagatgcg cgcgcagatg
1741 cccgccttcc ccctgcccta cgcccagctc caggccatgc ccgcagccgg aggtgtgctc
1801 taccagcccct cgggaccagc cagcttcccc agcaccttca gccctgccgg ctcggtggag
1861 ggctccccaa tgcacggcgt gtacatgagc cagccggccc ctgccgctgg ccctaccccc
1921 agcatgccca gcactgcggc tgatcccagc atggtgagtg cctacatgta cccagcaggg
1981 gccactgggg cgcaggcggc cccccaggcc caggccggac ccaccgccag ccccgcttac
2041 tcatcctacc agcctactcc cacagcgggc taccagaacg tggcctccca ggccccacag
2101 agcctcccgg ccatctctca gcctccgcag tccagcacca tgggctacat ggggagccag
2161 tcagtctcca tgggctacca gccttacaac atgcagaatc tcatgaccac cctcccaagc
2221 caggatgcgt ctctgccacc ccagcagccc tacatcgcgg ggcagcagcc catgtaccag
2281 cagatggcac cctctggcgg tccccccag cagcagcccc ccgtggccca gcaaccgcag
2341 gcacaggggc cgccggcaca gggcagcgag gcccagctca tttcattcga ctgacccagg
2401 ccatgctcac gtccggagta acactacata cagttcacct gaaacgcctc gtctctaact
2461 gccgtcgtcc tgcctccctg tcctctactg ccggtagtgt cccttctctg cgagtgaggg
2521 ggggccttca ccccaagccc acctccctg tcctcagcct actgcagtcc ctgagttagt
2581 ctctgctttc tttcccagg gctgggccat ggggaggaa ggactttctc ccaggggaag
2641 cccccagccc tgtgggtcat ggtctgtgag aggtggcagg aatggggacc ctcaccccc
2701 aagcagcctg tgccctctgg ccgcactgtg agctggctgt ggtgtctggg tgtggcctgg
2761 ggctccctct gcagggggcct ctctcggcag ccacagccaa gggtggaggc ttcaggtctc
2821 cagcttctct gcttctcagc tgccatctcc agtgccccag aatggtacag cgataataaa
2881 atgtatttca gaaagg
```

```
  1 MGRGSGTFERLLDKATSQLLLETDWESILQICDLIRQGDTQAKYAVNSIK        (SEQ ID NO:10)
 51 KKVNDKNPHVALYALEVMESVVKNCGQTVHDEVANKQTMEELKDLLKRQV
101 EVNVRNKILYLIQAWAHAFRNEPKYKVVQDTYQIMKVEGHVFPEFKESDA
151 MFAAERAPDWVDAEECHRCRVQFGVMTRKHHCRACGQIFCGKCSSKYSTI
201 PKFGIEKEVRVCEPCYEQLNRKAEGKATSTTELPPEYLTSPLSQQSQLPP
251 KRDETALQEEEELQLALALSQSEAEEKERLRQKSTYTSYPKAEPMPSASS
```

-continued

```
301 APPASSLYSSPVNSSAPLAEDIDPELARYLNRNYEKKQEEARKSPTPSAP

351 VPLTEPAAQPGEGHAAPTNVVENPLPETDSQPIPPSGGPFSEPQFHNGES

401 EESHEQFLKALQNAVTTFVNRMKSNHMRGRSITNDSAVLSLFQSINGMHP

451 QLLELLNQLDERRLYYEGLQDKLAQIRDARGALSALREEHREKLRRAAEE

501 AERQRQIQLAQKLEIMRQKKQEYLEVQRQLAIQRLQEQEKERQMRLEQQK

551 QTVQMRAQMPAFPLPYAQLQAMPAAGGVLYQPSGPASFPSTFSPAGSVEG

601 SPMHGVYMSQPAPAAGPYPSMPSTAADPSMVSAYMYPAGATGAQAAPQAQ

651 AGPTASPAYSSYQPTPTAGYQNVASQAPQSLPAISQPPQSSTMGYMGSQS

701 VSMGYQPYNMQNLMTTLPSQDASLPPQQPYIAGQQPMYQQMAPSGGPPQQ

751 QPPVAQQPQAQGPPAQGSEAQLISFD
```

Hrs has been shown to exhibit an 80% homology with rat Hrs-2, an enzyme with ATPase catalytic activity. Hrs-2 was characterized as a brain protein which interacts with SNAP-25, a plasma membrane protein involved in vesicular transport (i.e., vesicular docking and fusion). Synaptic vesicle docking and calcium-dependent exocytosis require the specific interaction of various synaptic vesicle membrane proteins (e.g., VAMP and synaptogamin) with their plasma membrane-localized counterparts (e.g., SNAP-25 and syntaxin). See Sollner, et al., 1993. *Cell* 75:409–418. It was then demonstrated that Hrs-2 functioned to significantly inhibit secretion in a dose-dependent manner, and thus, may be a modulator of exocytosis. Specifically, the binding of Hrs-2 to SNAP-25 is inhibited by calcium at a concentration which is required to support synaptic transmission. Thus, Hrs-2 (and the homologous human protein Hrs) may act as regulators of secretory processes through calcium- and nucleotide-dependent modulation of vesicle-trafficking protein complexes (e.g., SNAP-25). See e.g., Bean, et al., 1997 *Nature* 385:826–829.

(iii) BMK1 alpha kinase

The caHPSoxy-terminal region (starting at nucleotide 2431) of the BMK1 alpha kinase (GenBank Accession Number U29725) was found to interact with HPS protein, as disclosed in this ivention. Interestingly, the same domain of BMK1 alpha kinase was also found to interact with the LYST protein that plays a key role in Chediak Higashi Syndrome. The activated protein kinase BMK1 is part of a distinct signalling pathway that is required for proliferation and progression through the cell cycle (see, e.g., Lee, et al., 1995. *Biochem. Biophys. Res. Commun.* 213(2):715–724. The nucleotide and amino acid sequences of a BMPK1 kinase sequence provided in GenBank Accession Number U29725 is as follows:

```
  1 gtccaacttg gccggaagct gcggagaggc tcagccaccg gaagtcagtg gagggttcgg  (SEQ ID NO:11)

61 ccggacgctc tagaatcccg gaggaccggg atctctgtgg ttggccgtga cgggcaccct 121 ctaccgggga tgacacattc ccagagctcc tgggaccaag caaatggcgg acacaattcc 181 ctgggcggaa ggggacttcg ggagccagta gccaagacac catggccgag cctctgaagg 241 aggaagacgg cgaggacggc tctgcggagc ccccgggcc cgtgaaggtc gaacccgccc 301 acaccgctgc ctctgtagcg gccaagaacc tggccctgct taaagcccgc tccttcgatg 361 tgacctttga cgtgggcgac gagtacgaga tcatcgagac cataggcaac ggggcctatg 421 gagtggtgtc ctccgcccgc cgccgcctca ccggccagca ggtggccatc aagaagatcc 481 ctaatgcttt cgatgtggtg accaatgcca agcggaccct cagggagctg aagatcctca 541 agcactttaa acacgacaac atcatcgcca tcaaggacat cctgaggccc accgtgccct 601 atggcgaatt caaatctgtc tacgtggtcc tggacctgat ggaaagcgac ctgcaccaga 661 tcatccactc ctcacagccc ctcacactgg aacacgtgcg ctacttcctg taccaactgc 721 tgcggggcct gaagtacatg cactcggctc aggtcatcca ccgtgacctg aagccctcca 781 acctattggt gaatgagaac tgtgagctca agattggtga ctttggtatg gctcgtggcc 841 tgtgcacctc gcccgctgaa catcagtact tcatgactga gtatgtggcc acgcgctggt 901 accgtgcgcc cgagctcatg ctctctttgc atgagtatac acaggctatt gacctctggt 961 ctgtgggctg catctttggt gagatgctgg cccggcgcca gctcttccca ggcaaaaact
```

-continued

```
1021 atgtccacca gctacagctc atcatgatgg tgctgggtac cccatcacca gccgtgattc
1081 aggctgtggg ggctgagagg gtgcgggcct atatccagag cttgccacca cgccagcctg
1141 tgccctggga gacagtgtac ccaggtgccg accgccaggc cctatcactg ctgggtcgca
1201 tgctgcgttt tgagcccagc gctcgcatct cagcagctgc tgcccttcgc cacccttttcc
1261 tggccaagta ccatgatcct gatgatgagc ctgactgtgc ccgcccttt gactttgcct
1321 ttgaccgcga agccctcact cgggagcgca ttaaggaggc cattgtggct gaaattgagg
1381 acttccatgc aaggcgtgag ggcatccgcc aacagatccg cttccagcct tctctacagc
1441 ctgtggctag tgagcctggc tgtccagatg ttgaaatgcc cagtccctgg ctcccagtg
1501 gggactgtgc catggagtct ccaccaccag ccccgccacc atgccccggc cctgcacctg
1561 acaccattga tctgaccctg cagccacctc caccagtcag tgagcctgcc caccaaaga
1621 aagatggtgc catctcagac aatactaagg ctgcccttaa agctgccctg ctcaagtctt
1681 tgaggagccg gctcagagat ggccccagcg caccctgga ggctcctgag cctcggaagc
1741 cggtgacagc ccaggagcgc cagcgggagc gggaggagaa gcggcggagg cggcaagaac
1801 gagccaagga gcgggagaaa cggcggcagg agcgggagcg aaaggaacgg ggggctgggg
1861 cctctggggg ccctccact gaccccttgg ctggactagt gctcagtgac aatgacagaa
1921 gcctgttgga acgctggact cgaatggccc ggccgcagc cccagccctc acctctgtgc
1981 cggcccctgc cccagcgcca acgccaaccc caaccccagt ccaacctacc agtcctcctc
2041 ctggccctgt agcccagccc actggccgc aaccacaatc tgcgggctct acctctggcc
2101 ctgtacccca gctgcctgc ccacccctg gccctgcacc cacccact ggccctcctg
2161 ggccatcccc tgtccccgcg ccaccccaga ttgccacctc caccagcctc ctggctgccc
2221 agtcacttgt gccacccct gggctgcctg gctccagcac cccaggagtt ttgccttact
2281 tcccacctgg cctgccgccc cagacgccg ggggagcccc tcagtcttcc atgtcagagt
2341 cacctgatgt caaccttgtg acccagcagc tatctaagtc acaggtggag gaccccctgc
2401 cccctgtgtt ctcaggcaca ccaaaggca gtggggctgg ctacggtgtt ggctttgacc
2461 tggaggaatt cttaaaccag tctttcgaca tgggcgtggc tgatgggcca caggatggcc
2521 aggcagattc agcctctctc tcagcctccc tgcttgctga ctggctcgaa ggccatggca
2581 tgaaccctgc cgatattgag tccctgcagc gtgagatcca gatggactcc ccaatgctgc
2641 tggctgacct gcctgacctc caggacccct gaggccccca gcctgtgcct tgctgccaca
2701 gtagacctag ttccaggatc catgggagca ttctcaaagg ctttagccct ggacccagca
2761 ggtgaggctc ggcttggatt attctgcagg ttcatctcag acccaccttt cagccttaag
2821 cagccacctg agccaccacc gagccatggc aggatcggga gaccccaact cccctgaac
2881 aatccttttc agtattatat ttttattatt attatgttat tattacactg tcttttgcc
2941 atcaaaatga ggcctgtgaa atacaaggtt ccctttctgca
```

```
  1 MAEPLKEEDGEDGSAEPPGPVKVEPAHTAASVAAKNLALLKARSFDVTFD        (SEQ ID NO:12)
 51 VGDEYEIIETIGNGAYGVVSSARRRLTGQQVAIKKIPNAFDVVTNAKRTL
101 RELKILKHFKHDNIIAIKDILRPTVPYGEFKSVYVVLDLMESDLHQIIHS
151 SQPLTLEHVRYFLYQLLRGLKYMHSAQVIHRDLKPSNLLVNENCELKIGD
201 FGMARGLCTSPAEHQYFMTEYVATRWYRAPELMLSLHEYTQAIDLWSVGC
251 IFGEMLARRQLFPGKNYVHQLQLIMMVLGTPSPAVIQAVGAERVRAYIQS
301 LPPRQPVPWETVYPGADRQALSLLGRMLRFEPSARISAAAALRHPFLAKY
```

-continued

```
351 HDPDDEPDCAPPFDFAFDREALTRERIKEAIVAEIEDFHARREGIRQQIR
401 FQPSLQPVASEPGCPDVEMPSPWAPSGDCAMESPPPAPPPCPGPAPDTID
451 LTLQPPPPVSEPAPPKKDGAISDNTKAALKAALLKSLRSRLRDGPSAPLE
501 APEPRKPVTAQERQREREEKRRRRQERAKEREKRRQERERKERGAGASGG
551 PSTDPLAGLVLSDNDRSLLERWTRMARPAAPALTSVPAPAPAPTPTPTPV
601 QPTSPPPGPVAQPTGPQPQSAGSTSGPVPQPACPPPGPAPHPTGPPGPIP
651 VPAPPQIATSTSLLAAQSLVPPPGLPGSSTPGVLPYFPPGLPPPDAGGAP
701 QSSMSESPDVNLVTQQLSKSQVEDPLPPVFSGTPKGSGAGYGVGFDLEEF
751 LNQSFDMGVADGPQDGQADSASLSASLLADWLEGHGMNPADIESLQRE I
801 QMDSPMLLADLPDLQDP 818
```

(iv) CDK2

Another HPS protein-IP is the cell cycle regulator CDK2 (GenBank Accession Number X61622; Elledge & Spottswood, 1991. *EMBO J.* 10:2653–2659). In the mammalian cell cycle, the transition from the G1 phase to DNA replication phase is regulated by the cyclin-dependent kinases (CDKs). Activities of CDKs are controlled by association with cyclins and reversible phosphorylation reactions. An additional level of regulation is provided by inhibitors of CDKs. CDK2 is expressed in, for example, but not limited to, the majority of squamous cell carcinomas, small cell carcinomas, and large cell carcinomas. Higher CDK2 kinase activity is critical for promoting cell cycle progression and unrestrained proliferation of tumor cells. The nucleotide and amino acid sequences of a CDK2 sequence provided in GenBank Accession Number X61622 is as follows:

```
   1 atggagaact tccaaaaggt ggaaaagatc ggagagggca cgtacggagt tgtgtacaaa   (SEQ ID NO:13)
  61 gccagaaaca agttgacggg agaggtggtg gcgcttaaga aaatccgcct ggacactgag
 121 actgagggtg tgcccagtac tgccatccga gagatctctc tgcttaagga gcttaaccat
 181 cctaatattg tcaagctgct ggatgtcatt cacacagaaa ataaactcta cctggttttt
 241 gaatttctgc accaagatct caagaaattc atggatgcct ctgctctcac tggcattcct
 301 cttcccctca tcaagagcta tctgttccag ctgctccagg gcctagcttt ctgccattct
 361 catcgggtcc tccaccgaga ccttaaacct cagaatctgc ttattaacac agaggggggcc
 421 atcaagctag cagactttgg actagccaga gcttttggag tccctgttcg tacttacacc
 481 catgaggtgg tgaccctgtg gtaccgagct cctgaaatcc tctgggctc gaaatattat
 541 tccacagctg tggacatctg gagcctgggc tgcatctttg ctgagatggt gactcgccgg
 601 gccctgttcc ctggagattc tgagattgac cagctcttcc ggatctttcg gactctgggg
 661 acccagatg aggtggtgtg gccaggagtt acttctatgc ctgattacaa gccaagtttc
 721 cccaagtggg cccggcaaga tttagtaaa gttgtacctc ccctggatga agatggacgg
 781 agcttgttat cgcaaatgct gcactacgac cctaacaagc ggatttcggc caaggcagcc
 841 ctggctcacc ctttcttcca ggatgtgacc aagccagtac cccatcttcg actctgatag
 901 ccttcttgaa gccccccgacc ctaatcggct caccctctcc tccagtgtgg gcttgaccag
 961 cttggccttg ggctatttgg actcaggtgg gccctctgaa cttgccttaa acactcacct
1021 tctagtctta accagccaac tctgggaata caggggtgaa aggggggaac cagtgaaaat
1081 gaaaggaagt ttcagtatta gatgcactta agttagcctc caccaccctt tccccttct
1141 cttagttatt gctgaagagg gttggtataa aaataatttt aaaaaagcct tcctacacgt
1201 tagatttgcc gtaccaatct ctgaatgccc cataattatt atttccagtg tttgggatga
1261 ccaggatccc aagcctcctg ctgccacaat gtttataaag gccaaatgat agcgggggct
```

-continued

```
1321 aagttggtgc ttttgagaat taagtaaaac aaaaccactg ggaggagtct attttaaaga 1381 attcggttaa aaaatagatc caatcagttt atacccctagt tagtgttttc ctcacctaat 1441 aggctgggag actgaagact cagcccgggt gggggt
```

```
  1 MENFQKVEKIGEGTYGVVYKARNKLTGEVVALKKIRLDTETEGVPSTAIR                  (SEQ ID NO:14)

51 EISLLKELNHPNIVKLLDVIHTENKLYLVFEFLHQDLKKFMDASALTGIP

101 LPLIKSYLFQLLQGLAFCHSHRVLHRDLKPQNLLINTEGAIKLADFGLAR

151 AFGVPVRTYTHEVVTLWYRAPEILLGSKYYSTAVDIWSLGCIFAEMVTRR

201 ALFPGDSEIDQLFRIFRTLGTPDEVVWPGVTSMPDYKPSFPKWARQDFSK

251 VVPPLDEDGRSLLSQMLHYDPNKRIS AKAALAHPFFQDVTKPVPHLRL 299
```

(v) Nuclear Factor NF-90

The caHPSoxy-terminal region (starting at nucleotide 1930) of nuclear factor NF90 [GenBank Accession Number U10324; See e.g., Kao, et al., 1994. *J. Biol. Chem.* 269:20691–20699) was found to interact with the HPS protein, as disclosed in this invention. The nuclear factor of activated T cells (NFAT) has been shown to regulate gene expression of the lymphokine Interleukin-2 (IL-2) which is secreted following T-cell activation. See e.g., Marcoulato, et al., 1998. *J. Interferon Cytokine Res*. 18:351–355. The 90 and 45 Kdal subunits (i.e., NF90 and NF45) of NFAT specifically bind to the antigen receptor response element of the IL-2 promoter. NFAT is the nuclear-target of both T-cell stimulation signals and the immunosuppressant activity of the drugs cyclosporine and FK-506; whereas NF90 and NF45 are substrates for DNA-dependent protein kinase (DNA-PK) in vitro. In addition, recombinant NF90 has been found to promote the formation of a complex between the subunits of DNA-PK and DNA. See e.g., Lu, et al., 1998. *J. Biol. Chem*. 273:2136–2145. The nucleotide and amino acid sequences of a Nuclear Factor NF90 sequence provided in GenBank Accession Number U10324 is as follows:

```
    1 cgccgcctgc ccgcccgccc gctcgccccc ggtccggact cctcctcctc ctcttctcgc   (SEQ ID NO:15)

61 attgcagttg aacccagcag cccgccccac cggtggcttt tgggggcaga ccccggcggc 121 tgtggcagga gggcggcggc ggcggctgcg gtcgaagaag gggacgccga caagagttga 181 agtattgata acaccaagga actctatcac aatttgaaaa gataagcaaa agtttgattt 241 ccagacacta cagaagaagt aaaaatgcgt ccaatgcgaa tttttgtgaa tgatgaccgc 301 catgtgatgg caaagcattc ttccgtttat ccaacacaag aggagctgga ggcagtccag 361 aacatggtgt cccacacgga gcgggcgctc aaagctgtgt ccgactggat acacgagcag 421 gaaaagggta gcagcgagca ggcagagtcc gataacatgg atgtgccccc agaggacgac 481 agtaaagaag gggctgggga acagaagacg gagcacatga ccagaacctg tcggggagtg 541 atgcgggctg ggcctggtgg ccaaagtgcc tcctactcaa gggggacttg gatctggagc 601 tggtgctgct gtgtaaggag aagcccacaa ccggccctcc tggacaaggt ggccgacaac 661 ctggccatcc agcttgctgc tgtaacagaa gacaagtacg aaatactgca atctgtcgac 721 gatcctgcga ttgtgataaa aaacacaaaa gagcctccat tgtccctgac catccacctg 781 acatcccctg ttgtcagaga agaaatggag aaagtattag ctggagaaac gctatcagtc 841 aacgacccccc cggacgttct ggacaggcag aaatgctttg ctgccttggc gtccctccga 901 cacgccaagt ggttccaggc cagagccaac gggctgaagt cttgtgtcat tgtgatccgg 961 gtcttgaggg acctgtgcac tcgcgtgccc acctggggtc ccctccgagg ctggcctctc 1021 gagctcctgt gtgagaaatc cattggcacg gccaacagac cgatgggtgc tggcgaggcc 1081 ctgcggagag tgctggagtg cctggcgtcg ggcatcgtga tgccagatgg ttctggcatt 1141 tatgaccctt gtgaaaaaga agccactgat gctattgggc atctagacag acagcaacgg 1201 gaagatatca cacagagtgc gcagcacgca ctgcggctcg ccgcgttcgg ccagctccat 1261 aaagtcctag gcatggaccc tctgccttcc aagatgccca agaaaccaaa gaatgaaaac
```

-continued

```
1321 ccagtggact acaccgttca gatcccacca agcaccacct atgccattac gcccatgaaa
1381 cgcccaatgg aggaggacgg ggaggagaag tcgcccagca aaagaagaa gaagattcag
1441 aagaaagagg agaaggcaga gccccccag gctatgaatg ccctgatgcg gttgaaccag
1501 ctgaagccag ggctgcagta caagctggtg tcccagactg ggcccgtcca tgcccccatc
1561 tttaccatgt ctgtggaggt tgatggcaat tcattcgagg cctctgggcc ctccaaaaag
1621 acggccaagc tgcacgtggc cgttaaggtg ttacaggaca tgggcttgcc gacgggtgct
1681 gaaggcaggg actcgagcaa gggggaggac tcggctgagg agaccgaggc gaagccagca
1741 gtggtggccc ctgcccagt ggtagaagct gtctccaccc ctagtgcggc ctttccctca
1801 gatgccactg ccgagaacgt aaaacagcag gggccgatcc tgacaaagca cggcaagaac
1861 ccagtcatgg agctgaacga aagaggcgt gggctcaagt acgagctcat ctccgagacc
1921 gggggcagcc acgacaagcg cttcgtcatg gaggtcgaag tggatggaca aagttccaa
1981 ggtgctggtt ccaacaaaaa ggtggcgaag gcctacgctg ctcttgctgc ctagaaaag
2041 cttttccctg acacccctct ctcgcccttg atgccaacaa aaagaagaga gccccagtac
2101 ccgtcagagg gggaccgaaa tttgctgcta agccacataa ccctggcttc ggcatgggag
2161 gccccatgca caacgaagtg ccccacccc caaccttcg agggcgggga agaggcggga
2221 cgatccgggg acgagggcgc gggcgaggat ttggtggcgc caaccatgga ggctacatga
2281 atgccggtgc tgggtatgga agctatgggt acggaggcaa ctctgcgaca gcaggctaca
2341 gtcagttcta cagcaacgga gggcattctg gaatgccag tggcggtggc ggcggggggcg
2401 gtggtggctc ctccggctat ggctcctact accaaggtga caactacaac tcaccggtgc
2461 ccccaaaaca cgctgggaag aagcagccgc acggggccca gcagaagccc tcctacggct
2521 cgggctacca gtcccaccag ggccagcagc agtcctacaa ccagagcccc tacagcaact
2581 atggccctcc acagggcaag cagaaaggct ataaccatgg acaaggcagc tactcctact
2641 cgaactccta caactctccc ggggggggc gcggatccga ctacaactac gagagcaaat
2701 tcaactacag tggtagtgga ggccgaagcg gcgggaacag ctacgctca ggcggggcat
2761 cctacaaccc agggtcacac gggggctacg gcggaggttc tggggggcggc tcctcatacc
2821 aaggcaaaca aggaggctgc tcacagtcga actacagctc ccgggggtccg gccagaacta
2881 cagtggccct cccagctcct accagtcctc acaaggcggc tatggcagaa acgcagacca
2941 cagcatgaac taccagtaca gataagcccc gcgcggagat ttctaccttc tgcacttact
3001 ccccatcaga agatcgagtt ttatgcatca cagttaacat gtcagctgcc tgcgctccag
3061 gccccccgccc ccatcccgtc cacgttgctg tgtcgtgagg tgcagcgggt caccctgtgg
3121 cccgtcctgt gacccatatt tagccgtgtt tgggactccg tgtcttcaat ggtttgttag
3181 ttgccattac aactttgtct gggtagagtt tttgagtttt tgcagttcag tatccctctg
3241 tctattcaca cttcgtgtta gtggtaactc agtttgtctt taaatagtta cagaagggat
3301 acgtcatttg ttaatgcttt ttgttgaagt gagttaaacg agcttttctg tattttaatg
3361 ctttagtgtt tcagttttat aagtgaagat tttattttaa aaaccagtgg gaaagagtgg
3421 ggggtttctt tttatgtctg ggtcattcag gcagtacatc tgaattaagc tgaatgtaga
3481 caaataaaga aaaacaaaac tgaaa
```

```
  1 MRPMRIFVNDDRHVMAKHSSVYPTQEELEAVQNMVSHTERALKAVSDWIH                (SEQ ID NO:16)
 51 EQEKGSSEQAESDNMDVPPEDDSKEGAGEQKTEHMTRTCRGVMRAGPGGQ
101 SASYSRGTWIWSWCCCVRRSPQPALLDKVADNLAIQLAAVTEDKYEILQS
```

-continued

```
151 VDDAAIVIKNTKEPPLSLTIHLTSPVVREEMEKVLAGETLSVNDPPDVLD

201 RQKCFAALASLRHAKWFQARANGLKSCVIVIRVLRDLCTRVPTWGPLRGW

251 PLELLCEKSIGTANRPMGAGEALRRVLECLASGIVMPDGSGIYDPCEKEA

301 TDAIGHLDRQQREDITQSAQHALRLAAFGQLHKVLGMDPLPSKMPKKPKN

351 ENPVDYTVQIPPSTTYAITPMKRPMEEDGEEKSPSKKKKKIQKKEEKAEP

401 PQAMNALMRLNQLKPGLQYKLVSQTGPVHAPIFTMSVEVDGNSFEASGPS

451 KKTAKLHVAVKVLQDMGLPTGAEGRDSSKGEDSAEETEAKPAVVAPAPVV

501 EAVSTPSAAFPSDATAENVKQQGPILTKHGKNPVMELNEKRRGLKYELIS

551 ETGGSHDKRFVMEVEVDGQKFQGAGSNKKVAKAYAALAALEKLFPDTPLS

601 PLMPTKRREPQYPSEGDRNLLLSHITLASAWEAPCTTKCPHPPTFEGGEE

651 AGRSGDEGAGEDLVAPTMEAT
```

(B) Neurodegenerative and Developmental Disorder Proteins (i) Atroiphin-I

The caHPSoxy-terminal region (starting at nucleotide 2649) of atrophin-I (GenBank Accession Number U23851; Margolis, et al., 1996. *Brain Res. Mol. Brain Res.* 36:219–226) was found to interact with HPS protein, as disclosed in this invention. Interestingly, the same domain of atrophin-I was also found to interact with the LYST protein. Although the exact function of atrophin-1 is unknown, atrophin-I is the protein encoded by the gene involved in dentatorubral pallidoluysian atrophy (DRPLA; Smith's Disease), a rare, progressive and fatal autosomal dominant neurological disorder. DRPLA is characterized by neuronal degeneration, especially in the cerebellar dentate nucleus. Clinical symptomology include variable combinations of myoclonus epilepsy, cerebellar ataxia, choreoathetosis and dementia. DRPLA has been shown to result from the expansion of a CAG trinucleotide repeat encoding the amino acid glutamine. The DRPLA gene product has been primarily localized within the neuronal cytoplasm by in situ hybridization (see e.g., Yazawa, et al., 1995. *Nat. Genet.* 10:99–103) and it is wide-spread throughout the cerebral and cerebellar regions (see e.g., Knight, et al., 1997. *J. Neurol. Sci.* 146:19–26). The nucleotide and amino acid sequences of a Atrophin-I sequence provided in GenBank Accession Number U23851 is as follows:

```
   1 ttggggtgga gcagagaagt ttctgtattc agctgcccag gcagaggaga atggggtctc  (SEQ ID NO:17)

61 cacagcctga agaatgaaga cacgacagaa taaagactcg atgtcaatga ggagtggacg 121 gaagaaagag gccctgggc cccgggaaga actgagatcg aggggccggg cctcccctgg 181 aggggtcagc acgtccagca gtgatggcaa agctgagaag tccaggcaga cagccaagaa 241 ggcccgagta gaggaagcct ccaccccaaa ggtcaacaag cagggtcgga gtgaggagat 301 ctcagagagt gaaagtgagg agaccaatgc accaaaaaag accaaaactg aggaactccc 361 tcggccacag tctccctccg atctggatag cttggacggg cggagcctta atgatgatgg 421 cagcagcgac cctagggata tcgaccagga caaccgaagc acgtccccca gtatctacag 481 ccctggaagt gtggagaatg actctgactc atcttctggc ctgtcccagg gcccagcccg 541 cccctaccac ccacctccac tctttcctcc ttcccctcaa ccgccagaca gcacccctcg 601 acagccagag gctagctttg aacccatcc ttctgtgaca cccactggat atcatgctcc 661 catggagccc cccacatctc gaatgttcca ggctcctcct ggggcccctc ccctcaccc 721 acagctctat cccgggggca ctggtggagt tttgtctgga cccccaatgg gtcccaaggg 781 gggaggggct gcctcatcag tggggggccc taatgggggt aagcagcacc ccccacccac 841 tactcccatt tcagtatcaa gctctgggc tagtggtgct cccccaacaa agccgcctac 901 cactccagtg ggtggtggga acctaccttc tgctccacca ccagccaact tcccccatgt 961 gacaccgaac ctgcctcccc cacctgccct gagacccctc aacaatgcat cagcctctcc 1021 cctggcctg ggggcccaac cactacctgg tcatctgccc tctccccacg ccatgggaca
```

-continued

```
1081 gggtatcggt ggacttcctc ctggcccaga gaagggccca actctggctc cttcacccca
1141 ctctctgcct cctgcttcct cttctgctcc agcgcccccc atgaggtttc cttattcatc
1201 ctctagtagt agctctgcag cagcctcctc ttccagttct tcctcctctt cctctgcctc
1261 ccccttccca gcttcccagg cattgcccag ctaccccac tctttccctc ccccaacaag
1321 cctctctgtc tccaatcagc ccccaagta tactcagcct tctctcccat cccaggctgt
1381 gtggagccag ggtccccac cacctcctcc ctatggccgc ctcttagcca acagcaatgc
1441 ccatccaggc cccttccctc cctctactgg ggcccagtcc accgcccacc caccagtctc
1501 aacacatcac catcaccacc agcaacagca acagcagcag cagcagcagc agcagcagca
1561 gcatcacgga aactctgggc ccctcctcc tggagcattt ccccacccac tggagggcgg
1621 tagctcccac cacgcacacc cttacgccat gtctccctcc ctgggtctc tgaggcccta
1681 cccaccaggg ccagcacacc tgcccccacc tcacagccag gtgtcctaca gccaagcagg
1741 ccccaatggc cctccagtct cttcctcttc caactcttcc tcttccactt ctcaagggtc
1801 ctacccatgt tcacacccct ccccttccca gggccctcaa ggggcgccct acccttccc
1861 accggtgcct acgtcacca cctcttcggc taccctttcc acggtcattg ccaccgtggc
1921 ttcctcgcca gcaggctaca aaacggcctc cccacctggg ccccaccgt acggaaagag
1981 agccccgtcc ccgggggcct acaagacagc cacccaccc ggatacaaac ccgggtcgcc
2041 tccctccttc cgaacgggga ccccaccggg ctatcgagga acctcgccac ctgcaggccc
2101 agggaccttc aagccgggct cgcccaccgt gggacctggg ccctgccac ctgcggggcc
2161 ctcaggcctg ccatcgctgc caccaccacc tgcggcccct gcctcagggc cgcccctgag
2221 cgccacgcag atcaaacagg agccggctga ggagtatgag accccgaga gcccggtgcc
2281 cccagcccgc agccctcgc cccctcccaa ggtggtagat gtacccagcc atgccagtca
2341 gtctgccagg ttcaacaaac acctggatcg cggcttcaac tcgtgcgcgc gcagcgacct
2401 gtacttcgtg ccactggagg gctccaagct ggccaagaag cgggccgacc tggtggagaa
2461 ggtgcggcgc gaggccgagc agcgcgcgcg cgaagaaaag gagcgcgagc gcgagcggga
2521 acgcgagaaa gagcgcgagc gcgagaagga gcgcgagctt gaacgcagcg tgaagttggc
2581 tcaggagggc cgtgctccgg tggaatgccc atctctgggc ccagtgcccc atcgccctcc
2641 atttgaaccg ggcagtgcgg tggctacagt gcccccctac ctgggtcctg acactccagc
2701 cttgcgcact ctcagtgaat atgcccggcc tcatgtcatg tctcctggca atcgcaacca
2761 tccattctac gtgcccctgg gggcagtgga cccggggctc ctgggttaca atgtcccggc
2821 cctgtacagc agtgatccag ctgcccggga gagggaacgg gaagcccgtg aacgagacct
2881 ccgtgaccgc ctcaagcctg gctttgaggt gaagcctagt gagctggaac ccctacatgg
2941 ggtccctggg ccgggcttgg atccctttcc ccgacatggg ggcctggctc tgcagcctgg
3001 cccacctggc ctgcaccctt tccccttca tccgagcctg ggcccctgg agcgagaacg
3061 tctagcgctg gcagctgggc cagccctgcg gcctgacatg tcctatgctg agcggctggc
3121 agctgagagg cagcacgcag aaagggtggc ggccctgggc aatgacccac tggcccggct
3181 gcagatgctc aatgtgactc cccatcacca ccagcactcc cacatccact cgcacctgca
3241 cctgcaccag caagatgcta tccatgcagc ctctgcctcg gtgcaccctc tcattgaccc
3301 cctggcctca gggtctcacc ttacccggat cccctaccca gctggaactc ccctaacccc
3361 cctccttcct caccctctgc acgagaacga agttcttcgt caccagctct ttgctgcccc
3421 ttaccgggac ctgccggcct ccctttctgc cccgatgtca gcagctcatc agctgcaggc
```

-continued

```
3481 catgcacgca cagtcagctg agctgcagcg cttggcgctg gaacagcagc agtggctgca 3541 tgcccatcac ccgctgcaca gtgtgccgct gcctgcccag gaggactact acagtcacct 3601 gaagaaggaa agcgacaagc cactgtagaa cctgcgatca agagagcacc atggctccta 3661 cattggacct tggagcaccc ccaccctccc cccaccgtgc ccttggcctg ccacccagag 3721 ccaagagggt gctgctcagt tgcagggcct ccgcagctgg acagagagtg ggggagggag 3781 ggacagacag aaggccaagg cccgatgtgg tgtgcagagg tggggaggtg gcgaggatgg 3841 ggacagaaag cgcacagaat cttggaccag gtctctcttc cttgtccccc ctgcttttct 3901 cctcccccat gcccaacccc tgtggccgcc gcccctcccc tgcccgttg gtgtgattat 3961 ttcatctgtt agatgtggct gttttgcgta gcatcgtgtg ccaccctgc ccctcccga 4021 tccctgtgtg cgcgcccct ctgcaatgta tgccccttgc cccttcccca cactaataat 4081 ttatatatat aaatatctat atgacgctct taaaaaaaca tcccaaccaa aaccaaccaa 4141 acaaaaacat cctcacaact ccccagga
```

```
   1 METRQNKDSMSMRSGRKKEAPGPREELRSRGRASPGGVSTSSSDGKAEKS              (SEQ ID NO:18)

51 RQTAKKARVEEASTPKVNKQGRSEEISESESEETNAPKKTKTEELPRPQS

101 PSDLDSLDGRSLNDDGSSDPRDIDQDNRSTSPSIYSPGSVENDSDSSSGL

151 SQGPARPYHPPPLFPPSPQPPDSTPRQPEASFEPHPSVTPTGYHAPMEPP

201 TSRMFQAPPGAPPPHPQLYPGGTGGVLSGPPMGPKGGGAASSVGGPNGGK

251 QHPPPTTPISVSSSGASGAPPTKPPTTPVGGGNLPSAPPPANFPHVTPNL

301 PPPPALRPLNNASASPPGLGAQPLPGHLPSPHAMGQGIGGLPPGPEKGPT

351 LAPSPHSLPPASSSAPAPPMRFPYSSSSSSSAAASSSSSSSSSASPFPA

401 SQALPSYPHSFPPPTSLSVSNQPPKYTQPSLPSQAVWSQGPPPPPPYGRL

451 LANSNAHPGPFPPSTGAQSTAHPPVSTHHHHHQQQQQQQQQQQQQQHHGN

501 SGPPPPGAFPHPLEGGSSHHAHPYAMSPSLGSLRPYPPGPAHLPPPHSQV

551 SYSQAGPNGPPVSSSSNSSSSTSQGSYPCSHPSPSQGPQGAPYPFPPVPT

601 VTTSSATLSTVIATVASSPAGYKTASPPGPPPYGKRAPSPGAYKTATPPG

651 YKPGSPPSFRTGTPPGYRGTSPPAGPGTFKPGSPTVGPGPLPPAGPSGLP

701 SLPPPPAAPASGPPLSATQIKQEPAEEYETPESPVPPARSPSPPPKVVDV

751 PSHASQSARFNKHLDRGFNSCARSDLYFVPLEGSKLAKKRADLVEKVRRE

801 AEQRAREEKERERERERKEREREKERELERSVKLAQEGRAPVECPSLGP

851 VPHRPPFEPGSAVATVPPYLGPDTPALRTLSEYARPHVMSPGNRNHPFYV

901 PLGAVDPGLLGYNVPALYSSDPAARERREAREARERDLRDRLKPGFEVKPSE

951 LEPLHGVPGPGLDPFPRHGGLALQPGPPGLHPFPFHPSLGPLERERLALA

1001 AGPALRPDMSYAERLAAERQHAERVAALGNDPLARLQMLNVTPHHHQHSH

1051 IHSHLHLHQQDAIHAASASVHPLIDPLASGSHLTRIPYPAGTLPNPLLPH

1101 PLHENEVLRHQLFAAPYRDLPASLSAPMSAAHQLQAMHAQSAELQRLALE

1151 QQQWLHAHHPLHSVPLPAQEDYYSHLKKESDKPL
```

Atrophin-1 interacting proteins (AIPs) containing multiple WW domains were identified (see, e.g., Wood et al, 1998, *Mol. Cell. Neurosci.* 11:149–60). Two of these proteins are multidomain proteins containing a number of protein-protein interaction modules. The other three AIPs are highly homologous, each having four WW domains and a HECT domain characteristic of ubiquitin ligases.

(ii) DiGeorge Syndrome (DGS)-I Protein

A further HPS protein-IP disclosed herein is the DiGeorge Syndrome (DGS)-I protein (GenBank Accession Number L77566; see e.g., Gong, et al., 1996. *Hum. Mol. Genet.* 5:789–800). DGS-I was also identified as LYST interactant (see U.S. patent application Ser. No. 09/054,956; filed Apr. 3, 1998). One in 4,000 children is born with chromosome 22 deletion syndrome (DiGeorge syndrome), making it one of the most common genetic abnormalities in children. Patients with DiGeorge Syndrome possess deletions of the chromosomal region 22q11.2. The DGS-I gene has been localized to a DGS-critical region of chromosome 22 which encodes for a protein consisting of 476 amino acid residues. Clinical symptomology associated with DGS include cardiac defects, thymic hypoplasia cardiac defects, abnormal facial features, immune deficiencies, cleft palate and low blood calcium.

(C) HPS Protein-IPs Encoded by Novel Genes (i) HPIP1

One heretofore uncharacterized gene, referred to as HPIP1, has thus far been identified by the present invention disclosed herein. However, the translational products of the mRNA of these genes have not been defined and, thus no function has yet been assigned.

(ii) Human HN1 Homolog

Another heretofore uncharacterized human gene (referred to as HN1 homolog) was identified as the human homolog to mouse gene HN-1 (see Tang et al., 1997. *Mamm. Genome* 8:695–6). Murine Hn1 is expressed in many fetal and adult tissues. The highest levels of expression are found in hemopoietic cells, including day 10 yolk sac, blood islands-derived circulating erythroblasts, day 13 fetal liver, adult bone marrow and spleen. The expression is also very high in day 17 fetal brain, while the expression in adult brain is considerably lower. The nucleotide and amino acid sequences for the human homolog of murine HN-1 are disclosed by the present invention.

SUMMARY OF THE INVENTION

The present invention disclosed herein is based upon the novel finding that certain cellular proteins bind to, and form complexes with, the Hermansky-Pudlak Syndrome (HPS) protein. Accordingly, the present invention discloses protein complex compositions which are comprised of the HPS protein bound to (i.e., complexed with) a protein which recognizes and interacts with the HPS protein. It should be noted that a protein which forms a complex with HPS protein hereinafter will be designated an "HPS protein-IP" for HPS protein-Interacting Protein; and of the HPS protein and an HPS protein-IP hereinafter will be designated as "HPS protein•HPS protein-P complexes."

More specifically, the present invention is directed to complexes of HPS protein and complexes of the derivatives, fragments and/or analogs of HPS protein with HPIP1 and human HN1 homolog, as well as with the derivatives, fragments and/or analogs of these aforementioned HPS protein-IPs.

The present invention further discloses methodologies of screening for proteins which interact with the HPS protein or derivatives, fragments and/or analogs, thereof. Preferably, the method of screening is a yeast two-hybrid assay system, or a variation thereof.

The present invention further discloses the nucleotide and amino acid sequences of human HPIP1 (and homologs of other species) and of human HN1 homolog, as well as derivatives, fragments and analogs thereof. Nucleic acids which are complementary to (i.e., possess the ability to hybridize to), specific nucleotide sequences (e.g., the inverse complement of the foregoing sequences), are also provided. An inverse complement is a nucleic acid sequence which possesses a complementary sequence, running in reverse orientation to the coding strand, such that the inverse complement would hybridize without mismatches to the nucleic acid strand. Thus, for example, where the coding nucleic acid strand is hybridizable to a nucleic acid sequence with no mismatches between the coding strand and the hybridizable strand, then the inverse complement of the hybridizable strand is identical to the coding strand.

The present invention also discloses derivatives, fragments and/or analogs of HPIP1 and human HN1 homolog and which possess biological activity (i.e., they are capable of displaying one or more known functional activities of the wild-type HPIP1 or human HN1 homolog protein. Such biological activities include, but are not limited to: (i) the ability to bind to, or compete for interaction with, the HPS protein; (ii) antigenicity (i.e., the ability to bind to, or compete with, HPIP1 or human HN1 homolog for binding to an anti-HPIP1 or anti-human HN1 homolog antibody, respectively and (iii) immunogenicity (i.e., the ability to generate an antibody which is specific for, and binds to, HPIP1 and human HN1 homolog protein.

Methodologies for the production of the HPS protein•HPS protein-IP complex and of the HPIP1 and human HN1 homolog protein, and derivatives and analogs of these individual proteins and/or protein complexes (e.g., by recombinant means), are also disclosed. Pharmaceutical compositions comprising same are also provided herein.

The present invention further discloses methodologies for the modulation (i.e., the inhibition or enhancement) of the activity of HPS protein•HPS protein-IP complexes, and methods of modulating the HPIP1 and human HN1 homolog proteins. The individual protein components of these complexes have been implicated in various cellular functions, including but not limited to: physiological processes (e.g., vesicular transport, protein trafficking, pigmentation regulation, and platelet function) and pathological processes (e.g., oculocutaneous albinism, platelet dysfunction, neurodegenerative disease, and fibrotic lung disease).

In accord, the present invention also discloses methodologies for screening specific proteins or protein complexes including, but not limited to: (i) screening for the HPS protein•HPS protein-IP complex, the HPIP1 and human HN1 homolog proteins, as well derivatives and analogs of the HPS protein•HPS protein-IP complex; (ii) screening for HPIP1 and human HN1 homolog mRNA and (iii) screening the HPIP1 protein and human HN1 homolog for their ability to alter cell functions, particularly those cell functions in which the HPS protein and/or an HPS protein-IP have been implicated.

The present invention further discloses diagnostic and prognostic screening methodologies, as well as therapeutic and prophylactic compositions which are based upon: (i) HPS protein•HPS protein-IP complexes (including the nucleic acids encoding the individual proteins which participate in the formation of the complexes) and (ii) the HPIP1 protein and their encoding nucleic acid. Therapeutic compounds of the present invention include, but are not limited to: (i) HPS protein•HPS protein-IP complexes where one or both members of said complex is a derivative, fragment or analog of the HPS protein and/or an HPS protein-IP; (ii) HPIP1 protein and human HN1 homolog and derivatives, fragments or analogs thereof; (iii) antibodies to the protein or the derivatives, fragments or analogs thereof and (iv) nucleic acids encoding the aforementioned proteins, or their derivatives, fragments or analogs. Therapeutic compounds may also include the generation of antisense nucleic acids specific for the nucleotide sequences encoding both the HPS protein•HPS protein-IP components and the HPIP1 and human HN1 homolog protein. In addition, diagnostic, prognostic and screening kits are also disclosed herein.

Animal models and methodologies related to the screening of modulators (e.g., agonists, antagonists and inhibitors) of the biological activity of an HPS protein•HPS protein-IP complex, or of an HPIP1 protein, are also provided in the present invention. Similarly, methodologies related to the identification of molecules which inhibit or, alternatively, increase formation of HPS protein•HPS protein-IP complex complexes are also disclosed.

BRIEF DESCRIPTION OF THE FIGURES

In order that the present invention disclosed herein is better understood and appreciated, the following detailed description is set forth.

FIG. 1: illustrates the nucleic acid sequence [SEQ ID NO:1] and the inferred amino acid sequence [SEQ ID NO:2] of HPIP1.

FIG. 2: illustrates the nucleic acid sequence [SEQ ID NO:3] and the inferred amino acid sequence [SEQ ID NO:4] of human HN1 homolog (assembly hs2950_0). The amino acid residue occupying position 126 could be Met (ATG), Leu (TTG), Val (GTG), or Leu (CTG).

FIG. 3: a matrix of the results obtained from the yeast two-hybrid system assays demonstrating the specificity of HPS protein interactions. The results of assays which utilized the HPS protein as the bait proteins are indicated above the columns. The HPS protein was used in a forward (HPS protein) screen. The prey proteins 14-3-3 eta, Hrs, BMK1 alpha kinase, CDK2, Nuclear factor NF90, Atrophin-1, DGS-1, HPIP1, human HN1 homolog, retinoblastoma, p27 (Kip1), RGL-2 and vector control are indicated to the left of the columns. A positive interaction between the indicated bait and prey proteins is indicated as "+" sign in the box forming the intersection between the particular bait and prey proteins, a lack of interaction between the particular bait and prey proteins is designated as a "−" sign.

DETAILED DESCRIPTION OF THE INVENTION

In order that the present invention disclosed herein is better understood and appreciated, the following detailed description is set forth.

The present invention is based upon the identification of various proteins which interact with the Hermansky-Pudlak Syndrome (HPS) protein (hereinafter designated as "HPS protein-IPs") utilizing an improved, modified form of the yeast, two-hybrid system. The HPS protein-interacting proteins were demonstrated to form complexes under physiological conditions with HPS protein. Hereinafter the complexes of HPS protein with an HPS protein-IP will be designated as "HPS protein•HPS protein-IP complexes." These HPS protein•HPS protein-IP complexes, by virtue of this interaction, are implicated in the modulation of functional activities of the HPS protein and its associated binding partners.

The present invention is directed to methodologies for the screening of proteins which interact with (e.g., bind to) the HPS protein. The invention further relates to HPS protein complexes, in particular HPS protein complexes which contain the HPS protein-IPs disclosed in this invention. The present invention further relates to complexes of derivatives, analogs and fragments of the HPS protein with HPS protein-IPs, or derivatives, analogs and fragments thereof. In a preferred embodiment, such complexes bind an anti-HPS protein•HPS protein-IP antibody. Specifically, complexes of human HPS protein with a human HPS protein-IP protein are disclosed.

The present invention also provides methods of producing and/or isolating HPS protein•HPS protein-IP complexes. In a specific embodiment, the invention provides methods of using recombinant DNA techniques to express both HPS protein and its binding partner (or fragments, derivatives or homologs of one or both members of the complex) either where both binding partners are under the control of one heterologous promoter (i.e., a promoter not naturally associated with the native gene encoding the particular complex component) or where each is under the control of a separate heterologous promoter.

The present invention also provides the nucleotide sequence of the partial HPIP1 gene and of human HN1 homolog gene, respectively, and its respective, encoded amino acid sequences. The invention further relates to the carboxyl-terminal region of the HPIP1 protein and to the HN1 homolog protein, including derivatives, fragments, homologs or analogs thereof, as well as to the nucleic acid which encode the HPIP1 protein and HN1 homolog protein or its derivatives, fragments, homologs or analogs. The invention further provides for the HPIP1 protein and HN1 homolog protein and the nucleic acid sequences encoding these aforementioned proteins, from many different species, preferably from vertebrates, and more preferably from mammals. In the most preferred embodiment, the HPIP1 protein and HN1 homolog protein and genes are of human origin. Methodologies disclosing the production of the aforementioned protein, and their derivatives, fragments, homologs or analogs, are also provided in the present invention.

The present invention further relates to an HPIP1 and human HN1 homolog derivative or analog which is biologically active, that is, possessing one or more of the known functional activities associated with a full-length (wild-type) HPIP1 and human HN1 homolog proteins. Such biological activities include, but are not limited to: (i) the ability to bind to, or compete for interaction with, the HPS protein; (ii) antigenicity (i.e., the ability to bind to, or compete with, HPIP1 and human HN1 homolog for binding to an anti-HPIP1 and anti-human HN1 homolog antibody, respectively and (iii) immunogenicity (i.e., the ability to generate an antibody which is specific for, and binds to, HPIP1 protein and human HN1 homolog, respectively.

Methodologies relating to diagnosis and prognosis, as well as those methodologies involved in the screening for diseases and disorders associated with aberrant levels of an HPS protein•HPS protein-IP complex and/or HPIP1 and human HN1 homolog proteins, are provided. The present invention also provides methodologies related to treating or preventing diseases or disorders associated with: (i) aberrant levels of an HPS protein•HPS protein-IP complex; (ii) aberrant levels of the HPIP1 and human HN1 homolog proteins or (iii) aberrant biological activity levels of one or more of the components of the complex. These methodologies preferably comprise: (i) the administration of the HPS protein•HPS protein-IP complex; (ii) the administration of the HPIP1 and human HN1 homolog protein or (iii) administration of modulators of HPS protein•HPS protein-IP complex formation or activity (e.g., antibodies which bind the HPS protein•HPS protein-IP complex, non-complexed HPS protein, or their binding partner or a fragment thereof— preferably the fragment containing the portion of HPS protein or the HPS protein-IP which is directly involved in complex formation). Methodologies disclosed herein also include, but are not limited to, the administration of: (i) mutants of the HPS protein or the HPS protein-IPs which either increase or decrease binding affinity; (ii) small-molecule inhibitors or enhancers of protein complex formation or (iii) antibodies which either stabilize or neutralize the protein complex.

In order to quantitatively assess biological activity for utilization in therapeutics or diagnostics, methodologies related to the detection of HPS protein•HPS protein-IP complexes, HPIP1 and human HN1 homolog proteins, or modulators (i.e., inhibitors, agonists and antagonists) thereof, are also provided.

(1) HPS Protein•HPS Protein-IP Complexes and HPIP1 and Human HN1 Homolog Proteins As previously discussed, the present invention relates to HPS protein•HPS protein-IP complexes. In a preferred embodiment, the HPS protein•HPS protein-IP complex is comprised of human proteins.

The present invention also relates to complexes which are comprised of: (i) derivatives, fragments and analogs of the HPS protein interacting with an HPS protein-IP; (ii) the HPS protein interacting with derivatives, fragments and analogs of a HPS protein-IP and (iii) derivatives, fragments and analogs of the HPS protein interacting with derivatives, fragments and analogs of a HPS protein-IP. Accordingly, the present invention provides methodologies for the screening of HPS protein•HPS protein-IP complexes, the HPIP1 and human HN1 homolog proteins, and their various derivatives, fragments and analogs for the ability to alter cell functions, particularly those cell functions in which the HPS protein and/or a HPS protein-IP has been implicated. Such functions include, but are not limited to, physiological processes (e.g., vesicular transport, protein trafficking, pigmentation regulation, and platelet function) and pathological processes (e.g., oculocutaneous albinism, platelet dysfunction, neurodegenerative disease and fibrotic lung disease.

In addition to the ability to alter cellular functions, other functions of these protein complexes include, but are not limited to: binding to an anti-HPS protein•HPS protein-IP complex antibody, as well as other activities as described in the art. For example, derivatives or analogs of the HPS protein•HPS protein-IP complex which have the desired immunogenicity or antigenicity can be used in immunoassays, for immunization, for inhibition of HPS protein•HPS protein-IP complex activity, and the like. Derivatives or analogs of the HPS protein•HPS protein-IP complex which retain or enhance, or alternatively lack or inhibit, a property of interest (e.g., participation in an HPS protein•HPS protein-IP complex), can be used as inducers, or inhibitors, respectively, of such a property and its physiological correlates. A specific embodiment relates to an HPS protein•HPS protein-IP complex of a fragment of the HPS protein and/or a fragment of a HPS protein-IP protein which can be bound by an anti-HPS protein, an anti-HPS protein-IP antibody, or by an antibody specific for a HPS protein•HPS protein-IP complex, when such fragment is included within an HPS protein•HPS protein-IP complex.

The present invention further relates to the HPIP1 and human HN1 homolog protein, as well as their derivatives, homologs and analogs. The native protein, fragment, derivative or analog of the HPIP1 and human HN1 homolog protein may be derived from a variety of sources including, but not limited to: human, mouse, rat, pig, cow, dog, monkey, fly, frog, or plant.

The nucleotide sequences which encode the human HPS protein, 14-3-3 eta, Hrs, BMK1 alpha kinase, CDK2, Nuclear factor NF90, Atrophin-1, and DGS-1 are known. The nucleic acids which encode the HPS protein and the HPS protein-IP s may be obtained by any method known in the art (e.g., by PCR amplification using synthetic primers hybridizable to the 3'- and 5'-termini of the sequence or by cloning from a cDNA or genomic library using an oligonucleotide specific for the gene sequence). Homologs (i.e., nucleic acids encoding HPS protein or HPS protein-IPs derived from species other than human) or other related sequences (e.g., paralogs) may be obtained by utilization of all or a portion of the particular human nucleotide sequence as a probe under low, moderate or high stringency hybridization conditions, followed by cloning.

The HPS protein and HPS protein-IPs, either alone or in a complex, may be obtained by methods well known in the art for protein purification and in vitro transcription/translation. The expression of one or more of the aforementioned proteins may be facilitated by the insertion of the nucleic acid containing all or a portion of the nucleotide sequence encoding the protein of interest into an appropriate expression vector (i.e., a vector which possesses the necessary elements for the transcription and translation of the inserted protein coding sequence). Additionally, the necessary transcriptional and translational signals may also be supplied by the native promoter for the HPS protein, any HPS protein-IP gene, or their flanking regions. A variety of host-vector systems may be utilized to express the protein coding sequence. These include, but are not limited to: (i) mammalian cell systems infected with virus (e.g., vaccinia virus, adenovirus, etc.); (ii) insect cell systems infected with virus (e.g., baculovirus); (iii) yeast containing yeast vectors or (iv) bacteria transformed with bacteriophage DNA, plasmid DNA, or cosmid DNA. The associated expression elements of these vectors vary in their strengths and specificities.

In a preferred embodiment, an HPS protein•HPS protein-IP complex is obtained by expressing the entire HPS protein sequence and an HPS protein-IP coding sequence within the same cell, either under the control of the same promoter or under two separate promoters. In another embodiment, a derivative, fragment or homolog of the HPS protein and/or a derivative, fragment or homolog of an HPS protein-IP are recombinantly expressed. Preferably the derivative, fragment or homolog of the HPS protein or of the HPS protein-IP protein forms a complex with a binding partner identified by a binding assay (e.g., a modified yeast two-hybrid system) and, more preferably, forms a complex which also binds to an anti-HPS protein•HPS protein-IP complex antibody.

Any of the methodologies known in the art for the insertion of DNA fragments into a vector may be utilized to construct expression vectors containing a chimeric gene possessing not only a protein coding sequence but the appropriate transcriptional/translational control signals. These methods may include in vitro recombinant DNA and synthetic techniques and in vivo recombinants (genetic recombination). Expression of nucleotide sequences encoding the HPS protein and an HPS protein-IP may be regulated by a second nucleotide sequence so that the gene or gene fragment thereof is expressed in a host transformed with the recombinant DNA molecule(s) of interest.

Expression of the proteins may be controlled by any promoter/enhancer known in the art. Promoters which may be utilized include, but are not limited to: (i) the SV40 early promoter (see e.g., Bernoist & Chambon, 1981. *Nature* 290:304–310); (ii) the promoter contained in the 3'-terminus long terminal repeat of Rous Sarcoma Virus (see e.g., Yamamoto, et al., 1980. *Cell* 22:787–797); (iii) the Herpes Simplex Virus thymidine kinase promoter (see e.g., Wagner, et al., 1981. *Proc. Natl. Acad. Sci. USA* 78:1441–1445); (iv)

the regulatory sequences of the metallothionein gene (Brinster, et al., 1982. *Nature* 296:39–42); (v) prokaryotic expression vectors such as the B-lactamase promoter (see e.g., Villa-Kamaroff, et al., 1978. *Proc. Natl. Acad. Sci. USA* 75:3727–3731) or the tac promoter (see e.g., DeBoer, et al., 1983. *Proc. Natl. Acad. Sci. USA* 80:21–25); (vi) plant expression vectors comprising the nopaline synthetase promoter (see e.g., Herrar-Estrella, et al., 1984. *Nature* 303:209–213) or the Cauliflower Mosaic Virus 35S RNA promoter (see e.g., Garder, et al., 1981. *Nuc. Acids Res.* 9:2871–2879); (vii) the promoter of the photosynthetic enzyme ribulose bisphosphate caHPSoxylase (see e.g., Herrera-Estrella, et al., 1984. *Nature* 310:115–120); (viii) promoter elements from yeast and other fungi such as the Gal4 promoter, the alcohol dehydrogenase promoter, the phosphoglycerol kinase promoter, the alkaline phosphatase promoter and (ix) animal transcriptional control regions which exhibit tissue specificity and have been utilized in transgenic animals such as the elastase I gene control region which is active in pancreatic acinar cells (see e.g., Swift, et al., 1984. *Cell* 38:639–646).

In a preferred embodiment of the present invention, a vector is utilized which comprises a promoter operably-linked to nucleotide sequences encoding the HPS protein and/or an HPS protein-IP or a fragment, derivative or homolog thereof, one or more origins of replication and, optionally, one or more selectable markers (e.g., an antibiotic resistance gene). In another preferred embodiment, an expression vector containing the coding sequence, or a portion thereof, of the HPS protein and an HPS protein-IP, either together or separately, is made by subcloning the aforementioned gene sequences into the EcoRi restriction site of one of the commercially-available pGEX vectors (glutathione S-transferase expression vectors; Promega Corp.; Madison, Wis.) See e.g., Smith & Johnson, 1988. *Gene* 7:31–40. This allows for the expression of gene products in the correct reading frame.

Expression vectors which contain the nucleic acid sequences of interest may be identified by three general methodologies: (i) nucleic acid hybridization; (ii) presence or absence of marker gene function and (iii) expression of the inserted sequences. In the first methodology, the HPS protein or HPS protein-IP sequences are detected by nucleic acid hybridization with probes possessing sequences homologous and complementary to the inserted sequences. In the second methodology, the recombinant vector host system may be identified and selected based upon the presence or absence of certain marker functions (e.g., binding to an anti-HPS protein, anti-HPS-IP, or anti-HPS protein•HPS protein-IP complex antibody; resistance to antibiotics, occlusion body formation in baculovirus, or the like) caused by insertion of the sequences of interest into the vector. In the third methodology, recombinant expression vectors may be identified by assaying for the HPS protein or HPS protein-IP products expressed by the recombinant vector. Such assays may be based on, for example, the physical or functional properties of the interacting species in in vitro assay systems (e.g., the formation of an HPS protein•HPS protein-IP complex or immunoreactivity to antibodies specific for the protein).

Once the recombinant protein molecules are identified and the complexes or individual proteins are isolated, numerous methods known in the art may be used to propagate/amplify them. In addition, a host cell strain may be chosen which serves to modulate the expression of the inserted sequence, or which modifies or processes the expressed protein in the specific manner desired. Expression from certain promoters may be elevated in the presence of certain inducers, thus controlling the expression of the genetically-engineered HPS protein and/or HPS protein-IP. Furthermore, different host cells have characteristic and specific mechanisms for the translational and post-translational processing and modification (e.g., glycosylation, phosphorylation, etc.) of proteins.

In other preferred embodiments, the HPS protein and/or HPS protein-IP, or fragment, homolog or derivative thereof, may be expressed as a fusion or chimeric protein product which is comprised of the protein joined via a peptide bond to a heterologous protein sequence of a different protein. Such chimeric products may be generated by ligation of the appropriate nucleic acid sequences encoding the desired amino acids to each one another in the proper reading frame and expressing the chimeric products in a suitable host by methods well known in the art. Alternatively, such chimeric products may be generated by protein synthetic techniques (e.g., by use of a peptide synthesizer) wherein chimeric genes comprising portions of the HPS protein and/or an HPS protein-IP fused to any heterologous protein-encoding sequences may be constructed. A specific embodiment relates to a chimeric protein comprising a fragment of the HPS protein and/or an HPS protein-IP of at least six amino acids.

In a preferred embodiment disclosed herein, fusion proteins are generated which contain the interacting domains of the HPS protein and an HPS protein-IP and/or, optionally, a hetero-functional reagent, such as a peptide linker between the two domains, wherein the utilization of the hetero-functional reagent promotes the interaction of the HPS protein and HPS protein-IP binding domains. These fusion proteins may be particularly useful where thermodynamic stability of the interaction is desirable (e.g., in production of antibodies specific to the HPS protein•HPS protein-IP complex). Additionally, HPS protein and/or HPS protein-IPs derivatives may be generated by altering their respective sequence by the utilization of conservative substitutions, additions or deletions which provide for functionally equivalent molecules. Due to the degeneracy of nucleotide coding sequences, other DNA sequences which encode substantially the same amino acid sequence as the HPS protein or HPS protein-IP genes may be used in the practice of the present invention. In a specific embodiment of the present invention, proteins consisting of at least 6 (contiguous) amino acids of the HPS protein or an HPS protein-IP are provided. In other embodiments, the fragment consists of at least about 10, 20, 30, 40, or 50 contiguous amino acids of the HPS protein or an HPS protein-IP.

The HPS protein or HPS protein-IP derivatives and analogs of the invention may be produced by various methods known in the art. The manipulations which result in their production may occur at either the gene or protein level. For example, the cloned HPS protein or HPS protein-IP gene sequence can be modified by any of numerous strategies known in the art (see e.g., Sambrook, et al., 1989. *Molecular Cloning, A Laboratory Manual*, 2d Ed., Cold Spring Harbor Laboratory Press, Cold Spring Harbor, N.Y.). The sequences can then be cleaved at appropriate sites with restriction endonuclease(s), isolated, and ligated in vitro. Additionally, the HPS protein and/or HPS protein-IP-encoding nucleotide sequence may be mutated in vitro or in vivo, so as to: (i) create and/or destroy translation, initiation, and/or termination sequences or (ii) create variations in coding regions and/or form new restriction endonuclease sites or destroy pre-existing ones, to facilitate further in vitro modification. Any technique for mutagenesis known in the art may be used, including, but not limited to, chemical mutagenesis and in vitro site-directed mutagenesis (see e.g., Hutchinson, et al., 1978. *J. Biol. Chem.* 253:6551–6558); use of TAB™ Linkers (Pharmacia; Upsala, Sweden), and the like.

Once the recombinant cell expressing the HPS protein and/or an HPS protein-IP protein, or fragment or derivative thereof, is identified, the individual gene product or complex may be isolated and analyzed. This is facilitated through the use of assays based upon the physical and/or functional properties of the protein or complex, including, but not limited to, radioactive labeling of the product followed by gel electrophoresis analysis, immunoassay, cross-linking to marker-labeled product, and the like.

The HPS protein•HPS protein-IP complex or HPIP1 and human HN1 homolog protein, may be isolated and purified by standard methodologies known in the art (either from natural sources or recombinant host cells expressing the complexes or proteins), including but not limited to: (i) column chromatography (e.g., ion exchange, affinity, gel exclusion, reversed-phase high pressure, fast protein liquid, etc); (ii) differential centrifugation; (iii) differential solubility or by any other standard technique utilized for the purification of proteins. Additionally, biological functionality may be evaluated using any suitable assay known in the art. Alternatively, once an HPS protein-IP or its derivative is identified, the amino acid sequence of the protein can be deduced from the nucleotide sequence of the chimeric gene from which it was encoded. As a result, the protein (or its derivative) may be synthesized by standard chemical methods known in the art. See e.g., Hunkapiller, et al., 1984. *Nature* 310: 105–111.

Manipulations of the HPS protein and/or HPS protein-IP sequences may be made at the protein level. Included within the scope of the invention are derivatives of complexes of the HPS protein, an HPS protein-IP, or fragments, derivatives or analogs thereof, that are differentially modified during or after translation (e.g., by glycosylation, acetylation, phosphorylation, amidation, derivatization by known protecting/blocking groups, proteolytic cleavage, linkage to an antibody molecule or other cellular ligand, etc). Any of numerous chemical modifications may be carried out by known techniques including, but not limited to, specific chemical cleavage by cyanogen bromide, trypsin, chymotrypsin, papain, V8 protease, $NaBH_4$, acetylation, formylation, oxidation, reduction, metabolic synthesis in the presence of tunicamycin, and the like.

In a specific embodiment, the HPS protein and/or HPS protein-IP sequences are modified to include a fluorescent label. In another specific embodiment, the HPS protein and/or the HPS protein-IP are modified to include a heterofunctional reagent, which can be used to cross-link the protein to other members of the complex or to other HPS protein-IPs. In addition, analogs and derivatives of the HPS protein, an HPS protein-IP, or their analogs and derivatives can be chemically synthesized. For example, a peptide corresponding to a portion of the HPS protein and/or an HPS protein-IP which either comprises the desired domain or mediates the desired activity in vitro (e.g., HPS protein•HPS protein-IP complex formation) may be synthesized by use of a peptide synthesizer. Furthermore, if so desired, non-classical amino acids or chemical amino acid analogs may be introduced as a substitution or addition into the HPS protein and/or an HPS protein-IP.

In addition to standard sequencing techniques, the HPS protein•HPS protein-IP complex or HPIP1 and human HN1 homolog proteins may be analyzed by hydrophilicity analysis. See e.g., Hopp & Woods, 1981. *Proc. Natl. Acad. Sci. USA* 78:3824–3828. Secondary structural analysis can also be done to identify regions of the HPS protein and/or a HPS protein-IP that assume specific structures. See e.g., Chou & Fasman, 1974. *Biochemistry* 13:222–223. The methodologies of manipulation, translation, secondary structure prediction, hydrophilicity and hydrophobicity profiles, open reading frame prediction and plotting, and determination of sequence homologies, can all be accomplished using computer software programs currently available in the art. Other methods of structural analysis include, but are not limited to: X-ray crystallography (see e.g., Engstrom, 1974. *Biochem. Exp. Biol.* 11:7–13); mass spectroscopy and gas chromatography (see e.g., *Methods in Protein Science*, J. Wiley and Sons, New York, 1997) and computer modeling (see e.g., Fletterick & Zoller, eds., 1986. Computer Graphics and Molecular Modeling, In: *Current Communications in Molecular Biology*, Cold Spring Harbor Laboratory Press, Cold Spring Harbor, N.Y.) may also be employed.

(2) Identification and Isolation of the Gene Encoding the HPIP1 and Human HN1 Homolog Protein The present invention discloses the nucleotide sequences which encode the HPIP1, and human HN1 homolog proteins. In specific embodiments, the HPIP1 and human HN1 homolog nucleic acid sequence comprises the sequence of SEQ ID NOS: 1 and 3, respectively, or a portion thereof, or a nucleotide sequence encoding, in whole or in part, an HPIP1 and human HN1 homolog protein (e.g., a protein comprising the amino acid sequence of SEQ ID NOS: 2 and 4, respectively, or a portion thereof). The present invention also provides purified nucleic acids consisting of at least 8 nucleotides (i.e., a hybridizable portion) of an HPIP1 and human HN1 homolog sequence. In other embodiments, the nucleic acids consist of at least about 25 (contiguous) nucleotides, 50 nucleotides, 100 nucleotides, 150 nucleotides, or 200 nucleotides of a HPIP1 and human HN1 homolog gene sequence, or a full-length HPIP1 and human HN1 homolog gene sequence. In yet another embodiment, the nucleic acids are smaller than 35, 200 or 500 nucleotides in length. The nucleic acids may be single or double stranded.

The present invention also relates to nucleic acids which are hybridizable or complementary to the aforementioned nucleic acid sequences, in particular, the invention provides the inverse complement to nucleic acids which are hybridizable to the aforementioned sequences. More specifically, the inverse complement of a nucleic acid strand has the complementary sequence running in reverse orientation to the strand so that the inverse complement would hybridize without mismatches to the nucleic acid strand. In a preferred embodiment, nucleic acids are generated which comprise a sequence complementary to (specifically are the inverse complement of) at least about 10, 25, 50, 100, or 200 nucleotides or the entire coding region of an HPIP1 and human HN1 homolog gene.

In a specific, preferred embodiment of the present invention, a nucleic acid which is hybridizable to an HPIP1 and human HN1 homolog nucleic acid sequence (e.g., possessing the sequence set forth in SEQ ID NOS: 1 and 3, respectively), or to a nucleic acid sequence encoding an HPIP1 and human HN1 homolog protein derivative (or a complement thereof), under conditions of low stringency, is disclosed. By way of example and not of limitation, the procedure utilizing conditions of low, moderate or high stringency can be as described, see e.g., Shilo & Weinberg, 1981. *Proc. Natl. Acad. Sci. USA* 78:6789–6792. It should be noted that other conditions of low, moderate or high stringency hybridization (e.g., as employed for cross-species hybridizations) are well known within the art and may be utilized.

Nucleic acid molecules which encode derivatives and analogs of HPIP1 and human HN1 homolog protein, or HPIP1 and human HN1 homolog antisense nucleic acids, are additionally disclosed. As is readily apparent for its use herein, a "nucleic acid encoding a fragment or portion of an HPIP1 and human HN1 homolog protein" shall be construed as referring to a nucleic acid encoding only the recited fragment or portion of the HPIP1 and human HN1 homolog protein, and not the other contiguous portions of the HPIP1 and human HN1 homolog as a continuous sequence.

Within a given nucleotide sequence, potential open reading frames (ORFs) can be identified using the NCBI BLAST ORF Finder computer program which is currently commercially available. Due to the fact that all known protein translation products are at least 60 amino acids or longer (see e.g., Creighton, 1992. *Proteins*, 2$^{nd}$ Ed., W. H. Freeman and Co., New York, N.Y.), only those ORFs potentially encoding a protein of 60 amino acids or more were considered. The nucleic acid sequence encoding HPIP1 possesses a stop codon. The ORF encoding HPIP1 (nucleotide 1 to 519, 173 amino acids) putatively predicts the carboxyl-terminal of a longer protein. The ORF encoding human HN1 homolog (nucleotide 106 to 564–153 amino acid reading frame, starting with a methionine start codon and ending with a stop codon) predicts a protein of 153 amino acids, with a calculated molecular weight of 15946.4.

Any methodology available within the art may be utilized to obtain a full-length (i.e., encompassing the entire coding region) cDNA clone encoding an HPIP1 and human HN1 homolog protein. In particular, the polymerase chain reaction (PCR) can be utilized to amplify sequences in silico from a cDNA library. Oligonucleotide primers which hybridize to sequences at the 3'- and 5'-termini of the identified sequences may be used as primers to facilitate amplification by PCR those sequences of interest from a nucleic acid sample (cDNA or DNA), preferably a cDNA library, from an appropriate source (e.g., the sample from which the initial cDNA library for the modified yeast two-hybrid assay fusion population was derived). For example, PCR may be carried out through use of a Perkin-Elmer Cetus Thermal Cycler and Taq polymerase. The DNA being amplified may include genomic DNA or cDNA sequences obtained from any eukaryotic species. One can choose to synthesize several different degenerate primers, for use in the PCR reactions and it is also possible to vary the stringency of hybridization conditions used in priming the PCR reactions, to amplify nucleic acid homologs (e.g., to obtain HPIP1 and human HN1 homolog protein sequences from species other than humans, or to obtain human sequences with homology to HPIP1 and human HN1 homolog protein ) by allowing for greater or lesser degrees of nucleotide sequence homology between the known nucleotide sequence and the nucleic acid homolog being isolated. For cross species hybridization, low stringency conditions are generally preferred. In contrast, for same species hybridization, moderately stringent conditions are generally preferred.

Following successful amplification of the nucleic acid which contained all or a portion of the HPIP1 and human HN1 homolog protein sequences, those amplified sequence may be subsequently cloned and sequenced, and, if desired, utilized as a probe to isolate a complete cDNA or genomic clone. This, in turn, permits the determination of the gene's complete nucleotide sequence, the analysis of its expression, and the production of its protein product for functional analysis. In this manner, the nucleotide sequences of HPIP1 and human HN1 homolog protein were identified.

Any eukaryotic cell potentially can serve as the nucleic acid source for the cloning of the HPIP1 and human HN1 homolog protein genes. The DNA may be obtained by standard procedures known in the art from cloned DNA (e.g., a DNA "library"), by chemical synthesis, by cDNA cloning or by the cloning of genomic DNA, or fragments thereof, purified from the desired cell (see e.g., Sambrook, et al., 1989. *Molecular Cloning, A Laboratory Manual*, 2d Ed., Cold Spring Harbor Laboratory Press, Cold Spring Harbor, N.Y.); 1985. DNA *Cloning: A Practical Approach*, MRL Press, Ltd., Oxford, U.K., Vols. I & II). Clones derived from genomic DNA may contain regulatory and intronic DNA regions in addition to the coding exonic regions; whereas clones derived from cDNA will contain only exonic sequences.

In the cloning of a sequence of interest (i.e., a gene) from genomic DNA, DNA fragments may are generated by numerous methodologies which are well-known within the art. These methodologies include, but are not limited to: (i) cleavage of the DNA at specific sites using one or more restriction endonucleases, (ii) fragmentation of the DNA by use of DNase in the presence of manganese or (iii) physically shearing of the DNA by, for example, sonication. The linear, double-stranded DNA fragments may then be separated as a function of size by standard techniques, including but not limited to, agarose and/or polyacrylamide gel electrophoresis, gradient ultracentrifugation or column chromatography.

Once the DNA fragments have been generated, identification of the specific DNA fragment containing the desired gene may be accomplished in a variety of ways. For example, a portion of the HPIP1 gene and human HN1 homolog protein (generated by, for example, PCR amplification or an oligonucleotide having a sequence of a portion of the known nucleotide sequence) or its specific mRNA, or a fragment or derivative thereof, may be purified and labeled, and the generated DNA fragments may then be screened by nucleic acid hybridization to the labeled probe molecule (see e.g., Benton & Davis, 1977. *Science* 196:180–182; Grunstein & Hogness, 1975. *Proc. Natl. Acad. Sci. U.S.A.* 72:3961–3964). It is also possible to identify the appropriate fragment by restriction enzyme digestion(s) and comparison of fragment sizes with those expected according to a known restriction map if such is available, or by DNA sequence analysis and comparison to the known nucleotide sequence of HPIP1 and human HN1 homolog protein. Further selection may be performed on the basis of the specific properties of the gene of interest or, alternately, its expressed gene product through assays based upon the physical, chemical, or immunological properties of said product. For example, cDNA clones, or DNA clones which hybrid-select the proper mRNAs, may be selected on the basis of specific protein production (i.e., selection of those clones which produce a protein producing similar or identical electrophoretic migration, isoelectric focusing behavior, proteolytic digestion maps, antigenic properties or ability to bind the HPS protein, as has been demonstrated for HPIP1 and human HN1 homolog protein. In addition, clones putatively producing the HPIP1 protein may be identified by the binding of a labeled antibody (specific for HPIP1 and human HN1 homolog protein) to the putatively clone(s), in an ELISA (enzyme-linked immunosorbent assay)-type procedure. An alternative methodology to the isolation of an HPIP1 and human HN1 homolog protein cDNA, includes, but is not limited to, chemically synthesizing the gene sequence itself from a known sequence. Other methods are possible and within the scope of the invention.

Subsequently, the identified and isolated nucleic acids may then be ligated into an appropriate cloning vector. A large number of vector-host systems are known within the art. Examples of vectors which may be utilized in the present invention include, but are not limited to: bacteriophage vectors (e.g., lambda derivatives) or bacterial or yeast plasmids (e.g., pBR322). The insertion of the DNA fragment of interest into a cloning vector may be accomplished by the utilization of a variety of methods including, but not limited to: (i) the use of complementary cohesive termini; (ii) the use of an enzyme (Klenow fragment of DNA polymerase I to make the insert termini "blunt-ended" (iii) the use of "linker" nucleotide sequences (e.g., specific, chemically-synthesized oligonucleotides possessing, for example, RE sequences) ligated to the termini of the insert DNA fragment or (iv) the use of complementary, homopolymeric tailing of both the vector and DNA insert. etc.

To facilitate the production of numerous copies of the gene sequence of interest, the recombinant molecules are then be introduced into host cells by, for example, transformation, transfection, infection, electroporation, and the like. In an alternative method, the desired gene may be identified and isolated in a "shotgun" cloning approach whereby the gene of interest is enriched by, for example, size fractionation, prior to its insertion into a suitable cloning vector. In the present invention, specific preferred embodiments, enable the generation of large quantities of the nucleic acid of interest by transformation of host cells with: (i) recombinant DNA molecules which possess sequences (i.e., the gene) encoding HPIP1 and human HN1 homolog protein; (ii) an HPIP1 and human HN1 homolog protein cDNA or (iii) a chemically-synthesized DNA sequence.

It should be noted that the HPIP1 and human HN1 homolog protein nucleic acid sequences provided by the present invention includes those nucleotide sequences which encode: (i) substantially the same amino acid sequence as found within the native HPIP1 and human HN1 homolog protein; (ii) amino acid sequences possessing functionally-equivalent amino acid substitutions and (iii) other HPIP1 and human HN1 homolog protein derivatives, fragments or analogs.

(3) Antibodies Specific for the HPS Protein•HPS Protein-IP Complex and HPIP1 and Human HN1 Homolog Protein Proteins As disclosed by the present invention herein, the HPS protein•HPS protein-IP complex or fragments, derivatives, analogs or homologs thereof, or the HPIP1 and human HN1 homolog protein, or fragments, derivatives, analogs or homologs thereof, may be utilized as immunogens to generate antibodies which immunospecifically-bind these aforementioned immunogenic molecules. Such antibodies include, but are not limited to: polyclonal, monoclonal, chimeric, and single-chain antibodies, $F_{ab}$ fragments, and $F_{ab}$ expression libraries. In a preferred embodiment, antibodies specific for complexes of the human HPS protein and a human HPS protein-IP are generated. Various methodologies known within the art may be utilized for the production of polyclonal antibodies to a HPS protein•HPS protein-IP complex, or to a derivative, homolog or analog thereof, or to HPIP1 and human HN1 homolog protein, or a derivative, fragment, homolog or analog thereof. For production of the antibody, various host animals can be immunized by injection with the native HPS protein•HPS protein-IP complex, the HPIP1 and human HN1 homolog protein, or a synthetic version or derivative thereof (e.g., a cross-linked HPS protein/HPS protein-IP For preparation of monoclonal antibodies directed towards an HPS protein•HPS protein-IP complex, to HPIP1 and human HN1 homolog protein, or derivatives, fragments, homologs or analogs thereof, any methodology which provides for the production of antibody molecules by continuous in vitro cell line culture may be utilized. Such methodologies include, but are not limited to: (i) the hybridoma technique (see Kohler & Milstein, 1975. *Nature* 256:495–497); (ii) the trioma technique (see Rosen, et al., 1977. *Cell* 11:139–147); (iii) the human B-cell hybridoma technique (see Kozbor, et al., 1983. *Immunol. Today* 4:7284) and (iv) the EBV hybridoma technique utilized to produce human monoclonal antibodies (see Cole, et al., 1985. In: *Monoclonal Antibodies and Cancer Therapy* (Alan R. Liss, Inc., pp. 77–96)).

In a preferred embodiment of the present invention, human monoclonal antibodies obtained by using human hybridomas (see e.g., Cole, et al., 1983. *Proc. Natl. Acad. Sci. USA* 80:2026–2030) or by the transformation of human B-cells with Epstein-Barr Virus (EBV) in vitro (see e.g., Cole, et al., 1985. In: *Monoclonal Antibodies and Cancer Therapy* (Alan R. Liss, Inc., pp. 77–96)). In another preferred embodiment, techniques which were developed for the production of chimeric antibodies (see e.g., Morrison, et al., 1984. *Proc. Natl. Acad. Sci. USA* 81:6851–6855; Takeda, et al., 1985. *Nature* 314:452–454) by splicing the genes from a murine antibody specific for the HPS protein•HPS protein-IP complex or HPIP1 and human HN1 homolog protein, together with genes encoding a human antibody molecule of the appropriate specificity and biological activity, may be utilized. In another preferred embodiment of the present invention, methodologies for the production of single-chain antibodies (see e.g., U.S. Pat. No. 4,946,778) may be utilized to produce HPS protein•HPS protein-IP complex-specific and an HPIP1 and human HN1 homolog protein-specific, single-chain antibody. In yet another preferred embodiment, methodologies for the construction of $F_{ab}$ expression libraries (see e.g., Huse, et al., 1989. *Science* 246:1275–1281) are disclosed so as to allow the rapid and efficacious identification of monoclonal $F_{ab}$ fragments with the desired specificity for the HPS protein•HPS protein-IP complex, or an individual HPIP1 and human HN1 homolog protein, derivative, homolog or analog. It should also be noted that non-human antibodies may be "humanized" by several methods known within the art (see e.g., U.S. Pat. No. 5,225,539).

Similarly, antibody fragments which contain the idiotypes of an HPS protein•HPS protein-IP complex or of an HPIP1 and human HN1 homolog protein may be generated by techniques known in the art including, but not limited to: (i) production of an $F(ab)_2$ fragment by pepsin digestion of an intact antibody molecule; (ii) $F_{ab}$ fragment production by reduction of the disulfide bridges of an $F(ab)_2$ fragment; (iii) $F_{ab}$ fragment generation by treatment of an antibody molecular with papain and a reducing agent; and (iv) $F_v$ fragments.

The present invention, antibodies specific to a domain of the HPS protein•HPS protein-IP complex are disclosed, as are antibodies to specific domains of the HPIP1 and human HN1 homolog protein. In the production of antibodies, screening for the desired antibody specificity may be accomplished by utilization of any of the known techniques within the art (e.g., enzyme-linked immunosorbent assay; ELISA). In order to select antibodies which are specific for a particular domain of the HPS protein•HPS protein-IP complex or the HPIP1 and human HN1 homolog protein, one may screen hybridomas for the production of an antibody which binds to the fragment of the HPS protein•HPS protein-IP complex, or the HPIP1 and human HN1 homolog protein, containing said domain. The aforementioned antibodies may be utilized for the localization and/or quantitation of a HPS protein•HPS protein-IP complex or of an HPIP1 and human HN1 homolog protein of the present invention (e.g., measuring levels in appropriate physiological samples, in diagnostic methods, etc). In another embodiment of the present invention, anti-HPS protein•HPS protein-IP complex antibodies, and fragments or derivatives thereof, as well as antibodies specific for HPIP1 protein, and fragments or derivatives thereof which contain a binding domain, are disclosed.

(4) Diagnostic and Prognostic Uses of Proteins and Nucleic Acids Associated with the HPS Protein•HPS Protein-IP Complex and HPIP1 and Human HN1 Homolog Protein Proteins HPS protein•HPS protein-IP complexes may be construed as "markers" of normal physiological processes, and thus have diagnostic utility. These processes include, but are not limited to: (i) physiological processes such as vesicular transport, protein trafficking, pigmentation regulation, and platelet function and (ii) pathological processes such as oculocutaneous albinism, platelet dysfunction, neurodegenerative disease and fibrotic lung disease. Furthermore, characterization of a particular patients subpopulation with elevated or deficient levels of an HPS protein•HPS protein-IP complex or HPIP1 and human HN1 homolog protein may lead to new disease classifications, thus furthering diagnostic ability. In addition, detection of levels of the aforementioned proteins, their associated mRNAs or antibodies directed against them, may also be utilized in assays (e.g., immunoassays) to detect, prognose, diagnose, or monitor various conditions, diseases, and disorders, and treatments thereof, which are characterized by aberrant levels of HPS protein•HPS protein-IP complexes or by aberrant levels of HPIP1 and human HN1 homolog protein.

In preferred embodiment of the present invention, an antibodies specific for an HPS protein•HPS protein-IP complex or the HPIP1 and human HN1 homolog proteins are utilized to assay patient tissue or serum samples for the presence of the HPS protein•HPS protein-IP complex or the HPIP1 protein; wherein an aberrant level of said proteins or complex is an indication of a disease condition. "Aberrant levels" is defined as increased or decreased levels relative to those actually present, or in relation to a standard level representing those levels which are present in an analogous sample from a portion of the body or from another individual not having the disorder. The immunoassays which can be utilized include, but are not limited to competitive and non-competitive assay systems using methodologies such as Western blots, radioimmunoassays; enzyme linked immunosorbent assay (ELISA); "sandwich" immunoassays; immunoprecipitation assays; precipitin reactions; gel diffusion precipitin reactions; immunodiffusion assays; agglutination assays; complement-fixation assays; immunoradiometric assays; fluorescent immunoassays; protein-A immunoassays and the like.

Nucleic acids encoding the various components of the HPS protein•HPS protein-IP complexes, the nucleic acids encoding an HPIP1 and human HN1 homolog protein and related nucleotide sequences, subsequences and complementary sequences thereof, comprising a minimum length of at least 8 nucleotides, may also be utilized in hybridization assays as probes. Such hybridization assays may be used to detect, prognose, diagnose, or monitor the various conditions, disorders, or disease states associated with aberrant levels of the mRNAs encoding the components of an HPS protein•HPS protein-IP complex or HPIP1 and human HN1 homolog protein, as described supra. In a preferred embodiment, the hybridization assay is carried out utilizing nucleic acid probes which are capable of hybridizing to the HPS protein and to a binding partner of said HPS protein in order to concurrently measure the expression of both members of an HPS protein•HPS protein-IP complex. Similarly, in another preferred embodiment, the expression of mRNAs encoding HPIP1 and human HN1 homolog protein are measured.

Accordingly, diseases and disorders involving or characterized by aberrant levels of HPS protein•HPS protein-IP complexes may be diagnosed, their suspected presence can be ascertained by screened procedures or a predisposition to the development of such disorders may be detected, by quantitating aberrant levels of an HPS protein•HPS protein-IP complex , non-complexed HPS protein and/or a HPS protein-IP. In addition, functional activities, including but not limited to: binding to an HPS protein-IP, detection of mutations in the HPS protein and/or in an HPS protein-IP RNA, DNA or protein (e.g., translocations, truncations, changes in nucleotide or amino acid sequence relative to the wild-type HPS protein and/or HPS protein-IP) which cause an increase or decrease in the expression or activity of an HPS protein•HPS protein-IP complex, the HPS protein and/or an HPS protein-IP, may also be utilized. Additionally, various immunoassays known within the art may be utilized to determine whether the ratio of the HPS protein•HPS protein-IP complex to the non-complexed components of the HPS protein•HPS protein-IP complex (i.e., the HPS protein and/or the specific HPS protein-IP in the complex of interest) is increased or decreased within samples from patients suffering from a particular disease or disorder, or having a predisposition to develop such a disease or disorder, as compared to the identical ratio within samples from subjects not having such a disease or disorder.

The use of detection techniques, especially those involving antibodies against HPS protein•HPS protein-IP complexes, or against HPIP1 and human HN1 homolog protein, provides a method of detecting specific cells that express the complex or protein. Using such assays, specific cell types can be defined in which one or more particular HPS protein•HPS protein-IP complex, or HPIP1 and human HN1 homolog protein, is expressed, and the presence of the complex or protein can be correlated with cell viability.

Also embodied herein are methodologies for the detection of HPS protein•HPS protein-IP complexes or HPIP1 and human HN1 homolog protein, within cell culture models which express particular HPS protein•HPS protein-IP complex, HPIP1 and human HN1 homolog protein, or derivatives thereof, for the purpose of characterizing or preparing these aforementioned proteins for harvest. This embodiment includes methodologies involving: (i) cell-sorting of prokaryotes (see e.g., Davey & Kell, 1996. *Microbiol. Rev.* 60:641–696); (ii) primary cultures and tissue specimens from eukaryotes (see e.g., Steele, et al., 1996. *Clin. Obstet. Gynecol.* 39:801–813) and continuous cell cultures (see e.g., Orfao & Ruiz-Arguelles, 1996. *Clin. Biochem.* 29:5–9).

The utilization of kits for diagnostic purposes is disclosed herein. A first preferred embodiment discloses a kit which is comprised, in one or more containers, of an anti-HPS protein•HPS protein-IP complex antibody or an antibody specific for one of HPIP1 and human HN1 homolog protein and, optionally, a labeled binding partner to the antibody. The antibody may be detectably-labeled by any means known in the art including, but not limited to: chemiluminescent, enzymatic, fluorescent, colorimeteric or radioactive labels. A second kit embodiment, comprising, in one or more containers, a nucleic acid probe capable of hybridizing to the HPS protein and/or an HPS protein-IP nRNA. Specifically, the kit may include a pair of primers (each in the size range of approximately 6–30 nucleotides) which are capable of priming a PCR amplification (see e.g., Innis, et al., 1990. *PCR Protocols*, Academic Press, Inc., San Diego, Calif.), a ligase chain reaction (see PCT Publication EP 320,308) or other methodologies known within the art (e.g., Qβ replicase, cyclic probe reaction, etc). A kit may, optionally, further contain a predetermined amount of a purified HPS protein•HPS protein-IP complex, the HPS protein, or an HPS protein-IP for use as a standard or control.

(5) Therapeutic Uses of the HPS Protein•HPS Protein-IP Complex and HPIP1 and Human HN1 Homolog Protein The present invention provides for treatment or prevention of various diseases and disorders by the administration of therapeutic compounds (referred to hereinafter as "Therapeutics"). Such Therapeutics include, but are not limited to: HPS protein•HPS protein-IP complexes; the HPS protein and the individual HPS protein-IP proteins, and derivatives, fragments and analogs thereof; antibodies thereto; nucleic acids encoding the HPS protein and/or an HPS protein-IP; the HPS protein and/or HPS protein-IP antisense nucleic acids and the HPS protein•HPS protein-IP complex and HPIP1 and human HN1 homolog protein modulators (i.e., inhibitors, agonists and antagonists).

As reviewed in Section 2, supra, the HPS protein is centrally implicated in physiological processes such as vesicular transport, protein trafficking, pigmentation regulation, and platelet function. Similarly, the HPS protein has also been strongly implicated in protection from pathological conditions including, but not restricted to: oculocutaneous albinism, platelet dysfunction, neurodegenerative disease, and fibrotic lung disease.

The majority of characterized HPS protein-IPs (particularly 14-3-3 eta, Hrs, BMK1 alpha, CDK2, and NF90), as disclosed in the present invention, are involved in signal transduction and secretion processes. A linkage has been demonstrated between signal transduction disorders and induction of cellular apoptosis, which may relate to HPS protein and to the HPS protein-IPs. The present invention also discloses an HPS protein-IP (e.g., 14-3-3 eta) that plays a role in autoimmune-diseases and inflammation. The 14-3-3 family of proteins are important in autoimmune-diseases, for example, by interacting with insulin receptor substrate 1. Furthermore, the HPS protein, and binding partners as identified herein (e.g., 14-3-3 eta, Hrs, atrophin-1, and DGS-I) are significantly implicated in disorders of neurodegeneration. For example, 14-3-3 eta has been shown to be present in Alzheimer's Disease neurofibrillary tangles and within the cerebrospinal fluid of patients with Creutzfeldt-Jakob disease. The ATPase Hrs has been implicated in calcium-regulated secretion. Atrophin-I is the protein product of the gene which has been implicated in dentatorubral pallidoluysian atrophy (DRPLA; Smith's disease) and is ubiquitously expressed in neuronal tissues. DGS-I is the protein associated with the developmental defect DiGeorge Syndrome.

It should also be noted that the HPS protein-IPs encoded by the genes for HPIP1 and uman HN1 homolog protein, may also be related to the implicated functions of the HPS protein nd the HPS protein-IPs described above.

(a) Treatment of Diseases and Disorders with Increased Levels of the HPS Protein and the HPS Protein•HPS Protein-IP Complex A wide range of cellular diseases which are affected by intracellular signal transduction, vesicle transport and protein trafficking may be treated or prevented by the administration of a Therapeutic which modulates (i.e., inhibits, antagonizes, enhances or promotes) the biological of the HPS protein•HPS protein-IP complex and/or HPIP1 and human HN1 homolog protein. Similarly, diseases or disorders which are associated with aberrant HPS protein•HPS protein-IP complex levels or activity, or aberrant levels of HPIP1 and human HN1 homolog protein, may also be treated by administration of a modulating Therapeutic. In a specific embodiment, the activity or level of HPS protein is modulated by administration of a HPS protein-IP. In another specific embodiment, the activity or level of a HPS protein-IP is modulated by administration of the HPS protein.

(b) Antagonizing HPS Protein•HPS Protein-IP Complex Formation or Activity

Diseases and disorders which are characterized by increased (relative to an individual who is not suffering from the disease or disorder) HPS protein•HPS protein-IP complex levels or activity, or increased HPIP1 and human HN1 homolog protein levels or activity, may be treated with Therapeutics which antagonize (i.e., reduce or inhibit) the levels or activity of these aforementioned proteins or protein complexes. Therapeutics that can may be utilized include, but are not limited to: (i) the HPS protein or an HPS protein-IP (or analogs, derivatives or fragments thereof); (ii) anti-HPS protein•HPS protein-IP complex antibodies; (iii) nucleic acids encoding the HPS protein or an HPS protein-IP; (iv) the concurrent administration of the HPS protein and HPS protein-IP antisense nucleic acids, or HPIP1 and human HN1 homolog protein antisense nucleic acids; (v) the HPS protein and/or HPS protein-IP, or HPIP1 and human HN1 homolog protein nucleic acids, which are dysfunctional due to a heterologous [non-HPS-related] insertion within the coding sequences of the HPS protein or HPS protein-IP coding sequences, which are used to "knockout" endogenous HPS protein and/or HPS protein-IP function by homologous recombination (see e.g., Capecchi, 1989. *Science* 244:1288–1292.

In a specific embodiment of the present invention, a nucleic acid containing a portion of a HPS protein and/or a HPS protein-IP gene in which the these aforementioned sequences flank a different gene sequence, is utilized as an HPS protein and/or a HPS protein-IP antagonist or to promote HPS protein and/or HPS protein-IP inactivation by homologous recombination. See e.g., Koller & Smithies, 1989. *Proc. Natl. Acad. Sci. USA* 86:8932–8935; Zijlstra, et al., 1989. *Nature* 342:435–438. Additionally, mutants or derivatives of a first HPS protein-IP which possess greater affinity for the HPS protein than a second HPS protein-IP may be administered to compete with the second HPS protein-IP protein for HPS protein binding, thereby reducing the levels of HPS protein complexes containing the second HPS protein-IP. Other Therapeutics which inhibit HPS protein•HPS protein-IP complex or HPIP1 and human HN1 homolog protein function may be identified by use of known in vitro assays, which are based, for example, on their ability to inhibit HPS protein:HPS protein-IP binding.

In further specific embodiments, Therapeutics which antagonize HPS protein•HPS protein-IP complex formation or activity, or HPIP1 and human HN1 homolog protein activity, are administered therapeutically (including prophylactically) within: (i) diseases or disorders involving an increased level of an HPS protein•HPS protein-IP complex or an HPIP1 and human HN1 homolog protein or (ii) diseases or disorders wherein in vitro or in vivo assays indicate the utility of an HPS protein•HPS protein-IP complex or HPIP1 and human HN1 homolog protein antagonist administration. Increased levels of HPS protein•HPS protein-IP complexes or HPIP1 and human HN1 homolog proteins, may be readily detected by methods standard in the art, which include, but are not limited to: immunoassays to detect and/or visualize HPS protein•HPS protein-IP complexes, or HPIP1 and human HN1 homolog proteins (e.g., Western blot, immunoprecipitation followed by sodium dodecyl sulfate (SDS) polyacrylamide gel electrophoresis, immunocytochemistry, and the like) and/or hybridization assays to detect concurrent expression of the HPS protein and an HPS protein-IP, or individual HPIP1 and human HN1 homolog protein mRNAs (e.g., Northern blot assays, dot blots, in situ hybridization, and the like).

(c) Reducing the Expression of the HPS Protein•HPS Protein-IP Complex

A specific, preferred embodiment for the reduction of HPS protein•HPS protein-IP complex expression (i.e., the expression of the two components of the HPS protein•HPS protein-IP complex and/or formation of said complex) or reducing HPIP1 and human HN1 homolog protein expression, by targeting mRNAs encoding those protein moieties. RNA therapeutics currently fall within three classes, antisense species, ribozymes, or RNA aptamers. See e.g., Good, et al., 1997. *Gene Therapy* 4:45–54.

Antisense oligonucleotides have been the most-widely utilized methodology and will be discussed infra. Ribozyme therapy involves the administration, induced expression, etc., of small RNA molecules with enzymatic ability to cleave, bind, or otherwise inactivate specific RNAs to reduce or eliminate expression of particular proteins. See e.g., Grassi & Marini, 1996. *Annals of Med.* 28:499–510; Gibson, 1996. *Cancer and Metastasis Rev.* 15:287–299. Currently, the generation of "hairpin" and "hammerhead" RNA ribozymes is necessary to specifically-target a particular mRNA, such as the mRNA encoding the HPS protein. RNA aptamers are specific RNA ligands for proteins, such as for Tat and Rev RNA (see e.g., Good, et al., 1997. *Gene Therapy* 4:45–54), which can specifically inhibit their translation.

In another embodiment of the present invention, the activity or level of the HPS protein is reduced by administration of an HPS protein-IP, a nucleic acid which encodes an HPS protein-IP or an antibody which immunospecifically-binds to an HPS protein-IP, or a fragment or derivative of the antibody containing the binding domain thereof In still another aspect of the invention, diseases or disorders associated with increased levels of the HPS protein or a particular HPS protein-IP (e.g., HPIP1 and human HN1 homolog protein) may be treated or prevented by administration of a Therapeutic which increases HPS protein•HPS protein-IP complex formation, if said complex formation acts to reduce or inactivate the HPS protein or the particular HPS protein-IP through HPS protein•HPS protein-IP complex formation.

(d) Treatment of Diseases and Disorders with Decreased Levels of the HPS Protein and the HPS Protein•HPS Protein-IP Complex Diseases and disorders associated with under-expression of an HPS protein•HPS protein-IP complex, the HPS protein or a particular HPS protein-IP, are treated or prevented by administration of a Therapeutic which promotes (i.e., increases or supplies) HPS protein•HPS protein-IP complexes or function. Examples of such a Therapeutic include, but are not limited to: HPS protein•HPS protein-IP complexes and derivatives, analogs and fragments thereof which are functionally active (e.g., are active to form HPS protein•HPS protein-IP complexes), non-complexed HPS protein and HPS protein-IP proteins, and derivatives, analogs, and fragments thereof, and nucleic acids encoding the members of an HPS protein•HPS protein-IP complex, or functionally-active derivatives or fragments thereof (e.g., for use in gene therapy).

(e) Determination of the Physiological Effects of a Therapeutic

Preferably, suitable in vitro or in vivo assays are utilized to determine the effect of a specific Therapeutic and whether its administration is indicated for treatment of the affected tissue. In various specific embodiments, in vitro assays can be carried out with representative cells or cell types involved in a patient's disorder to determine if a Therapeutic has a desired effect upon such cell types.

Compounds for use as Therapeutics can be tested in suitable animal model systems prior to testing in humans, including but not limited to rats, mice, chicken, cows, monkeys, rabbits, etc. For in vivo testing, prior to administration to humans, any animal model system known in the art may be used.

(6) Diseases and Disorders Associated with the HPS Protein or HPS Protein Complex (a) Pigmentation Disorders The HPS protein is strongly implicated in pigmentation disorders, such as oculocutaneous albinism and hypopigmentation. Therapeutics of the present invention, particularly those which modulate (or supply) HPS protein•HPS protein-IP complex activity, may be effective in treating or preventing pigmentation diseases or disorders. Therapeutics which modulate the levels or activity of HPS protein•HPS protein-IP complexes may be assayed by any method known in the art including, but not limited to in vitro assays using cell culture models and in vivo assays using animal models of pigmentation diseases or disorders. See e.g., McGeoch, et al., 1986. *J. Gen. Virol.* 67:813–825.

Accordingly, once a pigmentation disease or disorder has been shown to be amenable to treatment by modulation of HPS protein•HPS protein-IP complex activity, the pigmentation disease or disorder can be treated or prevented by administration of a Therapeutic which modulates HPS protein•HPS protein-IP complex formation, including supplying a HPS protein•HPS protein-IP complex.

(b) Platelet Dysfunction

Platelet dysfunction which may be treated by modulation of HPS protein•HPS protein-IP complex activity is differentiated into two general classes: (i) diseases associated with platelet storage pool deficiency (e.g., Hermansky-Pudlak Syndrome, Chediak-Higashi Syndrome, gray platelet syndrome) or thrombocytopenia and (ii) diseases associated with thrombocytosis or increased clotting tendency (e.g., myocardial infarction, deep venous thrombosis, cardiovascular accident, transient ischemic attack).

Therapeutics of the present invention, particularly those which modulate (or supply) HPS protein•HPS protein-IP complex activity may be effective in treating or preventing platelet dysfunction diseases or disorders. Potentially effective Therapeutics, for example but not by way of limitation, reduce platelet dysfunction diseases or disorders in animal models in comparison to controls. Accordingly, once a platelet dysfunction disease or disorder has been shown to be amenable to treatment by modulation of HPS protein•HPS protein-IP complex activity, that platelet dysfunction disease or disorder may be treated or prevented by administration of a Therapeutic which modulates HPS protein•HPS protein-IP complex formation, including supplying an HPS protein•HPS protein-IP complex.

(c) Neurodegenerative Disorders

The HPS protein has been implicated to play a role in neurodegenerative disease. Accordingly, Therapeutics of the invention, particularly but not limited to those that modulate (or supply) HPS proteins and/or protein complexes may be effective in treating or preventing neurodegenerative disease. Therapeutics of the present invention which modulate HPS protein•HPS protein-IP complexes involved in neurodegenerative disorder may be assayed by any method known in the art for efficacy in treating or preventing such neurodegenerative diseases and disorders. Such assays include, but are not limited to: in vitro assays for regulated cell secretion, protein trafficking, and/or folding or inhibition of apoptosis or in vivo assays using animal models of neurodegenerative diseases or disorders, or the like. Potentially effective Therapeutics, for example, but not by way of limitation, promote regulated cell maturation and prevent cell apoptosis in culture, or reduce neurodegeneration in animal models in comparison to controls.

(d) Fibrous Lung Disease

The HPS protein is also strongly implicated in the etiology of severe fibrous lung disease. Therapeutics of the present invention, particularly those which modulate the levels or activity of HPS protein•HPS protein-IP complexes may be effective in treating or preventing fibrous lung disease. Therapeutics may be assayed by any method known within the art for efficacy in treating or preventing fibrous lung disease including, but not limited to, in vitro assays using cell culture models, and in vivo assays using animal models of fibrous lung disease.

In accord, once a fibrous lung disease has been shown to be amenable to treatment by modulation of HPS protein•HPS protein-IP complexes, that fibrous lung disease can be treated or prevented by administration of a Therapeutic which modulates HPS protein•HPS protein-IP complex formation, including supplying an HPS protein•HPS protein-IP complexes.

(7) Potential Treatment Modalities in HPS-Related Diseases (a) Gene Therapy

Gene therapy refers to therapy performed by the administration of a nucleic acid molecule, of a known, specific nucleotide sequence, to a subject. Any of the methodologies currently known within the art may be use for gene therapy in the practice of the present invention. For general reviews of the methods of gene therapy, see e.g., Goldspiel, et al., 1993. *Clinical Pharmacy* 12:488–505; Wu & Wu, 1991. *Biotherapy* 3:87–95; Tolstoshev, 1993. *Ann. Rev. Pharmacol. Toxicol.* 32:573–596; Mulligan, 1993. *Science* 260:926–932; Morgan & Anderson, 1993. *Ann. Rev. Biochem.* 62:191–217.

In a preferred embodiment of the present invention, a nucleic acid comprising a sequence which encodes the HPS protein, an HPS protein-IP, or a functional derivative thereof, are administered to modulate HPS protein•HPS protein-IP complexes, or to modulate HPIP1 and human HN1 homolog protein function, by way of gene therapy. In more specific preferred embodiments, a nucleic acid or nucleic acids encoding both the HPS protein and an HPS protein-IP, functional derivatives or chimeric protein thereof, are administered by utilization of gene therapy. In these embodiments, the nucleic acid molecule produces its encoded protein(s) which subsequently mediates a therapeutic effect by modulating the HPS protein•HPS protein-IP complex, or by modulating HPIP1 and human HN1 homolog protein function. In particular, this aforementioned nucleic acid possesses a promoter(s) operably linked to the HPS protein and/or the HPS protein-IP coding region(s), said promoter(s) being inducible or constitutive, and optionally, tissue-specific. In another particular embodiment, a nucleic acid molecule is used in which the HPS protein and/or HPS protein-IP coding sequence, or the HPIP1 and human HN1 homolog protein coding sequences, and any other desired sequences, are flanked by regions which promote homologous recombination at a desired site in the genome, thus providing for intra-chromosomal expression of the HPS protein and the HPS protein-IP nucleic acids. See e.g., Koller & Smithies, 1989. *Proc. Natl. Acad. Sci. USA* 86:8932–8935; Zijlstra, et al., 1989. *Nature* 342:435–438. In yet another specific embodiment, the nucleic acid to be introduced for purposes of gene therapy comprises an inducible promoter operably linked to the coding region, such that expression of the nucleic acid is controllable by controlling the presence or absence of the appropriate inducer of transcription.

Delivery of the nucleic acid into a patient may be either direct, in which case the patient is directly exposed to the nucleic acid or nucleic acid-carrying vector, or indirect, in which case, cells are first transformed with the nucleic acid in vitro, then transplanted into the patient. These two approaches are known, respectively, as in vivo and ex vivo gene therapy. In a specific embodiment, the nucleic acid is directly administered in vivo, where it is expressed to produce the encoded product. This can be accomplished by any of numerous methods known in the art including, but not limited to: (i) by constructing it as part of an appropriate nucleic acid expression vector and administering it so that it becomes intracellular; (ii) by infection using a defective or attenuated retroviral or other viral vector (see e.g., U.S. Pat. No. 4,980,286); (iii) by direct injection of naked DNA, or by use of microparticle bombardment (e.g., a gene gun; Biolistic, DuPont); (iv) by coating with lipids or cell-surface receptors or transfecting agents; (v) by encapsulation in liposomes, microparticles, or microcapsules, or by administering it in linkage to a peptide which is known to enter the nucleus; (vi) by administering it in linkage to a ligand subject to receptor-mediated endocytosis (see e.g., Wu & Wu, 1987. *J. Biol. Chem.* 262:4429–4432), which can be used to target cell types specifically expressing the receptors, etc. In another embodiment, a nucleic acid-ligand complex can be formed in which the ligand comprises a fusogenic viral peptide that disrupts endosomes, preventing lysosomal degradation of the nucleic acid. In yet another embodiment, the nucleic acid may be targeted in vivo for cell specific uptake and expression by targeting a specific receptor (see e.g., U.S. Pat. No. 5,844,107). Alternatively, the nucleic acid may be introduced intracellularly and incorporated within host cell DNA for expression, by homologous recombination. See e.g., Koller & Smithies, 1989. *Proc. Natl. Acad. Sci. USA* 86:8932–8935; Zijlstra, et al., 1989. *Nature* 342:435–438.

In a specific, preferred embodiment, a viral vector which contains the HPS protein and/or the HPS protein-IP encoding nucleic acid sequence is utilized. For example, a retroviral vector can be used which has been modified to delete retroviral sequences that are not necessary for packaging of the viral genome and integration into host cell DNA. See e.g., Miller, et al., 1993. *Meth. Enzymol.* 217:581–599. The HPS protein and/or HPS protein-IP (preferably both the HPS protein and HPS protein-IP) encoding nucleic acids, to be used in gene therapy is/are cloned into the vector, which facilitates delivery of the gene into a patient. See e.g., Clowes, et al., 1994. *J. Clin. Invest.* 93:644–651; Kiem, et al., 1994. *Blood* 83:1467–1473.

In another embodiment of the present invention, adenovirus may be utilized as a viral vector in gene therapy and are especially attractive "vehicles" for the delivery of genes to respiratory epithelia. Adenoviruses naturally infect respiratory epithelia where they cause a mild disease, although other targets for adenovirus-based delivery systems include, but are not limited to, the liver, the central nervous system, endothelial cells, and muscle. Adenoviruses have the additional advantage of being capable of infecting non-dividing cells. See e.g., Kozarsky & Wilson, 1993. *Curr. Opin. Gen. Develop.* 3:499–503. Adeno-associated virus (AAV) has also been proposed for use in gene therapy. See e.g., Walsh, et al., 1993. *Proc. Soc. Exp. Biol. Med.* 204:289–300.

Another approach to gene therapy in the practice of the present invention involves transferring a gene into cells in in vitro tissue culture. Usually, the method of transfer includes the transfer of a selectable marker to the cells to facilitate the isolation of those cells which have taken-up and are expressing the transferred gene. In this embodiment, the nucleic acid is introduced into a cell prior to administration in vivo of the resulting recombinant cell by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. See e.g., Loeffler & Behr, 1993. *Meth. Enzymol.* 217:599–618; Cohen, et al., 1993. *Meth. Enzymol.* 217:618–644; Cline, 1985. *Pharmacol. Ther.* 29:69–92. The transfer technique should be selected to provide for the stable transfer of the nucleic acid to the cell so that the nucleic acid is expressible by the cell, and is heritable and expressible by its cell progeny, as well as ensuring that the that the necessary developmental and physiological functions of the recipient cells are not disrupted. The resulting selected, recombinant cells may be delivered to a patient by various methods known in the art. In one preferred embodiment, epithelial cells are injected subcutaneously or applied as a skin graft onto the patient. Recombinant blood cells (e.g., hematopoietic stem or progenitor cells) are preferably administered intravenously. The total concentration of cells utilized, as well as the delivery route, depend upon the desired effect, patient state, and the like, and can be ascertained by those individuals skilled in the art.

Cells into which a nucleic acid can be introduced for purposes of gene therapy encompass any desired, available cell type and include but are not limited to, epithelial cells, endothelial cells, keratinocytes, fibroblasts, muscle cells, hepatocytes, T-lymphocytes, B-lymphocytes, monocytes, macrophages, neutrophils, eosinophils, megakaryocytes, granulocytes; and various hematopoietic stem or progenitor cells (as obtained from bone marrow, umbilical cord blood, peripheral blood, fetal liver, and the like). It should be noted that, preferably, the cell used for gene therapy is autologous to the patient.

In a preferred embodiment of the present invention in which recombinant cells are used in gene therapy, the HPS protein- and/or HPS protein-IP-(preferably both HPS protein and HPS protein-IP) encoding nucleic acid molecule is/are introduced into the cells such that the gene or genes are expressible by the cells or their progeny, and the recombinant cells are then administered in vivo for therapeutic effect. In a specific, preferred embodiment, stem or progenitor cells including, but not limited to, hematopoietic stem cells (HSC), stem cells of epithelial tissues such as the skin and the lining of the gut, embryonic heart muscle cells, liver stem cells (see e.g., PCT Patent Publication WO 94/08598), and neural stem cells (see e.g., Stemple & Anderson, 1992. *Cell* 71:973–985) may be utilized. Epithelial stem cells (ESCs) or keratinocytes can be obtained from tissues such as the skin and the lining of the gut by known procedures (see e.g., Rheinwald, 1980. *Meth. Cell Bio.* 21:229–247) and can be grown in tissue culture (see e.g., Pittelkow & Scott, 1986. *Mayo Clinic Proc.* 61:771). If the ESCs are provided by a donor, a method for suppression of host versus graft reactivity (e.g., irradiation, drug or antibody administration to promote moderate immunosuppression) can also be utilized.

With respect to hematopoietic stem cells (HSC), any technique which provides for the isolation, propagation, and maintenance in vitro of HSCs can be used in this embodiment of the present invention. Techniques by which this may be accomplished include, but are not limited to: (i) the isolation and establishment of HSC cultures from bone marrow cells isolated from the future host, or a donor, or (ii) the use of previously established long-term HSC cultures, which may be allogeneic or xenogeneic. Non-autologous HSC are used preferably in conjunction with a method of suppressing transplantation immune reactions of the future host/patient. In a specific, preferred embodiment of the present invention, human bone marrow cells can be obtained from the posterior iliac crest by needle aspiration (see e.g., Kodo, et al., 1984. *J. Clin. Invest.* 73:1377–1384) and can be made highly enriched or in substantially pure form by any technique known in the art. Long-term cultures of bone marrow cells may be established and maintained by using, for example, modified Dexter cell culture techniques (see Dexter, et al., 1977. *J. Cell Physiol.* 91:335) or Witlock-Witte culture techniques (see Witlock & Witte, 1982. *Proc. Natl. Acad. Sci. USA* 79:3608–3612).

(b) Utilization of Antisense Oligonucleotides embodiment of the present invention, HPS protein•HPS protein-IP complex formation and function may be inhibited by the use of anti-sense nucleic acids for the HPS protein and/or HPS protein-IP, and is preferably comprised of both the HPS protein and HPS protein-IP. In addition, the present invention discloses the therapeutic or prophylactic use of nucleic acids (of at least six nucleotides in length) which are anti-sense to a genomic sequence (gene) or cDNA encoding the HPS protein and/or HPS protein-IP, or portions thereof. Such anti-sense nucleic acids have utility as Therapeutics which inhibit HPS protein•HPS protein-IP complex formation or activity, and may be utilized in a therapeutic or prophylactic manner.

Another specific embodiment of the present invention discloses methodologies for the inhibition of the expression of the HPS protein and HPS protein-IPs nucleic acid sequences, within a prokaryotic or eukaryotic cell, which is comprised of providing the cell with an therapeutically-effective amount of an anti-sense nucleic acid of the HPS protein and HPS protein-IP, or derivatives thereof.

The anti-sense nucleic acids of the present invention may be oligonucleotides which may either be directly administered to a cell or which may be produced in vivo by transcription of the exogenous, introduced sequences. In addition, the anti-sense nucleic acid may be complementary to either a coding (i.e., exonic) and/or non-coding (i.e., intronic) region of the HPS protein or HPS protein-IPs mRNAs. The HPS protein and HPS protein-IPs anti-sense nucleic acids are, at least, six nucleotides in length and are, preferably, oligonucleotides ranging from 6–200 nucleotides in length. In specific embodiments, the anti-sense oligonucleotide is at least 10 nucleotides, at least 15 nucleotides, at least 100 nucleotides, or at least 200 nucleotides. The anti-sense oligonucleotides may be DNA or RNA (or chimeric mixtures, derivatives or modified versions thereof), may be either single-stranded or double-stranded and may be modified at a base, sugar or phosphate backbone moiety.

In addition, the anti-sense oligonucleotide of the present invention may include other associated functional groups, such as peptides, moieties which facilitate the transport of the oligonucleotide across the cell membrane, a hybridization-triggered cross-linking agent, a hybridization-triggered cleavage-agent, and the like. See e.g., Letsinger, et al., 1989. Proc. Natl. Acad. Sci. U.S.A. 86:6553–6556; PCT Publication No. WO 88/09810. In a specific embodiment, the HPS protein and HPS protein-IPs antisense oligonucleotides comprise catalytic RNAs or ribozymes. See, e.g., Sarver, et al., 1990. Science 247:1222–1225.

The anti-sense oligonucleotides of the present invention may be synthesized by standard methodologies known within the art including, but not limited to: (i) automated phosphorothioate-mediated oligonucleotide synthesis (see e.g., Stein, et al., 1988. Nuc. Acids Res. 16:3209) or (ii) methylphosphonate oligonucleotides can be prepared by use of controlled pore glass polymer supports (see e.g., Sarin, et al., 1988. Proc. Natl. Acad. Sci. U.S.A. 85:7448–7451).

In an alternative embodiment, the HPS protein and HPS protein-IPs antisense nucleic acids are produced intracellularly by transcription of an exogenous sequence. For example, a vector may be produced which (upon being exocytosed by the cell) is transcribed in vivo, thus producing an antisense nucleic acid (RNA) species. The aforementioned vector may either remain episomal or become chromosomally-integrated, so long as it can be transcribed to produce the desired antisense RNA. The vectors utilized in the practice of the present invention may be derived from bacterial, viral, yeast or other sources known within the art, which are utilized for replication and expression in mammalian cells. Expression of the sequences encoding the HPS protein and HPS protein-IPs antisense RNAs may be facilitated by any promoter known within the art to function in mammalian, preferably, human cells. Such promoters may be inducible or constitutive and include, but are not limited to: (i) the SV40 early promoter region; (ii) the promoter contained in the 3'-terminus long terminal repeat of Rous sarcoma virus (RSV); (iii) the Herpesvirus thymidine kinase promoter and (iv) the regulatory sequences of the metallothionein gene.

The HPS protein and HPS protein-IPs antisense nucleic acids may be utilized prophylactically or therapeutically in the treatment or prevention of disorders of a cell type which expresses (or preferably over-expresses) the HPS protein•HPS protein-IP complex. Cell types which express or over-express the HPS protein and HPS protein-IPs RNA may be identified by various methods known within the art including, but are not limited to, hybridization with HPS protein- and HPS protein-IP-specific nucleic acids (e.g., by Northern hybridization, dot blot hybridization, in situ hybridization) or by observing the ability of RNA from the specific cell type to be translated in vitro into the HPS protein and the HPS protein-IPs by immunohistochemistry. In a preferred aspect, primary tissue from a patient may be assayed for the HPS protein and/or HPS protein-IPs expression prior to actual treatment by, for example, immunocytochemistry or in situ hybridization.

Pharmaceutical compositions of the present invention, comprising an effective amount of a HPS protein and HPS protein-IPs antisense nucleic acid contained within a pharmaceutically-acceptable carrier may be administered to a patient having a disease or disorder which is of a type that expresses or over-expresses HPS protein•HPS protein-IP complex RNA or protein. The amount of HPS protein and/or HPS protein-IPs antisense nucleic acid which will be effective in the treatment of a particular disorder or condition will be dependant upon the nature of the disorder or condition, and may be determined by standard clinical techniques. Where possible, it is desirable to determine the antisense cytotoxicity in vitro, and then in useful animal model systems prior to testing and use in humans. In a specific embodiment, pharmaceutical compositions comprising HPS protein and HPS protein-IPs antisense nucleic acids may be administered via liposomes, microparticles, or microcapsules. See e.g., Leonetti, et al., 1990. Proc. Natl. Acad. Sci. U.S.A. 87:2448–2451.

(8) HPS Protein and HPS Protein•HPS Protein-IP Complex Assays

The functional activity of an HPS protein•HPS protein-IP, HPIP1 and human HN1 omolog protein, or derivatives, fragments and analogs thereof, may be assayed by various ethodologies known within the art. Potential functional modulators (e.g., inhibitors, agonists and antagonists) of HPS protein•HPS protein-IP complex or HPIP1 and human HN1 homolog protein activity (e.g., antibodies or antisense nucleic acids specific for the HPS protein, HPS protein-IPs, or HPS protein-IP complex) may be assayed for by their ability to modulate HPS protein•HPS protein-IP complex formation and/or activity, and for the ability to modulate HPIP1 and human HN1 homolog protein activity.

(a) Immunoassays

In one embodiment of the present invention, where one is assaying for the ability to bind or compete with wild-type HPS protein or HPS protein-IP protein, for binding to antibodies specific for the aforementioned proteins or protein complexes, various immunoassay methodologies known in the art may be used, including but not limited to, competitive and non-competitive assay systems using techniques such as radioimmunoassays, enzyme linked immunosorbent assay (ELISA), "sandwich" immunoassays, immunoradiometric assays, gel diffusion precipitin reactions, immunodiffusion assays, in situ immunoassays, Western blots, precipitation reactions, agglutination assays, complement fixation assays, immunofluorescence assays, protein-A assays, immunoelectrophoresis assays, and the like.

(b) Gene Expression Assays

The expression of the HPS protein or HPS protein-IPs genes (both endogenous genes and those expressed from recombinant DNA) may be detected using techniques known within the art including, but not limited to: Southern hybridization, Northern hybridization, restriction endonuclease mapping, DNA sequence analysis and polymerase chain reaction amplification (PCR) followed by Southern hybridization or RNase protection (see e.g., Current Protocols in Molecular Biology 1997. (John Wiley and Sons, New York, N.Y.)) with probes specific for the HPS protein and HPS protein-IPs genes in various cell types.

In one specific embodiment of the present invention, Southern hybridization may be used to detect genetic linkage of the HPS protein and/or HPS protein-IPs gene mutations to physiological or pathological states. Numerous cell types, at various stages of development, may be characterized for their expression of the HPS protein and HPS protein-IPs (particularly the concomitant expression of the HPS protein and HPS protein-IPs within the same cells). The stringency of the hybridization conditions for Northern or Southern blot analysis may be manipulated to ensure detection of nucleic acids with the desired degree of relatedness to the specific probes used. Modification of these aforementioned methods, as well as other methods well-known within the art, may be utilized in the practice of the present invention.

(c) Binding Assays

Derivatives (e.g., fragments), analogs and homologs of HPS protein-IPs may be assayed for their ability to bind to the HPS protein by any method known within the art, including, but not limited to, the modified yeast two hybrid assay system, immunoprecipitation with an antibody which binds to the HPS protein in a complex followed by size fractionation analysis of the immunoprecipitated proteins by denaturing or non-denaturing polyacrylamide gel electrophoresis, Western analysis, non-denaturing gel electrophoresis, and similar methodologies.

(d) Biological Activity Assays

One embodiment of the present invention provides a methodology for the screening of a derivative, analog or homolog of the HPS protein for biological activity comprising contacting said derivative, analog or homolog of the HPS protein with a protein selected from the group consisting of HPIP1 and human HN1 homolog protein, and detecting the subsequent formation of a complex between said derivative, analog or homolog of the HPS protein and said protein; wherein detecting formation of said complex indicates that said derivative, analog or homolog of the HPS protein possesses biological (e.g., binding) activity.

An additional embodiment discloses a method for the screening of a derivative, analog or homolog of a protein selected from the group consisting of 14-3-3 protein, Hrs, BMK1 alpha, CDK2, NF90, atrophin-1, DGS-I, or HPIP1 and human HN1 homolog protein for biological activity comprising contacting said derivative, analog or homolog of said protein with the HPS protein; and detecting the subsequent formation of a complex between said derivative, analog or homolog of said protein and the HPS protein; wherein detecting the formation of the complex indicates that said derivative, analog or homolog of said protein possesses biological (e.g., binding) activity.

(e) Modulation of Protein Biological Activity

The present invention also discloses methodologies for the modulation of the biological activity of a protein of interest which can participate in an HPS protein•HPS protein-IP by the administration of a binding partner of that protein of interest, or a derivative or analog thereof. For example, the ability of the HPS protein (and derivatives or analogs thereof) to modulate the activity or level of an HPS protein-IP may be ascertained by such methodologies as contacting a cell, administering to an animal, expressing an HPS protein-IP gene with a HPS protein, or a nucleic acid encoding a HPS protein, or an antibody which immunospecifically binds the HPS protein, and measuring a change in HPS protein-IP levels or activity. A change in HPS protein-IP levels or activity is indicative of the HPS protein possessing the ability to modulate HPS protein-IP levels or activity.

In an alternative embodiment of the present invention, an HPS protein-IP may be assayed for the ability to modulate the activity or levels of the HPS protein by contacting a cell, administering to an animal, expressing the HPS protein gene with: (i) an HPS protein-IP; (ii) a nucleic acid encoding an HPS protein-IP or (iii) an antibody which immunospecifically binds to a HPS protein-IP, or a fragment or derivative of said antibody containing the binding domain thereof, wherein a change in the HPS protein levels or activity indicates that the HPS protein-IP can modulate HPS protein levels or activity.

The HPS protein•HPS protein-IP complex, or HPIP1 and human HN1 homolog protein, or derivative, analog, or fragment thereof, may also be screened for activity in modulating the activity of the HPS protein and the HPS protein binding partners (i.e., the HPS protein-IPs), particularly, HPIP1 and human HN1 homolog protein. The proteins and protein complexes of the present invention may be screened for the ability to modulate (i.e., increase or decrease) HPS protein•HPS protein-IP complexes, as discussed infra.

(f) Assays for the Treatment of Pigmentation Disorders

The HPS protein has been implicated in etiology of pigmentation disorders, including oculocutaneous albinism and hypopigmentation. Accordingly, HPS protein•HPS protein-IP complexes, and derivatives, analogs, and fragments thereof, nucleic acids encoding the HPS protein genes, anti-HPS protein•HPS protein-IP complexes, and other modulators, may be tested for activity in treating or preventing pigmentation disorders in both in vitro and in vivo assays.

In one embodiment, a Therapeutic can be assayed for activity in treating or preventing pigmentation disorders by contacting cultured cells which exhibit an indicator of an pigmentation reaction, in vitro, with the Therapeutic, and comparing the level of indicator in the cells contacted with the Therapeutic with said level of the indicator in cells not so contacted, wherein a lower level in said contacted cells indicates that the Therapeutic has activity in treating or preventing pigmentation disorders. Cell models that can be used for such assays include, but are not limited to, in vitro studies using cultured vitiligo melanocytes and keratinocytes (see e.g., Bessou, et al., 1997. *Br. J. Dermatol.* 137:890–897); lines of immortal, severely hypopigmented melanocytes and melanoblasts from mice of the null genotype p(cp)/p(25H) (see e.g., Sviderskaya, et al., 1997. *J. Invest. Dermatol.* 108:30–34) and organotypic culture of human skin to study melanocyte migration (see e.g., Le Poole, et al., 1994. *Pigment. Cell Res.* 7:33–43).

(g) Assays for the Treatment of Platelet Dysfunction

As previously discussed, the HPS protein has been implicated in platelet dysfunction.

Accordingly, the HPS-associated proteins and protein complexes may be tested for activity in treating or preventing such platelet dysfunction in in vitro and in vivo assays.

In one embodiment, a Therapeutic of the invention can be assayed for activity in treating or preventing platelet dysfunction by contacting cultured cells in vitro that exhibit an indicator of an platelet reaction with the Therapeutic, and comparing the level of indicator in the cells contacted with the Therapeutic with said level of the indicator in cells not so contacted. In another embodiment, a Therapeutic of the invention can be assayed for activity in treating or preventing platelet dysfunction by administering said Therapeutic to a test animal exhibiting an platelet reaction or which test animal does not exhibit an platelet reaction and is subsequently challenged with an agent that elicits an platelet reaction; and measuring the change in the platelet reaction after the administration of said Therapeutic.

A number of animal models of platelet dysfunction, which accurately mimic natural, human platelet dysfunction, are known within the art. Examples of specific models include, but are not limited to, a skin bleeding-time test in a rat model (see MacDonald, et al., 1994. *Thromb; Res*. 76:535–540); correlation between bleeding-time and antithrombotic effect of platelet-suppressive agents in rat experimental model (see Suehiro, et al., 1994. *Res. Commun. Chem. Pathol. Pharmacol*. 83:157–163) and others similar assays.

(h) Assays for the Treatment of Neurodegenerative Diseases

HPS is associated with a variety of neurodegenerative disorders. In one embodiment of the present invention, a Therapeutic of the invention may be assayed for by its activity in treating or preventing neurodegenerative disease by contacting cultured cells which exhibit an indicator of a neurodegenerative disease, such as over-expression of the α-A4 peptide, in vitro, with the Therapeutic, and comparing the level of said indicator in the cells contacted with the Therapeutic with said level of said indicator in cells not so contacted, wherein a lower level in said contacted cells indicates that the Therapeutic has activity in treating or preventing neurodegenerative disease. Specific examples of cell culture models for neurodegenerative disease include, but are not limited to, cultured rat endothelial cells from affected and non-affected individuals (see e.g., Maneiro, et al., 1997. *Meth. Find. Exp. Clin. Pharmacol*. 19:5–12); P19 murine embryonal carcinoma cells (see e.g., Hung, et al., 1992. *Proc. Natl. Acad. Sci. USA* 89:9439–9443) and dissociated cell cultures of cholinergic neurons from the nucleus basalis of Meynert (see e.g., Nakajima, et al., 1985. *Proc. Natl. Acad. Sci. USA*, 82:6325–6329).

In another embodiment, a Therapeutic of the invention can be assayed for activity in treating or preventing neurodegenerative disease by administering the Therapeutic to a test animal that exhibits symptoms of a neurodegenerative disease, such as premature development of cognitive deficiencies in transgenic animals expressing a-APP, or that is predisposed to develop symptoms of a neurodegenerative disease; and measuring the change in said symptoms of the neurodegenerative disease after administration of said Therapeutic. Examples of specific neurodegenerative disease animal models include, but are not limited to, the partial trisomy 16 mouse (see Holtzman, et al., 1996. *Proc. Natl. Acad. Sci. USA* 93:13333–13338); bilateral nucleus basalis magnocellularis-lesioned rats (see Popovic, et al., 1996. *Int. J. Neurosci*. 86:281–299); the aged rat (Muir, 1997. *Pharmacol. Biochem. Behav*. 56:687–696), the PDAPP transgenic mouse model of Alzheimer's disease (Johnson-Wood, et al., 1997. *Proc. Natl. Acad. Sci. USA* 94:1550–1555), and experimental autoimmune dementia (Oron, et al., 1997. *J. Neural Transm. Suppl*. 49:77–84).

(i) Screening of HPS Protein and Protein Complex Antagonists and Agonists

The present invention provides assays for the detection of molecules which specifically bind to HPS protein•HPS protein-IP complexes, the HPS protein, or HPS protein-IP nucleic acids, proteins or derivatives. For example, recombinant cells expressing both HPS protein and/or HPS protein-IP nucleic acids, or expressing HPIP1 and human HN1 homolog protein nucleic acids, can be used to recombinantly produce the complexes or proteins used in these assays, to screen for molecules which bind or interfere with HPS protein•HPS protein-IP complexes, or which interfere with HPIP1 and human HN1 homolog protein function.

In additional preferred embodiments of the present invention, modulators are identified by administering a candidate molecule to a transgenic, non-human animal expressing both the HPS protein and a HPS protein-IP from promoters that are not the native the HPS protein or the native HPS protein-IP promoters, more preferably where the candidate molecule is also recombinantly expressed in the transgenic non-human animal. Alternatively, the method for identifying such modulators can be carried out in vitro, preferably with purified HPS protein purified HPS protein-IP, and a purified candidate molecule. Agents to be screened may also include all forms of antisera, antisense nucleic acids, etc., which can modulate HPS protein•HPS protein-IP complex activity, or modulate an HPIP1 and human HN1 homolog protein activity.

By way of example, and not of limitation, diversity libraries, such as random or combinatorial peptide or non-peptide libraries may be screened for molecules that specifically bind to an HPS protein•HPS protein-IP complex, or to an HPIP1 and human HN1 homolog protein. Many libraries are known within the art including, but not limited to, chemically synthesized libraries, recombinant libraries (e.g., phage display libraries) and in vitro translation-based libraries. Screening the libraries can be accomplished by any of a variety of commonly employed methodologies known methods. See e.g., Bock, et al., 1992. *Nature* 355:564–566; Tuerk, et al., 1992. *Proc Natl. Sci. USA* 89:6988–6992; U.S. Pat. No. 5,096,815; U.S. Pat. No. 5,223,409; U.S. Pat. No. 5,198,346; PCT Publication No. WO 94/18318.

In a preferred embodiment, agents which modulate (i.e., inhibit, antagonize or agonize) HPS protein•HPS protein-IP complex activity may be screened using a binding-inhibition assay, wherein agents are screened for their ability to inhibit formation of a HPS protein•HPS protein-IP complex under aqueous, physiological binding conditions in which HPS protein•HPS protein-IP complex formation occurs in the absence of the agent to be tested. Agents which interfere with the formation of HPS protein•HPS protein-IP complexes are identified as antagonists of complex formation. Agents which eliminate the formation of HPS protein•HPS protein-IP complexes are identified as inhibitors of complex formation. Agents which enhance the formation of HPS protein•HPS protein-IP complexes are identified as agonists of complex formation.

Methodologies utilized in the practice of the present invention s for screening may involve labeling the complex proteins with: (i) radioligands (e.g., 251 or $^3$H); (ii) magnetic ligands (e.g., paramagnetic beads covalently attached to photobiotin acetate); (iii) fluorescent ligands (e.g., fluorescein or rhodamine) or (iv) enzyme ligands (e.g., luciferase or beta-galactosidase). The reactants which bind in solution may then be isolated by one of many techniques known in the art, including but not restricted to, co-immunoprecipitation of the labeled moiety using antisera against the unlabeled binding partner (or a binding partner labeled with a distinguishable marker from that used on the labeled moiety); immunoaffinity chromatography; size exclusion chromatography and gradient density centrifugation. Upon binding, the labeled species is rendered unable to pass through the filter, providing for a simple assay of complex formation.

Typical binding assays are performed, for example, but not by way of limitation, in an aqueous salt solution of 10–250 mM NaCl, 5–50 mM Tris-HCl, pH 5–8, and 0.5% Triton X-100 or other detergent which improves the specificity of interaction. Metal chelators and/or divalent cations may be added to improve binding and/or reduce proteolysis. Reaction temperatures may include 4, 10, 15, 22, 25, 35, or 42° C., and time of incubation is typically at least 15 seconds, but longer times are preferred so as to allow binding equilibrium to occur. Particular HPS protein•HPS protein-IP complexes may be assayed using routine protein binding assays to determine optimal binding conditions for reproducible binding. The physical parameters of complex formation may then be analyzed by quantitation of complex formation using assay methods specific for the particular label being utilized (i.e., liquid scintillation spectroscopy for radioactivity detection). The reaction results are then quantitatively analyzed utilizing Scatchard analysis, Hill analysis, and other methods commonly known in the art. See e.g., *Proteins, Structures, and Molecular Principles*, $2^{nd}$ Ed.(1993) Creighton, Ed., (W. H. Freeman and Company, New York, N.Y.).

In a second common approach to binding assays, one of the binding species is immobilized on a solid-state platform (e.g., a filter, a microtiter plate well, a test tube, a chromatography matrix, and the like) either by covalent or non-covalent means. In one embodiment, immobilized HPS protein is utilized to assay for binding with a radioactively-labeled HPS protein-IP in the presence and absence of a compound to be tested for its ability to modulate HPS protein•HPS protein-IP complex formation. The binding partners are allowed to bind under aqueous, physiological conditions (i.e., the conditions under which the original interaction was detected). Conversely, in yet another embodiment, the HPS protein-IP is immobilized and contacted with the labeled HPS protein, or derivative thereof, under binding conditions.

(j) Assays for Protein-Protein Interactions

The present invention discloses methodologies for assaying and screening derivatives, fragments, analogs and homologs of HPS protein-IPs for binding to HPS protein. The derivatives, fragments, analogs and homologs of the HPS protein-IPs which interact with HPS protein may be identified by means of a yeast two hybrid assay system (see e.g., Fields & Song, 1989. *Nature* 340:245–246) or; preferably, a modification and improvement thereof, as described in U.S. patent application Ser. Nos. 08/663,824 (filed Jun. 14, 1996) and 08/874,825 (filed Jun. 13, 1997), both of which are entitled "Identification and Comparison of Protein-Protein Interactions that Occur in Populations and Identification of Inhibitors of These Interactions," to Nandabalan, et al., and which are incorporated by reference herein in their entireties.

The identification of interacting proteins by the improved yeast two hybrid system is based upon the detection of the expression of a reporter gene (hereinafter "Reporter Gene"), the transcription of which is dependent upon the reconstitution of a transcriptional regulator by the interaction of two proteins, each fused to one half of the transcriptional regulator. The bait HPS protein (or derivative, fragment, analog or homolog) and prey protein (proteins to be tested for ability to interact with the bait protein) are expressed as fusion proteins to a DNA-binding domain, and to a transcriptional regulatory domain, respectively, or vice versa. In a specific embodiment of the present invention, the prey population may be one or more nucleic acids encoding mutants of HPS protein-IPs (e.g., as generated by site-directed mutagenesis or another method of producing mutations in a nucleotide sequence). Preferably, the prey populations are proteins encoded by DNA (e.g., cDNA, genomic DNA or synthetically generated DNA). For example, the populations may be expressed from chimeric genes comprising cDNA sequences derived from a non-characterized sample of a population of cDNA from mammalian RNA. In another specific embodiment, recombinant biological libraries expressing random peptides may be used as the source of prey nucleic acids.

The present invention discloses methods for the screening for inhibitors of HPS protein-IP. In brief, the protein-protein interaction assay may be performed as previously described herein, with the exception that it is performed in the presence of one or more candidate molecules. A resulting increase or decrease in Reporter Gene activity, in relation to that which was present when the one or more candidate molecules are absent, indicates that the candidate molecule exerts an effect on the interacting pair. In a preferred embodiment, inhibition of the protein interaction is necessary for the yeast cells to survive, for example, where a non-attenuated protein interaction causes the activation of the URA3 gene, causing yeast to die in medium containing the chemical 5-fluoroorotic acid. See e.g., Rothstein, 1983. *Meth. Enzymol.* 101:167–180

In general, the proteins comprising the bait and prey populations are provided as fusion (chimeric) proteins, preferably by recombinant expression of a chimeric coding sequence containing each protein contiguous to a pre-selected sequence. For one population, the pre-selected sequence is a DNA-binding domain that may be any DNA-binding domain, so long as it specifically recognizes a DNA sequence within a promoter (e.g., a transcriptional activator or inhibitor). For the other population, the pre-selected sequence is an activator or inhibitor domain of a transcriptional activator or inhibitor, respectively. The regulatory domain alone (not as a fusion to a protein sequence) and the DNA-binding domain alone (not as a fusion to a protein sequence) preferably, do not detectably interact, so as to avoid false-positives in the assay. The assay system further includes a reporter gene operably linked to a promoter that contains a binding site for the DNA-binding domain of the transcriptional activator (or inhibitor). Accordingly, in the practice of the present invention, the binding of the HPS protein fusion protein to a prey fusion protein leads to reconstitution of a transcriptional activator (or inhibitor), which concomitantly activates (or inhibits) expression of the Reporter Gene.

In a specific embodiment, the present invention discloses a methodology for detecting one or more protein-protein interactions comprising the following steps: (i) recombinantly-expressing the HPS protein (or a derivative, fragment, analog or homolog thereof) in a first population of yeast cells of a first mating type and possessing a first fusion protein containing the HPS protein sequence and a DNA-binding domain; wherein said first population of yeast cells contains a first nucleotide sequence operably-linked to a promoter which is "driven" by one or more DNA-binding sites recognized by said DNA-binding domain such that an interaction of said first fusion protein with a second fusion protein (comprising a transcriptional activation domain) results in increased transcription of said first nucleotide sequence; (ii) negatively selecting to eliminate those yeast cells in said first population in which said increased transcription of said first nucleotide sequence occurs in the absence of said second fusion protein; (iii) recombinantly expressing in a second population of yeast cells of a second mating type different from said first mating type, a plurality of said second fusion proteins; wherein said second fusion protein is comprised of a sequence of a derivative, fragment, analog or homolog of aHPS protein-IPs and an activation domain of a transcriptional activator, in which the activation domain is the same in each said second fusion protein; (iv) mating said first population of yeast cells with said second population of yeast cells to form a third population of diploid yeast cells, wherein said third population of diploid yeast cells contains a second nucleotide sequence operably linked to a promoter "driven" by a DNA-binding site recognized by said DNA-binding domain such that an interaction of a first fusion protein with a second fusion protein results in increased transcription of said second nucleotide sequence, in which the first and second nucleotide sequences can be the same or different and (v) detecting said increased transcription of said first and/or second nucleotide sequence, thereby detecting an interaction between a first fusion protein and a second fusion protein.

In a preferred embodiment, the bait (a HPS protein sequence) and the prey (a library of chimeric genes) are combined by mating the two yeast strains on solid media for a period of approximately 6–8 hours. In a less preferred embodiment, the mating is performed in liquid media. The resulting diploids contain both types of chimeric genes (i.e., the DNA-binding domain fusion and the activation domain fusion). After an interactive population is obtained, the DNA sequences encoding the pairs of interactive proteins are isolated by a method wherein either the DNA-binding domain hybrids or the activation domain hybrids are amplified, in separate reactions. Preferably, the amplification is carried out by polymerase chain reaction (PCR; see e.g., Innis, et al., 1990. PCR Protocols (Academic Press, Inc., San Diego, Calif.)) utilizing pairs of oligonucleotide primers specific for either the DNA-binding domain hybrids or the activation domain hybrids. The PCR amplification reaction may also be performed on pooled cells expressing interacting protein pairs, preferably pooled arrays of interactants. Other amplification methods known within the art may also be used including, but not limited to, ligase chain reaction; $Q\beta$-replicase or the like. See e.g., Kricka, et al., 1995. *Molecular Probing, Blotting, and Sequencing* (Academic Press, New York, N.Y.).

In an additional embodiment of the present invention, the plasmids encoding the DNA-binding domain hybrid and the activation domain hybrid proteins may also be isolated and cloned by any of the methods well-known within the art. For example, but not by way of limitation, if a shuttle (yeast to *E. coli*) vector is used to express the fusion proteins, the genes may be subsequently recovered by transforming the yeast DNA into E. coli and recovering the plasmids from the bacteria. See e.g., Hoffman, et al., 1987. *Gene* 57:267–272.

(9) Pharmaceutical Compositions and Administration of Therapeutics

The present invention discloses methods of treatment and prophylaxis by the administration to a subject of an pharmaceutically-effective amount of a Therapeutic of the invention. In a preferred embodiment, the Therapeutic is substantially purified and the subject is a mammal, and most preferably, human.

Formulations and methods of administration that can be employed when the Therapeutic comprises a nucleic acid are described, supra. Various delivery systems are known and can be used to administer a Therapeutic of the present invention including, but not limited to: (i) encapsulation in liposomes, microparticles, microcapsules; (ii) recombinant cells capable of expressing the Therapeutic; (iii) receptor-mediated endocytosis (see, e.g., Wu & Wu, 1987. *J. Biol. Chem.* 262:4429–4432); (iv) construction of a Therapeutic nucleic acid as part of a retroviral or other vector, and the like.

Methods of administration include, but are not limited to, intradermal, intramuscular, intraperitoneal, intravenous, subcutaneous, intranasal, epidural, and oral routes. The Therapeutics of the present invention may be administered by any convenient route, for example by infusion or bolus injection, by absorption through epithelial or mucocutaneous linings (e.g., oral mucosa, rectal and intestinal mucosa, etc.) and may be administered together with other biologically-active agents. Administration can be systemic or local. In addition, it may be advantageous to administer the Therapeutic into the central nervous system by any suitable route, including intraventricular and intrathecal injection. Intraventricular injection may be facilitated by an intraventricular catheter attached to a reservoir (e.g., an Ommaya reservoir). Pulmonary administration may also be employed by use of an inhaler or nebulizer, and formulation with an aerosolizing agent. It may also be desirable to administer the Therapeutic locally to the area in need of treatment; this may be achieved by, for example, and not by way of limitation, local infusion during surgery, topical application, by injection, by means of a catheter, by means of a suppository, or by means of an implant. In a specific embodiment, administration may be by direct injection at the site (or former site) of a malignant tumor or neoplastic or pre-neoplastic tissue.

In another embodiment of the present invention, the Therapeutic may be delivered in a vesicle, in particular a liposome. See e.g., Langer, 1990. *Science* 249:1527–1533. In yet another embodiment, the Therapeutic can be delivered in a controlled release system including, but not limited to: a delivery pump (see e.g., Saudek, et al., 1989. *New Engl. J. Med.* 321:574 and a semi-permeable polymeric material (see e.g., Howard, et al., 1989. *J. Neurosurg.* 71:105). Additionally, the controlled release system can be placed in proximity of the therapeutic target (e.g., the brain), thus requiring only a fraction of the systemic dose. See, e.g., Goodson, In: *Medical Applications of Controlled Release* 1984. (CRC Press, Bocca Raton, Fla.).

In a specific embodiment of the present invention, where the Therapeutic is a nucleic acid encoding a protein, the Therapeutic nucleic acid may be administered in vivo to promote expression of its encoded protein, by constructing it as part of an appropriate nucleic acid expression vector and administering it so that it becomes intracellular (e.g., by use of a retroviral vector, by direct injection, by use of microparticle bombardment, by coating with lipids or cell-surface receptors or transfecting agents, or by administering it in linkage to a homeobox-like peptide which is known to enter the nucleus (see e.g., Joliot, et al., 1991. *Proc. Natl. Acad. Sci. USA* 88:1864–1868), and the like. Alternatively, a nucleic acid Therapeutic can be introduced intracellularly and incorporated within host cell DNA for expression, by homologous recombination.

The present invention also provides pharmaceutical compositions. Such compositions comprise a therapeutically-effective amount of a Therapeutic, and a pharmaceutically acceptable carrier. As utilized herein, the term "pharmaceutically acceptable" means approved by a regulatory agency of the Federal or a state government or listed in the U.S. Pharmacopoeia or other generally recognized pharmacopoeia for use in animals and, more particularly, in humans. The term "carrier" refers to a diluent, adjuvant, excipient, or vehicle with which the therapeutic is administered and includes, but is not limited to such sterile liquids as water and oils.

The amount of the Therapeutic of the invention which will be effective in the treatment of a particular disorder or condition will depend on the nature of the disorder or condition, and may be determined by standard clinical techniques by those of average skill within the art. In addition, in vitro assays may optionally be employed to help identify optimal dosage ranges. The precise dose to be employed in the formulation will also depend on the route of administration, and the overall seriousness of the disease or disorder, and should be decided according to the judgment of the practitioner and each patient's circumstances. However, suitable dosage ranges for intravenous administration of the Therapeutics of the present invention are generally about 20–500 micrograms ($\mu$g) of active compound per kilogram (Kg) body weight. Suitable dosage ranges for intranasal administration are generally about 0.01 picograms (pg)/kg body weight to 1 mg/kg body weight. Effective doses may be extrapolated from dose-response curves derived from in vitro or animal model test systems. Suppositories generally contain active ingredient in the range of 0.5% to 10% by weight; oral formulations preferably contain 10% to 95% active ingredient.

The present invention also provides a pharmaceutical pack or kit, comprising one or more containers filled with one or more of the ingredients of the pharmaceutical compositions and Therapeutics of the present invention. Optionally associated with such container(s) may be a notice in the form prescribed by a governmental agency regulating the manufacture, use or sale of pharmaceuticals or biological products, which notice reflects approval by the agency of manufacture, use or sale for human administration.

10) Specific Experimental Examples
(a) Identification of HPS protein•HPS protein-IP complexes A modified, improved yeast two hybrid system was utilized to identify protein interactions. Yeast is an eukaryote, and therefore, any intramolecular protein interactions detected in this type of system demonstrate protein interactions that occur under physiological conditions. See e.g., Chien, et al., 1991. *Proc. Natl. Sci. USA* 88:9578–9581. Expression vectors were constructed to encode two hybrid proteins. For the "forward" screen, one hybrid consisted of the DNA binding domain of the yeast transcriptional activator Gal4 fused to a portion of the HPS protein. The other hybrid consisted of the Gal4 activator domain fused to "prey" protein sequences encoded by a mammalian cDNA library. In the "reverse" screen, the portion of the HPS protein was fused to the Ga14 activator domain, and the prey protein sequences of the mammalian cDNA library were fused to the DNA binding domain, but the assay was otherwise identically performed.

Each of the aforementioned vectors was then inserted into complementary (a and a) mating types of yeast using methodologies known within the art. See e.g., Chien, et al., 1991. *Proc. Nati. Acad. Sci. USA* 88:9578–9581. Mating was carried out so as to facilitate the expression of both vector constructs within the same yeast cells, thus allowing the interaction to occur. Interaction between the bait and prey domains led to transcriptional activation of reporter genes containing cis-binding elements for Ga14. The reporter genes encoding the indicator protein β-galactosidase and metabolic markers for uracil and histidine auxotrophy, were included in specific fashion in one or the other of the yeast strains used in the mating. In this manner, yeast were selected for successful mating, expression of both fusion constructs and expression of the HPS protein or HPS protein-IPs. Yeast clones which contained interacting proteins were selected and cultured in individual wells of microtiter plates. The plasmids containing the HPS protein-IP sequences were then isolated and characterized.

The prey cDNAs were obtained from a human fetal brain cDNA library of 1×10$^7$ independent isolates (Catalog No. HL4029AH; Clonentech, Palo Alto, Calif.). The library was synthesized from Xhol-dT$_{15}$-primed fetal brain mRNA (from five male/female 19–22 week fetuses) which was then directionally cloned into either pAD-GAL4 (a yeast Gal4 activation domain cloning vector including the LEU2 gene for selection in yeast deficient in leucine biosynthesis) or pBD-GAL4 (a yeast Gal4 DNA-binding domain cloning vector including the TRP1 gene for selection in yeast deficient in tryptophane biosynthesis).

One forward screen was utilized to test the interaction of prey cDNA products against an array of bait proteins, one of which was encoded by the HPS protein nucleotide sequence [GenBank Accession Number u65676] of nucleotides 210–1292 (hereinafter bait fragment 210–1292). Bait fragment 210–1292 was then amplified from the full-length HPS protein cDNA by PCR amplification by standard techniques. The amplified fragment was ligated into the BamHI and EcoRI restriction sites of pGBT9BS (see e.g., Yang, et al., 1995. *Nucl. Acids Res.* 23:1152–1156). The sequences were confirmed by nucleic acid sequencing to ascertain that the PCR amplification reproduced an accurate copy of the sequence. This test determined that as predicted, the sequence encoded an interacting domain identical to the human HPS protein.

Three reverse screens were utilized to test the interaction of prey cDNA products against an array of bait proteins. The fragments 210–1292, 1272–2306, and 1272–2357, respectively, were amplified from the full-length HPS protein cDNA by PCR amplification by standard techniques. The amplified fragments were then cloned into the vector pGAD-GH (Clonentech). The sequences were confirmed by nucleic acid sequencing to ascertain that the PCR amplification reproduced an accurate copy of the sequence. This test determined that as predicted, the sequence encoded an interacting domain identical to the human HPS protein.

In the forward screen, the nucleic acid encoding the introduced bait was expressed by lithium acetate/polyethylene glycol transformation (see e.g., Ito, et al., 1983. *J. Bacteriol.* 153:163–168) into the yeast strain YULH (mating type a, ura3, his3, lys2, Ade2, trp1, leu2, gal4, gal80, GAL1-URA3, GAL1-lacZ)(forward screen); while the prey sequences were introduced by transformation into the yeast strain N106r (mating type a, ura3, his3, ade2, trp1, leu2, gal4, gal80, cyh$^r$, Lys2::GAL1$_{UAS}$-IS3$_{TATA}$-HIS3, ura3::GAL1$_{USA}$-GAL$_{TATA}$-lacZ). For the reverse screens, baits were transformed into N106r and preys into YULH.

The two transformed populations were then mated utilizing standard methods known within the art (see e.g., Sherman, et al., 1991. Getting Started with Yeast, Vol. 194 (Academic Press, New York, N.Y.)). In brief, cells were grown until reaching a mid-to-late log phase within media which selected for the presence of the appropriate plasmids. The two mating strains (a and a) were then diluted in YAPD media (see Id.) filtered onto nitrocellulose membranes and incubated at 30° C. for 6–8 hours. The cells were then transferred to media selective for the desired diploids (i.e., yeast possessing reporter genes for β-galactosidase, uracil auxotrophy, and histidine auxotrophy, as well as expressing the vectors encoding the bait and prey). The mating products were plated on synthetic complete (SC) media (see Kaiser, Michaelis & Mitchell, Eds., 1994. *Methods in Yeast Genetics*, 1994 *Ed.* (Cold Spring Harbor Laboratory Press, New York, N.Y.) lacking adenine and lysine (to select for successful mating), leucine and tryptophan (to select for expression of genes encoded by both the bait and prey plasmids), and uracil and histidine (to select for protein interactions). This medium is hereinafter referred to as SCS medium, for SC Selective medium.

Selected clones were subsequently examined for expression of β-galactosidase to confirm the formation of an HPS protein•HPS protein-IP interaction. Filter-lift assays for β-galactosidase were then performed as per a modification of the protocol of Breeden & Nasmyth, 1985. *Cold Spring Harbor Quant. Biol.* 50:643–650. Colonies were patch-plated onto SCS plates, grown overnight, and replica-plated onto Whatman No. 1 filters. The filters were then examined for β-galactosidase activity (i.e., colonies which were "positive" turned a visible blue color).

The cells contained within colonies which were "positive" for protein interaction contained a mixture of DNA-binding and activation-domain plasmids. These cells were regrown as single isolates in the individual wells of 96-well microtitration plates. Approximately 10 μl of each selected isolate was lysed, the inserts within the pAD-GAL4 or pGAD-GH for the activation domain plasmids and pBD-GAL4 or pGBT9BS plasmids were PCR amplified using primers specific for the flanking sequences of each vector and approximately 300 nucleotides (of what would be the protein's amino-terminus following translation) was determined using an ABI 377 sequenator. Comparison to known sequences was made using the "BLAST" program publicly-available through the National Center for Biotechnology Information. A summary of the HPS protein and HPS protein-IP interacting domains and identified isolates is shown in Table I, infra.

In the forward screening assays, two unique isolates were identified as novel sequences. The determined nucleic acid sequences and corresponding inferred amino acid sequences of the identical ESTs cg49368.b1; cg49367.h11; cg49424.c10 (hereinafter HPIP1) and cg Hs2950_0 (hereinafter HN1 homolog) are shown in FIGS. 1 and 2, respectively.

In the three reverse screening assays, seven isolates were found to be identical to published proteins.

1. Identified sequences interacting with the HPS protein domain comprised of nucleotides 1272–2306 include those identical to:

(i) the 14-3-3 protein (eta) sequence (GenBank Accession Number X80536) starting at nucleotide 764 (corresponds to the c-terminal region of the protein which is translated from nucleotides 192–932) and (ii) nuclear factor NF90 (GenBank Accession Number U10324) starting at nucleotide 1930 (corresponds to the c-terminal region of the protein which is translated from nucleotides 265–2280).

2. Two identified sequence interacting with the HPS protein domain 1272–2357 were demonstrated to be identical to:

(i) the 14-3-3 protein (eta) sequence (GenBank Accession Number X80536) starting at nucleotide 764 (corresponds to the c-terminal region of the protein which is translated from nucleotides 192–932) and (ii) CDK2 sequence (GenBank Accession Number X61622) starting at nucleotide 4 (the protein is translated from nucleotides 1–897).

3. In addition, the four identified sequence interacting with the HPS protein domain 210–1292 were demonstrated to be identical to:

(i) human Hrs (GenBank Accession Number D84064) starting at nucleotides 98 and 100 (the protein translated from nucleotides 61–2394);

(ii) BMK1 alpha sequence (GenBank Accession Number U29725) starting at nucleotide 2431 (corresponds to the c-terminal region of the protein which is translated from nucleotides 222–2672);

(iii) atrophin-1 sequence (GenBank Accession Number U23851) starting at nucleotide 2649 (corresponds to the carboxyl-terminal region of the protein which is translated from nucleotides 74–3628) and (iv) DGS-1 sequence (GenBank Accession Number L77566) starting at nucleotides 16 and 27 (the protein is translated from nucleotides 1–1698).

TABLE I

Protein Interactions with HPS Protein Identified by Yeast Two-Hybrid Screens

| Activating Protein Acc. No. | Activating Region b.p. | Binding Protein Acc. No. | ORF of HPS-IP | Binding Region b.p. | Iso lates | Screen | Remarks (e.g. putative Function of HPS-IP) | LYST-IP** |
|---|---|---|---|---|---|---|---|---|
| HPS U65676 | 1272–2306 1272–2357 | 14-3-3 eta X80536 | 192–932 | 764–* 764–* (c-term.) | 1 1 | reverse reverse | Vesicular trafficking and signal tranduction | LYST IP 14-3-3 protein: Interaction start at nt 185, 221, 290, 299, 308, 322, 342, 352 LYST IP 14-3-3 beta (HS1) protein: Binding region nt 465 |
| HPS U65676 | 210–1292 | Hrs D84064 | 61–2394 | 98–* 100–* | 1 1 | reverse | Vesicular trafficking and signal tranduction | LYST IP Interaction start at nt 309 |
| HPS U65676 | 210–1292 | BMK1 alpha U29725 | 222–2280 | 2431–* (c-term.) | 2 | reverse | signal transduction | LYST IP Interaction start at nt 2121 and 2431 |
| HPS U65676 | 1272–2357 | CDK2 X61622 | 1–897 | 4–* | 1 | reverse | Cell cycle regulation | — |
| HPS U65676 | 1272–2306 | NF90 U10324 | 265–2280 | 1930–* (c-term.) | 1 | reverse | Large subunit of the nuclear factor of activated T cells; substrate for DNA-dependent protein kinase | — |
| HPS U65676 | 210–1292 | Atrophin I U23851 | 74–3628 | 2649–* (c-term.) | 1 | reverse | Causes dentatorubral pallidoluysian atrophy (DRPLA, Smith's | LYST IP Interaction start at nt 2659 |

TABLE I-continued

Protein Interactions with HPS Protein Identified by Yeast Two-Hybrid Screens

| Activating Protein Acc. No. | Activating Region b.p. | Binding Protein Acc. No. | ORF of HPS-IP | Binding Region b.p. | Iso lates | Screen | Remarks (e.g. putative Function of HPS-IP) | LYST-IP** |
|---|---|---|---|---|---|---|---|---|
| HPS U65676 | 210–1292 | DGS-1 L77566 | 1–1698 | 16–* 27–* | 2 1 | reverse | disease). Vesicle transport? Novel gene from developmental defect DiGeorge syndrome (DGS) critical region (22q11). | LYST IP Interaction start at nt 454 |
| HPIP1 (cg49367.c1, cg49367.b1, cg49424.e9) | 1–* | HPS U65676 | 1–519 | 210–1292 | 3 | forward | ? | — |
| HN1 homolog (cgHs2950_0) | 22–* | HPS U65676 | 106–564 | 210–1292 | 1 | forward | expressed in homopoietic and brain tissues | — |

**See U.S. Patent Application No., Filed April 3, 1998, or PCT Patent Application, filed March, 1999.

(b) Verification of the Specificity of HPS Protein•HPS Protein-IP Interactions

To ascertain the overall degree of specificity of the bait:prey interaction, two general assays were first performed. In the first instance, yeast cells were created that express the individual plasmids encoding the binding domain fusions of the above mentioned genes (see Table I). These yeast cells were grown overnight, and examined for growth. No growth was found for all proteins tested, confirming that they were not "self-activating" proteins, that is, these proteins require interaction with a second protein domain for a functional activation complex.

To recapitulate the detected interactions in the forward screen and further demonstrate their specificity, the isolated bait plasmid for HPS were used to transform yeast strain YULH (mating type a). The interacting domains from HPIP1 and human HN1 homolog protein were transformed into strain N106r (mating type alpha). The transformants were reamplified, and a mating performed to recapitulate the identified HPS•HPS-IP interactions. HPS complexed specifically with HPIP1 and human HN1 homolog protein. It did not react non-specifically with the vector.

In the second instance, plasmids containing HPIP1 and human HN1 homolog protein inserts were transformed into strain YULH (mating type a) and mated with yeast strain N106r (mating type alpha) expressing proteins other than HPS protein. Promiscuous binders, that is, inserts able to bind with many other proteins in a non-specific fashion, would interact non-specifically with non-HPS protein domains, and would be discarded as non-specific interactants. None of the interactants showed binding to protein other than HPS protein.

To recapitulate the detected interactions in the reverse screen, and further demonstrate their specificity, the isolated bait plasmid for HPS were used to transform yeast strain N106r (mating type alpha). The interacting domains from 14-3-3 eta, Hrs, BMK1 alpha, CDK2, NF90, Atrophin-1, DGS-I were transformed into strain YULH (mating type a). The transformants were reamplified, and a mating performed to recapitulate the identified interactions. HPS complexed specifically 14-3-3 eta, Hrs, BMK1 alpha, CDK2, NF90, Atrophin-1, DGS-I. It did not react non-specifically with the vector.

In the second instance, plasmids containing 14-3-3 eta, Hrs, BMK1 alpha, CDK2, NF90, Atrophin-1, DGS-I inserts were transformed into strain YULH (mating type a) and mated with yeast strain N106r (mating type alpha) expressing proteins other than HPS. Promiscuous binders, that is, inserts able to bind with many other proteins in a non-specific fashion, would interact non-specifically with non-HPS protein domains, and would be discarded as non-specific interactants. None of the interactants showed binding to protein other than HPS protein.

(c) Analysis of Novel Sequences

The general procedure for the identity searches of the sequences encoding human EST were performed using publicly-available EST databases such as the National Center for Biotechnology Information (N.C.B.I.) BlastN 2.0 program. See Altschul, et al., 1990. J. Mol. Biol. 215:403–410. The BlastN 2.0 program translates the DNA sequence in all six reading frames and compares the translated protein sequence with those within protein databases. The statistical significance is estimated under the assumption that the equivalent of one entire reading frame in the query sequence codes for protein and that significant alignments will involve only coding reading frames. Only those sequences which produce high-scoring segment pairs are shown in the BlastN 2.0 program results.

Additionally, the sequence was analyzed for open reading frames (ORFs) using proprietary software which translates the DNA sequence in all six reading frames of the (assembled) DNA sequence using the standard genetic code. The interacting EST was obtained from directionally-cloned libraries, and thus the direction of translation of the assembled EST is known to be in the 5' to 3' orientation. Within the translations obtained, all ORFs found in frames 1–3 were analyzed. ORFs which were found to be comprised of: (i) amino acid sequences greater than 50 amino acids which followed an initiator codon or (ii) an ORF with no initiator methionine at the 5'-terminus were determined to be possible protein products, and were compared to sequences in protein data bases using the BlastP program.

(i) HPIP1

Three identical clones (cg49368.b1, cg49368.h11, and cg49424.c10) were identified as HPS interactants in this invention. The identified prey sequence of 619 nucleotides (herein referred to as HPIP1) was 98% identical to soares melanocyte EST AA42564 (starting at nucleotide 287) and 97% identical to EST 384114 (starting at nucleotide 149). However, since a 5' extension with either of these ESTs would change the ORF of the putative HPIP1 protein, HPIP1 was not be extended in either direction. The interaction of HPIP1 with HPS protein starts at nucleotide 1.

An open reading frame (ORF) of 173 amino acids (nucleotides 1–519) could be translated and the resulting protein was designated HPIP1. A BlastP search with the HPIP1 amino acid sequence showed the 62% similarities to the c-terminus of the 1007 amino acid EG0003.5 protein of *Drosophila melanogaster* (TREMBLNEW-ACC E1331653). Since the ORF has no methionine start codon, it is likely that it represents the caHPSoxy-terminal part of a longer, novel protein. The HPIP1 nucleotide and amino acid sequences are illustrated in FIG. 1 (SEQ ID NOS:1 and 2, respectively).

(ii) HN1 Homolog Protein

The identified prey sequence of 729 nucleotides (cgHs2950—0; herein referred to as HN1 homolog protein) was 82% identical to mouse HN1 (Hn1) mRNA See Tang, et al., 1997. *Mammalian Genome* 8:695–696. The interaction of HN1 homolog protein with HPS protein starts at nucleotide 22.

An open reading frame (ORF) of 153 amino acids (nucleotides 106–564) could be translated and the resulting protein was designated HN1 homolog. A BlastP search with the amino acid sequence showed 83% similarities and 79% identities to mouse hematological and neurological expressed sequence 1 (HN1, 154 amino acids; SPTREMBL-ACC:P97825; see Tang, et al., 1997, *Mammalian Genome* 8:695–696). Thus, this HPS protein interactant represents a human homolog of the mouse HN1 protein. The amino acid in position 126 could be Met (ATG), Leu (TTG), Val (GTG), or Leu (CTG).

Mouse Hn1 is expressed in many fetal and adult tissues. The highest levels of expression are found in hemopoietic cells, including day 10 yolk sac blood islands-derived circulating erythroblasts, day 13 fetal liver, adult bone marrow and spleen. The expression is also very high in day 17 fetal brain, while the expression in adult brain is considerably lower (see Tang et al., 1997. *Mammalian Genome* 8:695–696). The HN1 homolog protein nucleotide and amino acid sequences are illustrated in FIG. 2 (SEQ ID NOS:3 and 4, respectively).

It should be noted that the present invention is not to be limited in scope by the specific embodiments disclosed herein. Indeed, various modifications of the present invention, in addition to those described herein, will become readily apparent to those individuals skilled in the relevant arts from the foregoing descriptions and accompanying figures. Such modifications are intended to fall within the scope of the appended claims. In addition, various publications are cited herein and their disclosures are hereby incorporated by reference in their entirety.

What is claimed is:

1. A purified complex of the Hermansky-Pudlak Syndrome ("HPS") protein of SEQ ID NO: 6 and an Hermansky-Pudlak Syndrome protein-Interacting protein ("HPS-IP") protein, wherein said HPS-IP protein is selected from the group consisting of a 14-3-3 eta polypeptide comprising the amino acid sequence of SEQ ID NO: 8, a Hrs polypeptide comprising the amino acid sequence of SEQ ID NO: 10, a BMK1 alpha kinase polypeptide comprising the amino acid sequence of SEQ ID NO: 12, a CDK2 polypeptide comprising the amino acid sequence of SEQ ID NO: 14, a Nuclear factor NF90 polypeptide comprising the amino acid sequence of SEQ ID NO: 16, an Atrophin-1 polypeptide comprising the amino acid sequence of SEQ ID NO: 18, a DGS-I polypeptide comprising an amino acid sequence encoded by SEQ ID NO: 19, an HPIP1 polypeptide comprising the amino acid sequence of SEQ ID NO: 2 and a human HN1 homolog protein comprising the amino acid sequence of SEQ ID NO: 4.

2. The purified complex of claim 1, wherein said proteins are recombinantly expressed proteins.

3. A purified complex selected from the group consisting of a complex of a derivative of the Hermansky-Pudlak Syndrome protein of SEQ ID NO: 6 and an Hermansky-Pudlak Syndrome protein-Interacting protein, a complex of the Hermansky-Pudlak Syndrome protein of SEQ ID NO: 6 and a derivative of an HPS-IP protein, and a complex of a derivative of the Hermansky-Pudlak Syndrome protein of SEQ ID NO: 6 and a derivative of an HPS-IP protein, wherein the derivative of the Hermansky-Pudlak Syndrome protein of SEQ ID NO: 6 forms a complex with a native, wild-type HPS-IP protein and the derivative of the HPS-IP protein forms a complex with the native, wild-type Hermansky-Pudlak Syndrome protein of SEQ ID NO: 6, in which the HPS-IP is selected from the group consisting of a 14-3-3 eta polypeptide comprising the amino acid sequence of SEQ ID NO: 8, a Hrs polypeptide comprising the amino acid sequence of SEQ ID NO: 10, a BMK1 alpha kinase polypeptide comprising the amino acid sequence of SEQ ID NO: 12, a CDK2 polypeptide comprising the amino acid sequence of SEQ ID NO: 14, a Nuclear factor NF90 polypeptide comprising the amino acid sequence of SEQ ID NO: 16, an Atrophin-1 polypeptide comprising the amino acid sequence of SEQ ID NO: 18, a DGS-I polypeptide comprising an amino acid sequence encoded by SEQ ID NO: 19, an HPIP1 polypeptide comprising the amino acid sequence of SEQ ID NO: 2 and a human HN1 homolog protein comprising the amino acid sequence of SEQ ID NO: 4.

4. The purified complex of claim 3, wherein said derivative of the Hermansky-Pudlak Syndrome protein of SEQ ID NO: 6 and/or the HPS-IP protein is fluorescently labeled.

5. The complex of claim 1, wherein said HPS-IP protein is a 14-3-3 eta polypeptide comprising the amino acid sequence of SEQ ID NO: 8.

6. The complex of claim 1, wherein said HPS-IP protein is a Hrs polypeptide comprising the amino acid sequence of SEQ ID NO: 10.

7. The complex of claim 1, wherein said HPS-IP protein is a BMK1 alpha kinase polypeptide comprising the amino acid sequence of SEQ ID NO: 12.

8. The complex of claim 1, wherein said HPS-IP protein is a CDK2 polypeptide comprising the amino acid sequence of SEQ ID NO: 14.

9. The complex of claim 1, wherein said HPS-IP protein is nuclear factor NF90 polypeptide comprising the amino acid sequence of SEQ ID NO: 16.

10. The complex of claim 1, wherein said HPS-IP protein is a Atrophin-1 polypeptide comprising the amino acid sequence of SEQ ID NO: 18.

11. The complex of claim 1, wherein said HPS-IP protein is a DGS-I polypeptide comprising an amino acid sequence encoded by SEQ ID NO: 19.

12. The complex of claim 1, wherein said HPS-IP protein is a HPIP1 polypeptide comprising the amino acid sequence of SEQ ID NO: 2.

13. The complex of claim 1, wherein said HPS-IP protein is a human HN1 homolog polypeptide comprising the amino acid sequence of SEQ ID NO: 4.

14. The complex of claim 3, wherein said HPS-IP derivative includes the polypeptide sequence encoded by nucleotides 764–932 of SEQ ID NO: 7.

15. The complex of claim 3, wherein said HPS-IP derivative includes the polypeptide sequence encoded by nucleotides 100–2394 of SEQ ID NO: 9.

16. The complex of claim 3, wherein said HPS-IP derivative includes the polypeptide sequence encoded by nucleotides 4–897 of SEQ ID NO: 11.

17. The complex of claim 3, wherein said HPS-IP derivative includes the polypeptide sequence encoded by nucleotides 1930–2280 of SEQ ID NO: 15.

18. The complex of claim 3, wherein said HPS-IP derivative includes the polypeptide sequence encoded by nucleotides 2649–3628 of SEQ ID NO: 17.

19. The complex of claim 3, wherein said HPS-IP derivative includes the polypeptide sequence encoded by nucleotides 27–1698 of SEQ ID NO: 19.

20. The complex of claim 3, wherein said HPS-IP derivative includes the polypeptide sequence encoded by nucleotides 22–564 of SEQ ID NO:3.

21. The complex of claim 3, wherein said HPS derivative includes the polypeptide sequence encoded by nuclcotides 1272–2306 SEQ ID NO: 5.

22. A purified complex selected from the group consisting of a complex of a fragment of the Hermansky-Pudlak Syndrome protein of SEQ ID NO: 6 and an Hermansky-Pudlak Syndrome protein-Interacting protein, a complex of the Hermansky-Pudlak Syndrome protein of SEQ ID NO: 6 and a fragment of an HPS-IP protein, and a complex of a fragment of the Hermansky-Pudlak Syndrome protein of SEQ ID NO: 6 and a fragment of an HPS-IP protein, wherein the fragment of the Hermansky-Pudlak Syndrome protein of SEQ ID NO: 6 forms a complex with a native, wild-type HPS-IP protein and the fragment of the HPS-IP protein forms a complex with the native, wild-type Hermansky-Pudlak Syndrome protein of SEQ ID NO: 6, in which the HPS-IP is selected from the group consisting of a 14-3-3 eta polypeptide comprising the amino acid sequence of SEQ ID NO: 8, a Hrs polypeptide comprising the amino acid sequence of SEQ ID NO: 10, a BMK1 alpha kinase polypeptide comprising the amino acid sequence of SEQ ID NO: 12, a CDK2 polypeptide comprising the amino acid sequence of SEQ ID NO: 14, a Nuclear factor NF90 polypeptide comprising the amino acid sequence of SEQ ID NO: 16, an Atrophin-1 polypeptide comprising the amino acid sequence of SEQ ID NO: 18, a DGS-I polypeptide comprising an amino acid sequence encoded by SEQ ID NO: 19, an HPIP1 polypeptide comprising the amino acid sequence of SEQ ID NO: 2 and a human HN1 homolog protein comprising the amino acid sequence of SEQ ID NO: 4.

23. The purified complex of claim 22, wherein said fragment of the Hermansky-Pudlak Syndrome protein of SEQ ID NO: 6 and/or the HPS-IP protein is fluorescently labeled.

24. The complex of claim 22, wherein said HPS-IP fragment includes the polypeptide sequence encoded by nucleotides 764–932 of SEQ ID NO: 7.

25. The complex of claim 22, wherein said HPS-IP fragment includes the polypeptide sequence encoded by nucleotides 100–2394 of SEQ ID NO: 9.

26. The complex of claim 22, wherein said HPS-IP fragment includes the polypeptide sequence encoded by nucleotides 4–897 of SEQ ID NO: 11.

27. The complex of claim 22, wherein said HPS-IP fragment includes the polypeptide sequence encoded by nucleotides 1930–2280 of SEQ ID NO: 15.

28. The complex of claim 22, wherein said HPS-IP fragment includes the polypeptide sequence encoded by nucleotides 2649–3628 of SEQ ID NO: 17.

29. The complex of claim 22, wherein said HPS-IP fragment includes the polypeptide sequence encoded by nucleotides 27–1698 of SEQ ID NO: 19.

30. The complex of claim 22, wherein said HPS-IP fragment includes the polypeptide sequence encoded by nucleotides 22–564 of SEQ ID NO:3.

31. The complex of claim 22, wherein said HPS fragment includes the polypeptide sequence encoded by nucleotides 1272–2306 SEQ ID NO: 5.

* * * * *

SEQUENCE LISTING

<160> NUMBER OF SEQ ID NOS: 19

<210> SEQ ID NO 1
<211> LENGTH: 619
<212> TYPE: DNA
<213> ORGANISM: Homo sapiens
<220> FEATURE:
<221> NAME/KEY: CDS
<222> LOCATION: (1)..(519)

<400> SEQUENCE: 1

```
ggc acg aga ctc agt ata aat cca aat aac cat tct tgg tta att atc      48
Gly Thr Arg Leu Ser Ile Asn Pro Asn Asn His Ser Trp Leu Ile Ile
  1               5                  10                  15 cag gca gat att tac ttt gca acg aat cag tat tca gca gct ctt cac      96
Gln Ala Asp Ile Tyr Phe Ala Thr Asn Gln Tyr Ser Ala Ala Leu His
             20                  25                  30 tat tac ctc cag gca gga gct gtg tgt tct gac ttc ttt aac aag gct     144
Tyr Tyr Leu Gln Ala Gly Ala Val Cys Ser Asp Phe Phe Asn Lys Ala
         35                  40                  45 gtg ccc cct gat gtt tat aca gac cag gta ata aaa cga atg ata aaa     192
Val Pro Pro Asp Val Tyr Thr Asp Gln Val Ile Lys Arg Met Ile Lys
     50                  55                  60 tgt tgt tct ttg ctg aat tgc cac aca cag gtg gct att tta tgt cag     240
Cys Cys Ser Leu Leu Asn Cys His Thr Gln Val Ala Ile Leu Cys Gln
 65                  70                  75                  80 ttc ctc aga gaa att gac tac aaa aca gcg ttt aaa tct ctg caa gaa     288
Phe Leu Arg Glu Ile Asp Tyr Lys Thr Ala Phe Lys Ser Leu Gln Glu
                 85                  90                  95 caa aac agt cat gat gct atg gac tcc tac tac gac tac ata tgg gat     336
Gln Asn Ser His Asp Ala Met Asp Ser Tyr Tyr Asp Tyr Ile Trp Asp
            100                 105                 110 gtt acc att ttg gaa tac ttg act tat ctt cat cat aaa aga gga gaa     384
Val Thr Ile Leu Glu Tyr Leu Thr Tyr Leu His His Lys Arg Gly Glu
        115                 120                 125
```

-continued

```
aca gat aaa aga caa att gca atc aaa gcc atc ggc cag aca gag ttg      432
Thr Asp Lys Arg Gln Ile Ala Ile Lys Ala Ile Gly Gln Thr Glu Leu
        130                 135                 140 aat gca agc aat cca gaa gaa gtg tta cag ctg gca gcg cag aga agg      480
Asn Ala Ser Asn Pro Glu Glu Val Leu Gln Leu Ala Ala Gln Arg Arg
145                 150                 155                 160 aaa aaa aag ttt ctc caa gca atg gca aaa ctt tac ttt taagcagtta      529
Lys Lys Lys Phe Leu Gln Ala Met Ala Lys Leu Tyr Phe
                165                 170 aattttttta actttattt ttaaacaat gggctaaaaa taaacagtat taaaagggta      589
agtttatata atacaaaaaa aaaaaaaaaa                                    619
```

<210> SEQ ID NO 2
<211> LENGTH: 173
<212> TYPE: PRT
<213> ORGANISM: Homo sapiens

<400> SEQUENCE: 2

```
Gly Thr Arg Leu Ser Ile Asn Pro Asn His Ser Trp Leu Ile Ile
  1               5                  10                  15

Gln Ala Asp Ile Tyr Phe Ala Thr Asn Gln Tyr Ser Ala Ala Leu His
                 20                  25                  30

Tyr Tyr Leu Gln Ala Gly Ala Val Cys Ser Asp Phe Asn Lys Ala
             35                  40                  45

Val Pro Pro Asp Val Tyr Thr Asp Gln Val Ile Lys Arg Met Ile Lys
     50                  55                  60

Cys Cys Ser Leu Leu Asn Cys His Thr Gln Val Ala Ile Leu Cys Gln
 65                  70                  75                  80

Phe Leu Arg Glu Ile Asp Tyr Lys Thr Ala Phe Lys Ser Leu Gln Glu
                 85                  90                  95

Gln Asn Ser His Asp Ala Met Asp Ser Tyr Tyr Asp Tyr Ile Trp Asp
            100                 105                 110

Val Thr Ile Leu Glu Tyr Leu Thr Tyr Leu His His Lys Arg Gly Glu
        115                 120                 125

Thr Asp Lys Arg Gln Ile Ala Ile Lys Ala Ile Gly Gln Thr Glu Leu
    130                 135                 140

Asn Ala Ser Asn Pro Glu Glu Val Leu Gln Leu Ala Ala Gln Arg Arg
145                 150                 155                 160

Lys Lys Lys Phe Leu Gln Ala Met Ala Lys Leu Tyr Phe
                165                 170
```

<210> SEQ ID NO 3
<211> LENGTH: 729
<212> TYPE: DNA
<213> ORGANISM: Homo sapiens
<220> FEATURE:
<221> NAME/KEY: misc_feature
<222> LOCATION: (481)
<223> OTHER INFORMATION: n may be a, c, g, or t
<221> NAME/KEY: misc_feature
<222> LOCATION: (682)
<223> OTHER INFORMATION: n may be a, c, g, or t

<400> SEQUENCE: 3

```
ctcctgcagc ggtggtcggc tgttgggtgt ggagtttccc agcgcccctc gggtccgacc     60
ctttgagcgt tctgctccgg cgccactacc tcgctcctcg gcgccatgac cacaaccacc    120
accttcaagg gagtcgaccc caacagcagg aatagctccc gagttttgcg gcctccaggt    180
```

-continued

```
ggtggatcca attttcatt aggttttgat gaaccaacag aacaacctgt gaggaagaac     240
aaaatggcct ctaatatctt tgggacacct gaagaaaatc aagcttcttg ggccaagtca     300
gcaggtgcca agtctagtgg tggcagggaa gacttggagt catctggact gcagagaagg     360
aactcctctg aagcaagctc cggagacttc ttagatctga agggagaagg tgatattcat     420
gaaaatgtgg acacagactt gccaggcagc ctggggcaga gtgaagagaa gcccgtgcct     480
ntgcgcctgt gcccagcccg gtgccccggc cccagtgcca tccagaagaa atcccctggc     540
ggcaagtcca gcctcgtctt gggttagctc tgactgtcct gaacgctgtc gttctgtctg     600
tttcctccat gcttgtgaac tgcacaactt gagcctgact gtacatctct tggatttgtt     660
tcattaaaaa gaagcacttt angtaaaaaa aaaaaaaaaa aaaaaaaaaa aaaaaaaaaa     720
aaaaaacaa                                                             729
```

<210> SEQ ID NO 4
<211> LENGTH: 153
<212> TYPE: PRT
<213> ORGANISM: Homo sapiens
<220> FEATURE:
<221> NAME/KEY: VARIANT
<222> LOCATION: (126)
<223> OTHER INFORMATION: Wherein Xaa is Leu or Met or Val

<400> SEQUENCE: 4

```
Met Thr Thr Thr Thr Thr Phe Lys Gly Val Asp Pro Asn Ser Arg Asn
 1               5                  10                  15

Ser Ser Arg Val Leu Arg Pro Pro Gly Gly Ser Asn Phe Ser Leu
             20                  25                  30

Gly Phe Asp Glu Pro Thr Glu Gln Pro Val Arg Lys Asn Lys Met Ala
         35                  40                  45

Ser Asn Ile Phe Gly Thr Pro Glu Glu Asn Gln Ala Ser Trp Ala Lys
     50                  55                  60

Ser Ala Gly Ala Lys Ser Ser Gly Gly Arg Glu Asp Leu Glu Ser Ser
 65                  70                  75                  80

Gly Leu Gln Arg Arg Asn Ser Ser Glu Ala Ser Ser Gly Asp Phe Leu
                 85                  90                  95

Asp Leu Lys Gly Glu Gly Asp Ile His Glu Asn Val Asp Thr Asp Leu
            100                 105                 110

Pro Gly Ser Leu Gly Gln Ser Glu Glu Lys Pro Val Pro Xaa Arg Leu
        115                 120                 125

Cys Pro Ala Arg Cys Pro Gly Pro Ser Ala Ile Gln Lys Lys Ser Pro
    130                 135                 140

Gly Gly Leu Ser Ser Leu Val Leu Gly
145                 150
```

<210> SEQ ID NO 5
<211> LENGTH: 3673
<212> TYPE: DNA
<213> ORGANISM: Homo sapiens

<400> SEQUENCE: 5

```
gggcgctgtg cgcgccgcga tccggtacgt gggcctccgg gctgtcccct ctggggcga      60 tcctccctcc ggagcccccc ttcaaccctc ccggaagtga ggaccaggga tgctgtgctg     120
ctctcccatg agccagtcac cgagtcggtc tgctgcagcc ctttctgaac ctctggccgt     180
ctggatgctc cactgtgctt gccaagatga agtgcgtctc ggtggccact gagggcgcag     240
aggtcctctt ctactggaca gatcaggagt ttgaagagag tctccggctg aagttcgggc     300
```

```
agtcagagaa tgaggaagaa gagctccctg ccctggagga ccagctcagc accctcctag       360
ccccggtcat catctcctcc atgacgatgc tggagaagct ctcggacacc tacacctgct       420
tctccacgga aaatggcaac ttcctgtatg tccttcacct gtttggagaa tgcctgttca       480
ttgccatcaa tggtgaccac accgagagcg aggggacct cgcggcggaag ctgtatgtgc       540 tcaagtacct gtttgaagtg cactttgggc tggtgactgt ggacggtcat cttatccgaa       600
aggagctgcg gccccagac ctggcgcagc gtgtccagct gtgggagcac ttccagagcc       660
tgctgtggac ctacagccgc ctgcgggagc aggagcagtg cttcgccgtg gaggccctgg       720
agcgactgat tcaccccag ctctgtgagc tgtgcataga ggcgctggag cggcacgtca       780
tccaggctgt caacaccagc cccgagcggg gaggcgagga ggccctgcat gccttcctgc       840
tcgtgcactc caagctgctg gcattctact ctagccacag tgccagctcc ctgcgcccgg       900
ccgacctgct tgccctcatc ctcctggttc aggacctcta ccccagcgag agcacagcag       960
aggacgacat tcagccttcc ccgcggaggg cccggagcag ccagaacatc cccgtgcagc      1020
aggcctggag ccctcactcc acgggcccaa ctggggggag ctctgcagag acggagacag      1080
acagcttctc cctccctgag gagtacttca caccagctcc ttcccctggc gatcagagct      1140
caggtagcac catctggctg gagggggca ccccccccat ggatgccctt cagatagcag      1200
aggacaccct ccaaacactg gttccccact gccctgtgcc ttccggcccc agaaggatct      1260
tcctggatgc caacgtgaag gaaagctact gcccctagt gccccacacc atgtactgcc      1320 tgccctgtg gcagggcatc aacctggtgc tcctgaccag gagccccagc gcgcccctgg      1380
ccctggttct gtcccagctg atggatggct ctccatgct ggagaagaag ctgaaggaag      1440
ggccggagcc cggggcctcc ctgcgctccc agcccctcgt gggagacctg cgccagagga      1500
tggacaagtt tgtcaagaat cgaggggcac aggagattca gagcacctgg ctggagtttta      1560 aggccaaggc tttctccaaa agtgagcccg gatcctcctg ggagctgctc caggcatgtg      1620
ggaagctgaa gcggcagctc tgcgccatct accggctgaa ctttctgacc acagccccca      1680 gcagggagg cccacacctg ccccagcacc tgcaggacca agtgcagagg ctcatgcggg      1740
agaagctgac ggactggaag gacttcttgc tggtgaagag caggaggaac atcaccatgg      1800
tgtcctacct agaagacttc ccaggcttgg tgcacttcat ctatgtggac cgcaccactg      1860
ggcagatggt ggcgccttcc ctcaactgca gtcaaaagac ctcgtcggag ttgggcaagg      1920
ggccgctggc tgccttttgtc aaaactaagg tctggtctct gatccagctg gcgcgcagat      1980
acctgcagaa gggctacacc acgctgctgt tccgggaggg ggatttctac tgctcctact      2040
tcctgtggtt cgagaatgac atgggtaca aactccagat gatcgaggtg cccgtcctcc      2100
ccgacgactc agtgcctatc ggcatgctgg gaggagacta tacaggaag ctcctgcgct      2160 actacagcaa gaaccgccca accgaggctg tcaggtgcta cgagctgctg gccctgcacc      2220
tgtctgtcat ccccactgac ctgctggtgc agcaggccgg ccagctggcc cggcgcctct      2280
gggaggcctc ccgtatcccc ctgctctagg ccaaggtggc cgcagtctgc ctttgcatcc      2340
tgtcctccag ccaccttgc ttgccactgt tccccatgac gagagcctcc tgtctgcagt      2400
ggccatcctg aggatagggc agagtgccca gggtggcccc agggcttcta aaaccccacc      2460
tagaccaccc tccatgtcag gtactgagca aggccccaga tccttctctc tggaggaaga      2520
gggaagccca ggggtcctgt ttgtaaaaca acggtggcaa cagctcctct tccagagctg      2580
cctctgcctt tatcctggga gatggggagg aagccccatc tctgctgttc cctgcgtgga      2640
```

-continued

```
ggaagcccac ccagcaagct ctctcctacc ccaggtaaaa ggtgctcctt tgcctgggtt      2700
tgaattccag cgctgccact tcctctctgc acctcctggc aagtttcttc tattccccac      2760
gtttaaagcg atggcacctc cgtcccaggg tggtgtgagg attacccagt gtggtaggtg      2820
ctcaataaat gttggtcatt gttatcactg aagcccaaca tgctagtgct tctagaccct      2880
tctgtcagtg ctgataagcc cttgctaagt cccagcccct tcatgcttgg ctggcgtctg      2940
ccctagggct ggggttctca agcccctggc cctggcccag agatttggat tccttggcg       3000 gccgtggagc ccaggctttg atgtctttca aagcttctgt ggtgcgccct ggattgagaa      3060
ccaccacccg agggtacag ccccctctctt ccaaccgaga agttcctgtc cagaatggac       3120
ccagggacaa gagaccctga gagccctggg actgggagtg tctgctcctc tgagccagga      3180
ggccggtgct gggccagaga ggacggcgtg gcgaaagtca gcgtccactg cagcacagga      3240
tcagatggcc gtgtgctgtg catgcaggag cctcgccttc tgtgtcttta gtcttgagcc      3300
aaaatttgct caaaagactg atctcttcct tgcagggaac agctttgggg ctgggggaac      3360
tagaacccac atgttggtct aaaccctgag aaggtggcag tgaggaagta tcccctcagg      3420
tgactggatc tgtgttcctc cttaacatca tctgatggaa tggcaatgaa aagcgtggat      3480
tgtggaaaat acagaaaaac ataaaggaaa aaactccaat cccctgagcc caccactgtt      3540
caggacccct gcttttgtca cctactattt ccctttagtt tttagcagcg gctggatgtg      3600
atatgtctag tttaaccagt ccccttgatc tttctatata ataaataaca caggagtgaa      3660
catcctgaat cag                                                         3673
```

<210> SEQ ID NO 6
<211> LENGTH: 700
<212> TYPE: PRT
<213> ORGANISM: Homo sapiens

<400> SEQUENCE: 6

```
Met Lys Cys Val Leu Val Ala Thr Glu Gly Ala Glu Val Leu Phe Tyr
  1               5                  10                  15

Trp Thr Asp Gln Glu Phe Glu Glu Ser Leu Arg Leu Lys Phe Gly Gln
             20                  25                  30

Ser Glu Asn Glu Glu Glu Glu Leu Pro Ala Leu Glu Asp Gln Leu Ser
         35                  40                  45

Thr Leu Leu Ala Pro Val Ile Ile Ser Ser Met Thr Met Leu Glu Lys
     50                  55                  60

Leu Ser Asp Thr Tyr Thr Cys Phe Ser Thr Glu Asn Gly Asn Phe Leu
 65                  70                  75                  80

Tyr Val Leu His Leu Phe Gly Glu Cys Leu Phe Ile Ala Ile Asn Gly
                 85                  90                  95

Asp His Thr Glu Ser Glu Gly Asp Leu Arg Arg Lys Leu Tyr Val Leu
            100                 105                 110

Lys Tyr Leu Phe Glu Val His Phe Gly Leu Val Thr Val Asp Gly His
        115                 120                 125

Leu Ile Arg Lys Glu Leu Arg Pro Pro Asp Leu Ala Gln Arg Val Gln
    130                 135                 140

Leu Trp Glu His Phe Gln Ser Leu Leu Trp Thr Tyr Ser Arg Leu Arg
145                 150                 155                 160

Glu Gln Glu Gln Cys Phe Ala Val Glu Ala Leu Glu Arg Leu Ile His
                165                 170                 175

Pro Gln Leu Cys Glu Leu Cys Ile Glu Ala Leu Glu Arg His Val Ile
            180                 185                 190
```

-continued

```
Gln Ala Val Asn Thr Ser Pro Arg Gly Glu Glu Ala Leu His
        195                 200                 205
Ala Phe Leu Leu Val His Ser Lys Leu Leu Ala Phe Tyr Ser Ser His
        210                 215                 220
Ser Ala Ser Ser Leu Arg Pro Ala Asp Leu Leu Ala Leu Ile Leu Leu
225                 230                 235                 240
Val Gln Asp Leu Tyr Pro Ser Glu Ser Thr Ala Glu Asp Asp Ile Gln
                245                 250                 255
Pro Ser Pro Arg Arg Ala Arg Ser Ser Gln Asn Ile Pro Val Gln Gln
                260                 265                 270
Ala Trp Ser Pro His Ser Thr Gly Pro Thr Gly Ser Ser Ala Glu
        275                 280                 285
Thr Glu Thr Asp Ser Phe Ser Leu Pro Glu Glu Tyr Phe Thr Pro Ala
        290                 295                 300
Pro Ser Pro Gly Asp Gln Ser Ser Gly Ser Thr Ile Trp Leu Glu Gly
305                 310                 315                 320
Gly Thr Pro Pro Met Asp Ala Leu Gln Ile Ala Glu Asp Thr Leu Gln
                325                 330                 335
Thr Leu Val Pro His Cys Pro Val Pro Ser Gly Pro Arg Arg Ile Phe
                340                 345                 350
Leu Asp Ala Asn Val Lys Glu Ser Tyr Cys Pro Leu Val Pro His Thr
        355                 360                 365
Met Tyr Cys Leu Pro Leu Trp Gln Gly Ile Asn Leu Val Leu Leu Thr
        370                 375                 380
Arg Ser Pro Ser Ala Pro Leu Ala Leu Val Leu Ser Gln Leu Met Asp
385                 390                 395                 400
Gly Phe Ser Met Leu Glu Lys Lys Leu Lys Glu Gly Pro Glu Pro Gly
                405                 410                 415
Ala Ser Leu Arg Ser Gln Pro Leu Val Gly Asp Leu Arg Gln Arg Met
                420                 425                 430
Asp Lys Phe Val Lys Asn Arg Gly Ala Gln Glu Ile Gln Ser Thr Trp
        435                 440                 445
Leu Glu Phe Lys Ala Lys Ala Phe Ser Lys Ser Glu Pro Gly Ser Ser
        450                 455                 460
Trp Glu Leu Leu Gln Ala Cys Gly Lys Leu Lys Arg Gln Leu Cys Ala
465                 470                 475                 480
Ile Tyr Arg Leu Asn Phe Leu Thr Thr Ala Pro Ser Arg Gly Gly Pro
                485                 490                 495
His Leu Pro Gln His Leu Gln Asp Gln Val Gln Arg Leu Met Arg Glu
                500                 505                 510
Lys Leu Thr Asp Trp Lys Asp Phe Leu Leu Val Lys Ser Arg Arg Asn
        515                 520                 525
Ile Thr Met Val Ser Tyr Leu Glu Asp Phe Pro Gly Leu Val His Phe
        530                 535                 540
Ile Tyr Val Asp Arg Thr Thr Gly Gln Met Val Ala Pro Ser Leu Asn
545                 550                 555                 560
Cys Ser Gln Lys Thr Ser Ser Glu Leu Gly Lys Gly Pro Leu Ala Ala
                565                 570                 575
Phe Val Lys Thr Lys Val Trp Ser Leu Ile Gln Leu Ala Arg Arg Tyr
                580                 585                 590
Leu Gln Lys Gly Tyr Thr Thr Leu Leu Phe Arg Glu Gly Asp Phe Tyr
        595                 600                 605
```

```
Cys Ser Tyr Phe Leu Trp Phe Glu Asn Asp Met Gly Tyr Lys Leu Gln
    610                 615                 620
Met Ile Glu Val Pro Val Leu Ser Asp Asp Ser Val Pro Ile Gly Met
625                 630                 635                 640
Leu Gly Gly Asp Tyr Tyr Arg Lys Leu Leu Arg Tyr Tyr Ser Lys Asn
                645                 650                 655
Arg Pro Thr Glu Ala Val Arg Cys Tyr Glu Leu Leu Ala Leu His Leu
            660                 665                 670
Ser Val Ile Pro Thr Asp Leu Leu Val Gln Gln Ala Gly Gln Leu Ala
        675                 680                 685
Arg Arg Leu Trp Glu Ala Ser Arg Ile Pro Leu Leu
    690                 695                 700

<210> SEQ ID NO 7
<211> LENGTH: 1730
<212> TYPE: DNA
<213> ORGANISM: Homo sapiens

<400> SEQUENCE: 7
```

| | | | | | |
|---|---|---|---|---|---|
| gaattcgcgg | cgccgagagg | gcgcgagcgg | cggcgctgcc | tgcagcctgc | agcctgcagc | 60 |
| ctccggccgg | ccggcgagcc | agtgcgcgtg | cgcggcggcg | gcctccgcag | cgaccgggga | 120 |
| gcggactgac | cggcggagg | gctagcgagc | cagcggtgtg | aggcgcgagg | cgaggccgag | 180 |
| ccgcgagcga | catgggggac | cgggagcagc | tgctgcagcg | ggcgcggctg | ccgagcagg | 240 |
| cggagcgcta | cgacgacatg | gcctccgcta | tgaaggcggt | gacagagctg | aatgaacctc | 300 |
| tctccaatga | agatcgaaat | ctcctctctg | tggcctacaa | gaatgtggtt | ggtgccaggc | 360 |
| gatcttcctg | gagggtcatt | agcagcattg | agcagaaaac | catggctgat | ggaaacgaaa | 420 |
| agaaattgga | gaaagttaaa | gcttaccggg | agaagattga | gaaggagctg | agacagtttt | 480 |
| gcaatgatgt | cctgtctctg | cttgacaagt | tcctgatcaa | gaactgcaat | gatttccagt | 540 |
| atgagagcaa | ggtgttttac | ctgaaaatga | agggtgatta | ctaccgctac | ttagcagagg | 600 |
| tcgcttctgg | ggagaagaaa | aacagtgtgg | tcgaagcttc | tgaagctgcc | tacaaggaag | 660 |
| cctttgaaat | cagcaaagag | cagatgcaac | ccacgcatcc | catccggctg | ggcctggccc | 720 |
| tcaacttctc | cgtgttctac | tatgagatcc | agaatgcacc | tgagcaagcc | tgcctcttag | 780 |
| ccaaacaagc | cttcgatgat | gccatagctg | agctggacac | actaaacgag | gattcctata | 840 |
| aggactccac | gctgatcatg | cagttgctgc | gagacaacct | caccctctgg | acgagcgacc | 900 |
| agcaggatga | agaagcagga | gaaggcaact | gaagatcctt | caggtcccct | agcccttcct | 960 |
| tcacccacca | ccccatcat | caccgattct | tccttgccac | aatcactaaa | tatctagtgc | 1020 |
| taaacctatc | tgtattggca | gcacagctac | tcagatctgc | actcctgtct | cttgggaagc | 1080 |
| agtttcagat | aaatcatggg | cattgctgga | ctgatggttg | ctttgagccc | acaggagctc | 1140 |
| cctttttgaa | ttgtgtggag | aagtgtgttc | tgatgaggca | ttttactatg | cctgttgatc | 1200 |
| tatgggaaat | ctaggcgaaa | gtaatgggga | agattagaaa | gaattagcca | accaggctac | 1260 |
| agttgatatt | taaaagatcc | atttaaaaca | agctgatagt | gtttcgttaa | gcagtacatc | 1320 |
| ttgtgcatgc | aaaaatgaat | tcaccctcc | cacctctttc | ttcaattaat | ggaaaactgt | 1380 |
| taagggaagc | tgatacagag | agacaacttg | ctcctttcca | tcagctttat | aataaactgt | 1440 |
| ttaacgtgag | gtttcagtag | ctccttggtt | ttgcctcttt | aaattatgac | gtgcacaaac | 1500 |
| cttcttttca | atgcaatgca | tctgaaagtt | ttgatacttg | taactttttt | ttttttttgg | 1560 |
| ttgcaattgt | ttaagaatca | tggatttatt | ttttgtaact | ctttggctat | tgtccttgtg | 1620 |

```
tatcctgaca gcgccatgtg tgtcagccca tgtcaatcaa gatgggtgat tatgaaatgc    1680
cagacttcta aaataaatgt tttggaattc aatgggtaaa taaatgcgac              1730
```

<210> SEQ ID NO 8
<211> LENGTH: 246
<212> TYPE: PRT
<213> ORGANISM: Homo sapiens

<400> SEQUENCE: 8

```
Met Gly Asp Arg Glu Gln Leu Leu Gln Arg Ala Arg Leu Ala Glu Gln
  1               5                  10                  15

Ala Glu Arg Tyr Asp Asp Met Ala Ser Ala Met Lys Ala Val Thr Glu
             20                  25                  30

Leu Asn Glu Pro Leu Ser Asn Glu Asp Arg Asn Leu Leu Ser Val Ala
         35                  40                  45

Tyr Lys Asn Val Val Gly Ala Arg Arg Ser Ser Trp Arg Val Ile Ser
     50                  55                  60

Ser Ile Glu Gln Lys Thr Met Ala Asp Gly Asn Glu Lys Lys Leu Glu
 65                  70                  75                  80

Lys Val Lys Ala Tyr Arg Glu Lys Ile Glu Lys Glu Leu Glu Thr Val
                 85                  90                  95

Cys Asn Asp Val Leu Ser Leu Leu Asp Lys Phe Leu Ile Lys Asn Cys
            100                 105                 110

Asn Asp Phe Gln Tyr Glu Ser Lys Val Phe Tyr Leu Lys Met Lys Gly
        115                 120                 125

Asp Tyr Tyr Arg Tyr Leu Ala Glu Val Ala Ser Gly Glu Lys Lys Asn
    130                 135                 140

Ser Val Val Glu Ala Ser Glu Ala Ala Tyr Lys Glu Ala Phe Glu Ile
145                 150                 155                 160

Ser Lys Glu Gln Met Gln Pro Thr His Pro Ile Arg Leu Gly Leu Ala
                165                 170                 175

Leu Asn Phe Ser Val Phe Tyr Tyr Glu Ile Gln Asn Ala Pro Glu Gln
            180                 185                 190

Ala Cys Leu Leu Ala Lys Gln Ala Phe Asp Asp Ala Ile Ala Glu Leu
        195                 200                 205

Asp Thr Leu Asn Glu Asp Ser Tyr Lys Asp Ser Thr Leu Ile Met Gln
    210                 215                 220

Leu Leu Arg Asp Asn Leu Thr Leu Trp Thr Ser Asp Gln Gln Asp Glu
225                 230                 235                 240

Glu Ala Gly Glu Gly Asn
                245
```

<210> SEQ ID NO 9
<211> LENGTH: 2896
<212> TYPE: DNA
<213> ORGANISM: Homo sapiens

<400> SEQUENCE: 9

```
gggcgcgcca gctcgtagca ggggagcgcc cgcggcgtcg ggtttgggct ggaggtcgcc     60
atggggcgag gcagcggcac cttcgagcgt ctcctagaca aggcgaccag ccagctcctg    120
ttggagacag attgggagtc cattttgcag atctgcgacc tgatccgcca aggggacaca    180
caagcaaaat atgctgtgaa ttccatcaag aagaaagtca acgacaagaa cccacacgtc    240
gccttgtatg ccctggaggt catggaatct gtggtaaaga actgtggcca gacagttcat    300
```

-continued

| | | | |
|---|---|---|---|
| gatgaggtgg ccaacaagca gaccatggag gagctgaagg acctgctgaa gagacaagtg | 360 |
| gaggtaaacg tccgtaacaa gatcctgtac ctgatccagg cctgggcgca tgccttccgg | 420 |
| aacgagccca agtacaaggt ggtccaggac acctaccaga tcatgaaggt ggaggggcac | 480 |
| gtctttccag aattcaaaga gagcgatgcc atgtttgctg ccgagagagc cccagactgg | 540 |
| gtggacgctg aggaatgcca ccgctgcagg gtgcagttcg gggtgatgac ccgtaagcac | 600 |
| cactgccggg cgtgtgggca gatattctgt ggaaagtgtt cttccaagta ctccaccatc | 660 |
| cccaagtttg gcatcgagaa ggaggtgcgc gtgtgtgagc cctgctacga gcagctgaac | 720 |
| aggaaagcgg agggaaaggc cacttccacc actgagctgc cccccgagta cctgaccagc | 780 |
| cccctgtctc agcagtccca gctgccccca aagagggacg agacggccct gcaggaggag | 840 |
| gaggagctgc agctggccct ggcgctgtca cagtcagagg cggaggagaa ggagaggctg | 900 |
| agacagaagt ccacgtacac ttcgtacccc aaggcgagc ccatgccctc ggcctcctca | 960 |
| gcgcccccg ccagcagcct gtactcttca cctgtgaact cgtcggcgcc tctggctgag | 1020 |
| gacatcgacc ctgagctcgc acggtatctc aaccggaact actgggagaa gaagcaggag | 1080 |
| gaggctcgca agagccccac gccatctgcg cccgtgcccc tgacgagcc ggctgcacag | 1140 |
| cctggggaag ggcacgcagc ccccaccaac gtggtggaga acccctccc ggagacagac | 1200 |
| tctcagccca ttcctccctc tggtggcccc tttagtgagc cacagttcca caatggcgag | 1260 |
| tctgaggaga gccacgagca gttcctgaag gcgctgcaga acgccgtcac caccttcgtg | 1320 |
| aaccgcatga agagtaacca catgcgggc cgcagcatca ccaatgactc ggccgtgctc | 1380 |
| tcactcttcc agtccatcaa cggcatgcac ccgcagctgc tggagctgct caaccagctg | 1440 |
| gacgagcgca ggctgtacta tgaggggctg caggacaagc tggcacagat ccgcgatgcc | 1500 |
| cgggggcgc tgagtgccct gcgcgaagag caccgggaga agcttcgccg ggcagccgag | 1560 |
| gaggcagagc gccagcgcca gatccagctg gcccagaagc tggagataat gcggcagaag | 1620 |
| aagcaggagt acctggaggt gcagaggcag ctggccatcc agcgcctgca ggagcaggag | 1680 |
| aaggagcggc agatgcggct ggagcagcag aagcagacgg tccagatgcg cgcgcagatg | 1740 |
| cccgccttcc ccctgcccta cgcccagctc caggccatgc ccgcagccgg aggtgtgctc | 1800 |
| taccagcccc cgggaccagc cagcttcccc agcaccttca gccctgccgg ctcggtggag | 1860 |
| ggctccccaa tgcacggcgt gtacatgagc cagccggccc ctgccgctgg cccctacccc | 1920 |
| agcatgccca gcactgcggc tgatcccagc atggtgagtg cctacatgta cccagcaggg | 1980 |
| gccactgggg cgcaggcggc ccccaggcc caggccggac ccaccgccag ccccgcttac | 2040 |
| tcatcctacc agcctactcc cacagcgggc taccagaacg tggcctccca ggccccacag | 2100 |
| agcctcccgg ccatctctca gcctccgcag tccagcacca tgggctacat ggggagccag | 2160 |
| tcagtctcca tgggctacca gccttacaac atgcagaatc tcatgaccac cctcccaagc | 2220 |
| caggatgcgt ctctgccacc ccagcagccc tacatcgcgg ggcagcagcc catgtaccag | 2280 |
| cagatggcac cctctggcgg tccccccag cagcagcccc ccgtggccca gcaaccgcag | 2340 |
| gcacagggc cgccggcaca gggcagcgag gcccagctca tttcattcga ctgacccagg | 2400 |
| ccatgctcac gtccggagta acactacata cagttcacct gaaacgcctc gtctctaact | 2460 |
| gccgtcgtcc tgcctccctg tcctctactg ccggtagtgt cccttctctg cgagtgaggg | 2520 |
| ggggccttca ccccaagccc acctcccttg tcctcagcct actgcagtcc ctgagttagt | 2580 |
| ctctgctttc tttcccagg gctgggccat ggggagggaa ggactttctc ccaggggaag | 2640 |
| cccccagccc tgtgggtcat ggtctgtgag aggtggcagg aatggggacc ctcaccccc | 2700 |

```
aagcagcctg tgccctctgg ccgcactgtg agctggctgt ggtgtctggg tgtggcctgg   2760
ggctccctct gcagggcct  ctctcggcag ccacagccaa gggtggaggc ttcaggtctc   2820
cagcttctct gcttctcagc tgccatctcc agtgccccag aatggtacag cgataataaa   2880
atgtatttca gaaagg                                                    2896
```

<210> SEQ ID NO 10
<211> LENGTH: 776
<212> TYPE: PRT
<213> ORGANISM: Homo sapiens

<400> SEQUENCE: 10

```
Met Gly Arg Gly Ser Gly Thr Phe Glu Arg Leu Leu Asp Lys Ala Thr
  1               5                  10                  15

Ser Gln Leu Leu Leu Glu Thr Asp Trp Glu Ser Ile Leu Gln Ile Cys
                 20                  25                  30

Asp Leu Ile Arg Gln Gly Asp Thr Gln Ala Lys Tyr Ala Val Asn Ser
             35                  40                  45

Ile Lys Lys Lys Val Asn Asp Lys Asn Pro His Val Ala Leu Tyr Ala
         50                  55                  60

Leu Glu Val Met Glu Ser Val Val Lys Asn Cys Gly Gln Thr Val His
     65                  70                  75                  80

Asp Glu Val Ala Asn Lys Gln Thr Met Glu Glu Leu Lys Asp Leu Leu
                 85                  90                  95

Lys Arg Gln Val Glu Val Asn Val Arg Asn Lys Ile Leu Tyr Leu Ile
            100                 105                 110

Gln Ala Trp Ala His Ala Phe Arg Asn Glu Pro Lys Tyr Lys Val Val
        115                 120                 125

Gln Asp Thr Tyr Gln Ile Met Lys Val Glu Gly His Val Phe Pro Glu
    130                 135                 140

Phe Lys Glu Ser Asp Ala Met Phe Ala Ala Glu Arg Ala Pro Asp Trp
145                 150                 155                 160

Val Asp Ala Glu Glu Cys His Arg Cys Arg Val Gln Phe Gly Val Met
                165                 170                 175

Thr Arg Lys His His Cys Arg Ala Cys Gly Gln Ile Phe Cys Gly Lys
            180                 185                 190

Cys Ser Ser Lys Tyr Ser Thr Ile Pro Lys Phe Gly Ile Glu Lys Glu
        195                 200                 205

Val Arg Val Cys Glu Pro Cys Tyr Glu Gln Leu Asn Arg Lys Ala Glu
    210                 215                 220

Gly Lys Ala Thr Ser Thr Thr Glu Leu Pro Pro Glu Tyr Leu Thr Ser
225                 230                 235                 240

Pro Leu Ser Gln Gln Ser Gln Leu Pro Pro Lys Arg Asp Glu Thr Ala
                245                 250                 255

Leu Gln Glu Glu Glu Glu Leu Gln Leu Ala Leu Ala Leu Ser Gln Ser
            260                 265                 270

Glu Ala Glu Glu Lys Glu Arg Leu Arg Gln Lys Ser Thr Tyr Thr Ser
        275                 280                 285

Tyr Pro Lys Ala Glu Pro Met Pro Ser Ala Ser Ser Ala Pro Pro Ala
    290                 295                 300

Ser Ser Leu Tyr Ser Ser Pro Val Asn Ser Ser Ala Pro Leu Ala Glu
305                 310                 315                 320

Asp Ile Asp Pro Glu Leu Ala Arg Tyr Leu Asn Arg Asn Tyr Glu Lys
                325                 330                 335
```

-continued

```
Lys Gln Glu Glu Ala Arg Lys Ser Pro Thr Pro Ser Ala Pro Val Pro
            340                 345                 350
Leu Thr Glu Pro Ala Ala Gln Pro Gly Glu Gly His Ala Ala Pro Thr
            355                 360                 365
Asn Val Val Glu Asn Pro Leu Pro Glu Thr Asp Ser Gln Pro Ile Pro
            370                 375                 380
Pro Ser Gly Gly Pro Phe Ser Glu Pro Gln Phe His Asn Gly Glu Ser
385                 390                 395                 400
Glu Glu Ser His Glu Gln Phe Leu Lys Ala Leu Gln Asn Ala Val Thr
                405                 410                 415
Thr Phe Val Asn Arg Met Lys Ser Asn His Met Arg Gly Arg Ser Ile
            420                 425                 430
Thr Asn Asp Ser Ala Val Leu Ser Leu Phe Gln Ser Ile Asn Gly Met
            435                 440                 445
His Pro Gln Leu Leu Glu Leu Leu Asn Gln Leu Asp Glu Arg Arg Leu
            450                 455                 460
Tyr Tyr Glu Gly Leu Gln Asp Lys Leu Ala Gln Ile Arg Asp Ala Arg
465                 470                 475                 480
Gly Ala Leu Ser Ala Leu Arg Glu Glu His Arg Glu Lys Leu Arg Arg
                485                 490                 495
Ala Ala Glu Glu Ala Glu Arg Gln Arg Gln Ile Gln Leu Ala Gln Lys
            500                 505                 510
Leu Glu Ile Met Arg Gln Lys Lys Gln Glu Tyr Leu Glu Val Gln Arg
            515                 520                 525
Gln Leu Ala Ile Gln Arg Leu Gln Glu Gln Glu Lys Glu Arg Gln Met
            530                 535                 540
Arg Leu Glu Gln Gln Lys Gln Thr Val Gln Met Arg Ala Gln Met Pro
545                 550                 555                 560
Ala Phe Pro Leu Pro Tyr Ala Gln Leu Gln Ala Met Pro Ala Ala Gly
                565                 570                 575
Gly Val Leu Tyr Gln Pro Ser Gly Pro Ala Ser Phe Pro Ser Thr Phe
            580                 585                 590
Ser Pro Ala Gly Ser Val Glu Gly Ser Pro Met His Gly Val Tyr Met
            595                 600                 605
Ser Gln Pro Ala Pro Ala Ala Gly Pro Tyr Pro Ser Met Pro Ser Thr
            610                 615                 620
Ala Ala Asp Pro Ser Met Val Ser Ala Tyr Met Tyr Pro Ala Gly Ala
625                 630                 635                 640
Thr Gly Ala Gln Ala Ala Pro Gln Ala Gln Ala Gly Pro Thr Ala Ser
                645                 650                 655
Pro Ala Tyr Ser Ser Tyr Gln Pro Thr Pro Thr Ala Gly Tyr Gln Asn
            660                 665                 670
Val Ala Ser Gln Ala Pro Gln Ser Leu Pro Ala Ile Ser Gln Pro Pro
            675                 680                 685
Gln Ser Ser Thr Met Gly Tyr Met Gly Ser Gln Ser Val Ser Met Gly
            690                 695                 700
Tyr Gln Pro Tyr Asn Met Gln Asn Leu Met Thr Thr Leu Pro Ser Gln
705                 710                 715                 720
Asp Ala Ser Leu Pro Pro Gln Pro Tyr Ile Ala Gly Gln Gln Pro
                725                 730                 735
Met Tyr Gln Gln Met Ala Pro Ser Gly Gly Pro Pro Gln Gln Pro
            740                 745                 750
```

Pro Val Ala Gln Gln Pro Gln Ala Gln Gly Pro Pro Ala Gln Gly Ser
    755                 760                 765

Glu Ala Gln Leu Ile Ser Phe Asp
    770                 775

<210> SEQ ID NO 11
<211> LENGTH: 2980
<212> TYPE: DNA
<213> ORGANISM: Homo sapiens

<400> SEQUENCE: 11

| | | | | | | |
|---|---|---|---|---|---|---|
| gtccaacttg | gccggaagct | gcggagaggc | tcagccaccg | gaagtcagtg | gagggttcgg | 60 |
| ccggacgctc | tagaatcccg | gaggaccggg | atctctgtgg | ttggccgtga | cgggcaccct | 120 |
| ctaccgggga | tgacacattc | ccagagctcc | tgggaccaag | caaatggcgg | acacaattcc | 180 |
| ctgggcggaa | ggggacttcg | ggagccagta | gccaagacac | catggccgag | cctctgaagg | 240 |
| aggaagacgg | cgaggacggc | tctgcggagc | cccccgggcc | cgtgaaggtc | gaacccgccc | 300 |
| acaccgctgc | ctctgtagcg | gccaagaacc | tggccctgct | taaagcccgc | tccttcgatg | 360 |
| tgacctttga | cgtgggcgac | gagtacgaga | tcatcgagac | cataggcaac | ggggcctatg | 420 |
| gagtggtgtc | ctccgcccgc | cgccgcctca | ccggccagca | ggtggccatc | aagaagatcc | 480 |
| ctaatgcttt | cgatgtggtg | accaatgcca | agcggaccct | cagggagctg | aagatcctca | 540 |
| agcactttaa | acacgacaac | atcatcgcca | tcaaggacat | cctgaggccc | accgtgccct | 600 |
| atggcgaatt | caaatctgtc | tacgtggtcc | tggacctgat | ggaaagcgac | ctgcaccaga | 660 |
| tcatccactc | ctcacagccc | ctcacactgg | aacacgtgcg | ctacttcctg | taccaactgc | 720 |
| tgcggggcct | gaagtacatg | cactcggctc | aggtcatcca | ccgtgacctg | aagccctcca | 780 |
| acctattggt | gaatgagaac | tgtgagctca | agattggtga | ctttggtatg | gctcgtggcc | 840 |
| tgtgcacctc | gcccgctgaa | catcagtact | tcatgactga | gtatgtggcc | acgcgctggt | 900 |
| accgtgcgcc | cgagctcatg | ctctctttgc | atgagtatac | acaggctatt | gacctctggt | 960 |
| ctgtgggctg | catctttggt | gagatgctgg | cccggcgcca | gctcttccca | ggcaaaaact | 1020 |
| atgtacacca | gctacagctc | atcatgatgg | tgctgggtac | cccatcacca | gccgtgattc | 1080 |
| aggctgtggg | ggctgagagg | gtgcgggcct | atatccagag | cttgccacca | cgccagcctg | 1140 |
| tgccctggga | gacagtgtac | ccaggtgccg | accgccaggc | cctatactg | ctgggtcgca | 1200 |
| tgctgcgttt | tgagcccagc | gctcgcatct | cagcagctgc | tgcccttcgc | caccctttcc | 1260 |
| tggccaagta | ccatgatcct | gatgatgagc | ctgactgtgc | ccgcccttt | gactttgcct | 1320 |
| ttgaccgcga | agccctcact | cgggagcgca | ttaaggaggc | cattgtggct | gaaattgagg | 1380 |
| acttccatgc | aaggcgtgag | ggcatccgcc | aacagatccg | cttccagcct | tctctacagc | 1440 |
| ctgtggctag | tgagcctggc | tgtccagatg | ttgaaatgcc | cagtccctgg | gctcccagtg | 1500 |
| gggactgtgc | catggagtct | ccaccaccag | ccccgccacc | atgccccggc | cctgcacctg | 1560 |
| acaccattga | tctgacccctg | cagccacctc | caccagtcag | tgagcctgcc | ccaccaaaga | 1620 |
| aagatggtgc | catctcagac | aatactaagg | ctgcccttaa | agctgccctg | ctcaagtctt | 1680 |
| tgaggagccg | gctcagagat | ggccccagcg | caccctgga | ggctcctgag | cctcggaagc | 1740 |
| cggtgacagc | ccaggagcgc | cagcgggagc | gggaggagaa | gcggcggagg | cggcaagaac | 1800 |
| gagccaagga | gcgggagaaa | cggcggcagg | agcgggagcg | aaaggaacgg | ggggctgggg | 1860 |
| cctctggggg | ccctccact | gaccccttgg | ctggactagt | gctcagtgac | aatgacagaa | 1920 |
| gcctgttgga | acgctggact | cgaatggccc | ggcccgcagc | cccagccctc | acctctgtgc | 1980 |

-continued

```
cggcccctgc cccagcgcca acgccaaccc caaccccagt ccaacctacc agtcctcctc    2040 ctggcccctgt agcccagccc actggcccgc aaccacaatc tgcgggctct acctctggcc    2100
ctgtacccca gcctgcctgc ccacccctg gccctgcacc ccaccccact ggccctcctg     2160
ggcccatccc tgtccccgcg ccaccccaga ttgccacctc caccagcctc ctggctgccc    2220
agtcacttgt gccacccct gggctgcctg gctccagcac cccaggagtt ttgccttact    2280
tcccacctgg cctgccgccc ccagacgccg ggggagcccc tcagtcttcc atgtcagagt    2340
cacctgatgt caaccttgtg acccagcagc tatctaagtc acaggtggag acccccctgc    2400
cccctgtgtt ctcaggcaca ccaaagggca gtggggctgg ctacggtgtt ggctttgacc    2460
tggaggaatt cttaaaccag tctttcgaca tgggcgtggc tgatgggcca caggatggcc    2520
aggcagattc agcctctctc tcagcctccc tgcttgctga ctggctcgaa ggccatggca    2580
tgaaccctgc cgatattgag tccctgcagc gtgagatcca gatggactcc ccaatgctgc    2640
tggctgacct gcctgacctc caggaccct gaggccccca gcctgtgcct tgctgccaca    2700
gtagacctag ttccaggatc catgggagca ttctcaaagg ctttagccct ggacccagca    2760
ggtgaggctc ggcttggatt attctgcagg ttcatctcag acccacccttt cagccttaag    2820 cagccacctg agccaccacc gagccatggc aggatcggga gaccccaact cccctgaac    2880 aatccttttc agtattatat ttttattatt attatgttat tattacactg tcttttgcc     2940 atcaaaatga ggcctgtgaa atacaaggtt cccttctgca                          2980
```

<210> SEQ ID NO 12
<211> LENGTH: 816
<212> TYPE: PRT
<213> ORGANISM: Homo sapiens

<400> SEQUENCE: 12

```
Met Ala Glu Pro Leu Lys Glu Glu Asp Gly Glu Asp Gly Ser Ala Glu
 1               5                  10                  15

Pro Pro Gly Pro Val Lys Val Pro Ala His Thr Ala Ala Ser Val
            20                  25                  30

Ala Ala Lys Asn Leu Ala Leu Leu Lys Ala Arg Ser Phe Asp Val Thr
        35                  40                  45

Phe Asp Val Gly Asp Glu Tyr Glu Ile Ile Glu Thr Ile Gly Asn Gly
    50                  55                  60

Ala Tyr Gly Val Val Ser Ser Ala Arg Arg Arg Leu Thr Gly Gln Gln
65                  70                  75                  80

Val Ala Ile Lys Lys Ile Pro Asn Ala Phe Asp Val Val Thr Asn Ala
                85                  90                  95

Lys Arg Thr Leu Arg Glu Leu Lys Ile Leu Lys His Phe Lys His Asp
            100                 105                 110

Asn Ile Ile Ala Ile Lys Asp Ile Leu Arg Pro Thr Val Pro Tyr Gly
        115                 120                 125

Glu Phe Lys Ser Val Tyr Val Val Leu Asp Leu Met Glu Ser Asp Leu
    130                 135                 140

His Gln Ile Ile His Ser Ser Gln Pro Leu Thr Leu Glu His Val Arg
145                 150                 155                 160

Tyr Phe Leu Tyr Gln Leu Leu Arg Gly Leu Lys Tyr Met His Ser Ala
                165                 170                 175

Gln Val Ile His Arg Asp Leu Lys Pro Ser Asn Leu Leu Val Asn Glu
            180                 185                 190
```

```
Asn Cys Glu Leu Lys Ile Gly Asp Phe Gly Met Ala Arg Gly Leu Cys
            195                 200                 205

Thr Ser Pro Ala Glu His Gln Tyr Phe Met Thr Glu Tyr Val Ala Thr
        210                 215                 220

Arg Trp Tyr Arg Ala Pro Glu Leu Met Leu Ser Leu His Glu Tyr Thr
225                 230                 235                 240

Gln Ala Ile Asp Leu Trp Ser Val Gly Cys Ile Phe Gly Glu Met Leu
                245                 250                 255

Ala Arg Arg Gln Leu Phe Pro Gly Lys Asn Tyr Val His Gln Leu Gln
            260                 265                 270

Leu Ile Met Met Val Leu Gly Thr Pro Ser Pro Ala Val Ile Gln Ala
        275                 280                 285

Val Gly Ala Glu Arg Val Arg Ala Tyr Ile Gln Ser Leu Pro Pro Arg
290                 295                 300

Gln Pro Val Pro Trp Glu Thr Val Tyr Pro Gly Ala Asp Arg Gln Ala
305                 310                 315                 320

Leu Ser Leu Leu Gly Arg Met Leu Arg Phe Glu Pro Ser Ala Arg Ile
                325                 330                 335

Ser Ala Ala Ala Leu Arg His Pro Phe Leu Ala Lys Tyr His Asp
            340                 345                 350

Pro Asp Asp Glu Pro Asp Cys Ala Pro Pro Phe Asp Phe Ala Phe Asp
            355                 360                 365

Arg Glu Ala Leu Thr Arg Glu Arg Ile Lys Glu Ala Ile Val Ala Glu
        370                 375                 380

Ile Glu Asp Phe His Ala Arg Arg Glu Gly Ile Arg Gln Gln Ile Arg
385                 390                 395                 400

Phe Gln Pro Ser Leu Gln Pro Val Ala Ser Glu Pro Gly Cys Pro Asp
                405                 410                 415

Val Glu Met Pro Ser Pro Trp Ala Pro Ser Gly Asp Cys Ala Met Glu
            420                 425                 430

Ser Pro Pro Pro Ala Pro Pro Cys Pro Gly Pro Ala Pro Asp Thr
            435                 440                 445

Ile Asp Leu Thr Leu Gln Pro Pro Pro Val Ser Glu Pro Ala Pro
450                 455                 460

Pro Lys Lys Asp Gly Ala Ile Ser Asp Asn Thr Lys Ala Ala Leu Lys
465                 470                 475                 480

Ala Ala Leu Leu Lys Ser Leu Arg Ser Arg Leu Arg Asp Gly Pro Ser
                485                 490                 495

Ala Pro Leu Glu Ala Pro Glu Pro Arg Lys Pro Val Thr Ala Gln Glu
            500                 505                 510

Arg Gln Arg Glu Arg Glu Glu Lys Arg Arg Arg Gln Glu Arg Ala
        515                 520                 525

Lys Glu Arg Glu Lys Arg Arg Gln Glu Arg Glu Arg Lys Glu Arg Gly
530                 535                 540

Ala Gly Ala Ser Gly Gly Pro Ser Thr Asp Pro Leu Ala Gly Leu Val
545                 550                 555                 560

Leu Ser Asp Asn Asp Arg Ser Leu Leu Glu Arg Trp Thr Arg Met Ala
                565                 570                 575

Arg Pro Ala Ala Pro Ala Leu Thr Ser Val Pro Ala Pro Ala Pro Ala
            580                 585                 590

Pro Thr Pro Thr Pro Thr Pro Val Gln Pro Thr Ser Pro Pro Gly
        595                 600                 605

Pro Val Ala Gln Pro Thr Gly Pro Gln Pro Gln Ser Ala Gly Ser Thr
```

```
                 610                 615                 620
Ser Gly Pro Val Pro Gln Pro Ala Cys Pro Pro Gly Pro Ala Pro
625                 630                 635                 640

His Pro Thr Gly Pro Pro Gly Pro Ile Pro Val Pro Ala Pro Gln
                645                 650                 655

Ile Ala Thr Ser Thr Ser Leu Leu Ala Ala Gln Ser Leu Val Pro Pro
                660                 665                 670

Pro Gly Leu Pro Gly Ser Ser Thr Pro Gly Val Leu Pro Tyr Phe Pro
                675                 680                 685

Pro Gly Leu Pro Pro Pro Asp Ala Gly Gly Ala Pro Gln Ser Ser Met
        690                 695                 700

Ser Glu Ser Pro Asp Val Asn Leu Val Thr Gln Gln Leu Ser Lys Ser
705                 710                 715                 720

Gln Val Glu Asp Pro Leu Pro Pro Val Phe Ser Gly Thr Pro Lys Gly
                725                 730                 735

Ser Gly Ala Gly Tyr Gly Val Gly Phe Asp Leu Glu Glu Phe Leu Asn
                740                 745                 750

Gln Ser Phe Asp Met Gly Val Ala Asp Gly Pro Gln Asp Gly Gln Ala
        755                 760                 765

Asp Ser Ala Ser Leu Ser Ala Ser Leu Leu Ala Asp Trp Leu Glu Gly
770                 775                 780

His Gly Met Asn Pro Ala Asp Ile Glu Ser Leu Gln Arg Glu Ile Gln
785                 790                 795                 800

Met Asp Ser Pro Met Leu Leu Ala Asp Leu Pro Asp Leu Gln Asp Pro
                805                 810                 815

<210> SEQ ID NO 13
<211> LENGTH: 1476
<212> TYPE: DNA
<213> ORGANISM: Homo sapiens

<400> SEQUENCE: 13
atggagaact tccaaaaggt ggaaaagatc ggagagggca cgtacggagt tgtgtacaaa      60
gccagaaaca agttgacggg agaggtggtg gcgcttaaga aaatccgcct ggacactgag     120
actgagggtg tgcccagtac tgccatccga gagatctctc tgcttaagga gcttaaccat     180
cctaatattg tcaagctgct ggatgtcatt cacacagaaa ataaactcta cctggttttt     240
gaatttctgc accaagatct caagaaattc atggatgcct tgctctcac tggcattcct     300 cttcccctca tcaagagcta tctgttccag ctgctccagg cctagctttt ctgccattct     360
catcgggtcc tccaccgaga ccttaaacct cagaatctgc ttattaacac agaggggcc     420 atcaagctag cagactttgg actagccaga gcttttggag tccctgttcg tacttacacc     480
catgaggtgg tgaccctgtg gtaccgagct cctgaaatcc tcctgggctc gaaatattat     540
tccacagctg tggacatctg gagcctgggc tgcatctttg ctgagatggt gactcgccgg     600
gccctgttcc ctgagattc tgagattgac cagctcttcc ggatctttcg gactctgggg     660
accccagatg aggtggtgtg gccaggagtt acttctatgc ctgattacaa gccaagtttc     720
cccaagtggg cccggcaaga ttttagtaaa gttgtacctc cctggatga agatggacgg     780 agcttgttat cgcaaatgct gcactacgac cctaacaagc ggatttcggc caaggcagcc     840
ctggctcacc ctttcttcca ggatgtgacc aagccagtac ccatcttcg actctgatag     900 ccttcttgaa gccccgacc ctaatcggct caccctctcc tccagtgtgg gcttgaccag     960
cttggccttg ggctatttgg actcaggtgg gccctctgaa cttgccttaa acactcacct    1020
```

```
tctagtctta accagccaac tctgggaata caggggtgaa aggggggaac cagtgaaaat   1080
gaaaggaagt ttcagtatta gatgcactta agttagcctc caccaccctt tcccccttct   1140
cttagttatt gctgaagagg gttggtataa aaataatttt aaaaaagcct tcctacacgt   1200
tagatttgcc gtaccaatct ctgaatgccc cataattatt atttccagtg tttgggatga   1260
ccaggatccc aagcctcctg ctgccacaat gtttataaag gccaaatgat agcgggggct   1320
aagttggtgc ttttgagaat taagtaaaac aaaaccactg ggaggagtct atttaaaga    1380 attcggttaa aaaatagatc caatcagttt atacccctagt tagtgttttc ctcacctaat  1440
aggctgggag actgaagact cagcccgggt gggggt                             1476
```

<210> SEQ ID NO 14
<211> LENGTH: 298
<212> TYPE: PRT
<213> ORGANISM: Homo sapiens

<400> SEQUENCE: 14

```
Met Glu Asn Phe Gln Lys Val Glu Lys Ile Gly Glu Gly Thr Tyr Gly
 1               5                  10                  15

Val Val Tyr Lys Ala Arg Asn Lys Leu Thr Gly Glu Val Val Ala Leu
            20                  25                  30

Lys Lys Ile Arg Leu Asp Thr Glu Thr Glu Gly Val Pro Ser Thr Ala
        35                  40                  45

Ile Arg Glu Ile Ser Leu Leu Lys Glu Leu Asn His Pro Asn Ile Val
    50                  55                  60

Lys Leu Leu Asp Val Ile His Thr Glu Asn Lys Leu Tyr Leu Val Phe
65                  70                  75                  80

Glu Phe Leu His Gln Asp Leu Lys Lys Phe Met Asp Ala Ser Ala Leu
                85                  90                  95

Thr Gly Ile Pro Leu Pro Leu Ile Lys Ser Tyr Leu Phe Gln Leu Leu
            100                 105                 110

Gln Gly Leu Ala Phe Cys His Ser His Arg Val Leu His Arg Asp Leu
        115                 120                 125

Lys Pro Gln Asn Leu Leu Ile Asn Thr Glu Gly Ala Ile Lys Leu Ala
    130                 135                 140

Asp Phe Gly Leu Ala Arg Ala Phe Gly Val Pro Val Arg Thr Tyr Thr
145                 150                 155                 160

His Glu Val Val Thr Leu Trp Tyr Arg Ala Pro Glu Ile Leu Leu Gly
                165                 170                 175

Ser Lys Tyr Tyr Ser Thr Ala Val Asp Ile Trp Ser Leu Gly Cys Ile
            180                 185                 190

Phe Ala Glu Met Val Thr Arg Arg Ala Leu Phe Pro Gly Asp Ser Glu
        195                 200                 205

Ile Asp Gln Leu Phe Arg Ile Phe Arg Thr Leu Gly Thr Pro Asp Glu
    210                 215                 220

Val Val Trp Pro Gly Val Thr Ser Met Pro Asp Tyr Lys Pro Ser Phe
225                 230                 235                 240

Pro Lys Trp Ala Arg Gln Asp Phe Ser Lys Val Val Pro Pro Leu Asp
                245                 250                 255

Glu Asp Gly Arg Ser Leu Leu Ser Gln Met Leu His Tyr Asp Pro Asn
            260                 265                 270

Lys Arg Ile Ser Ala Lys Ala Ala Leu Ala His Pro Phe Phe Gln Asp
        275                 280                 285
```

Val Thr Lys Pro Val Pro His Leu Arg Leu
    290                 295

<210> SEQ ID NO 15
<211> LENGTH: 3505
<212> TYPE: DNA
<213> ORGANISM: Homo sapiens

<400> SEQUENCE: 15

| | | | | | |
|---|---|---|---|---|---|
| cgccgcctgc | ccgcccgccc | gctcgccccc | ggtccggact | cctcctcctc | ctcttctcgc | 60 |
| attgcagttg | aacccagcag | cccgccccac | cggtggcttt | tgggggcaga | ccccggcggc | 120 |
| tgtggcagga | gggcggcggc | ggcggctgcg | gtcgaagaag | gggacgccga | caagagttga | 180 |
| agtattgata | caccaagga | actctatcac | aatttgaaaa | gataagcaaa | agtttgattt | 240 |
| ccagacacta | cagaagaagt | aaaaatgcgt | ccaatgcgaa | tttttgtgaa | tgatgaccgc | 300 |
| catgtgatgg | caaagcattc | ttccgtttat | ccaacacaag | aggagctgga | ggcagtccag | 360 |
| aacatggtgt | cccacacgga | gcgggcgctc | aaagctgtgt | ccgactggat | acacgagcag | 420 |
| gaaaagggta | gcagcgagca | ggcagagtcc | gataacatgg | atgtgccccc | agaggacgac | 480 |
| agtaaagaag | gggctgggga | acagaagacg | gagcacatga | ccagaacctg | tcggggagtg | 540 |
| atgcgggctg | ggcctggtgg | ccaaagtgcc | tcctactcaa | gggggacttg | gatctggagc | 600 |
| tggtgctgct | gtgtaaggag | aagcccacaa | ccggccctcc | tggacaaggt | ggccgacaac | 660 |
| ctggccatcc | agcttgctgc | tgtaacagaa | gacaagtacg | aaatactgca | atctgtcgac | 720 |
| gatgctgcga | ttgtgataaa | aaacacaaaa | gagcctccat | tgtccctgac | catccacctg | 780 |
| acatcccctg | ttgtcagaga | agaaatggag | aaagtattag | ctggagaaac | gctatcagtc | 840 |
| aacgaccccc | cggacgttct | ggacaggcag | aaatgctttg | ctgccttggc | gtccctccga | 900 |
| cacgccaagt | ggttccaggc | cagagccaac | gggctgaagt | cttgtgtcat | tgtgatccgg | 960 |
| gtcttgaggg | acctgtgcac | tcgcgtgccc | acctgggtc | ccctccgagg | ctggcctctc | 1020 |
| gagctcctgt | gtgagaaatc | cattggcacg | gccaacagac | cgatgggtgc | tggcgaggcc | 1080 |
| ctgcggagag | tgctggagtg | cctggcgtcg | ggcatcgtga | tgccagatgg | ttctggcatt | 1140 |
| tatgacccctt | gtgaaaaaga | agccactgat | gctattgggc | atctagacag | acagcaacgg | 1200 |
| gaagatatca | cacagagtgc | gcagcacgca | ctgcggctcg | ccgcgttcgg | ccagctccat | 1260 |
| aaagtcctag | gcatggaccc | tctgccttcc | aagatgccca | agaaaccaaa | gaatgaaaac | 1320 |
| ccagtggact | acaccgttca | gatcccacca | agcaccacct | atgccattac | gcccatgaaa | 1380 |
| cgcccaatgg | aggaggacgg | ggaggagaag | tcgcccagca | aaaagaagaa | gaagattcag | 1440 |
| aagaaagagg | agaaggcaga | gccccccag | gctatgaatg | ccctgatgcg | gttgaaccag | 1500 |
| ctgaagccag | ggctgcagta | caagctggtg | tcccagactg | ggcccgtcca | tgccccatc | 1560 |
| tttaccatgt | ctgtggaggt | tgatggcaat | tcattcgagg | cctctgggcc | ctccaaaaag | 1620 |
| acggccaagc | tgcacgtggc | cgttaaggtg | ttacaggaca | tgggcttgcc | gacgggtgct | 1680 |
| gaaggcaggg | actcgagcaa | gggggaggac | tcggctgagg | agaccgaggc | gaagccagca | 1740 |
| gtggtggccc | ctgccccagt | ggtagaagct | gtctccaccc | ctagtgcggc | ctttccctca | 1800 |
| gatgccactg | ccgagaacgt | aaaacagcag | ggccgatcc | tgacaaagca | cggcaagaac | 1860 |
| ccagtcatgg | agctgaacga | agaggcgt | gggctcaagt | acgagctcat | ctccgagacc | 1920 |
| gggggcagcc | acgacaagcg | cttcgtcatg | gaggtcgaag | tggatggaca | aagttccaa | 1980 |
| ggtgctggtt | ccaacaaaaa | ggtggcgaag | gcctacgctg | ctcttgctgc | cctagaaaag | 2040 |

-continued

```
cttttccctg acaccctct ctcgcccttg atgccaacaa aaagaagaga gccccagtac    2100
ccgtcagagg gggaccgaaa tttgctgcta agccacataa ccctggcttc ggcatgggag    2160
gccccatgca caacgaagtg cccccacccc ccaaccttcg agggcgggga agaggcggga    2220
cgatccgggg acgagggcgc gggcgaggat ttggtggcgc caaccatgga ggctacatga    2280
atgccggtgc tgggtatgga agctatgggt acggaggcaa ctctgcgaca gcaggctaca    2340
gtcagttcta cagcaacgga gggcattctg ggaatgccag tggcggtggc ggcggggggcg    2400 gtggtggctc ctccggctat ggctcctact accaaggtga caactacaac tcaccggtgc    2460
ccccaaaaca cgctgggaag aagcagccgc acggggggcca gcagaagccc tcctacggct    2520
cgggctacca gtcccaccag ggccagcagc agtcctacaa ccagagcccc tacagcaact    2580
atggccctcc acagggcaag cagaaaggct ataaccatgg acaaggcagc tactcctact    2640
cgaactccta caactctccc gggggcgggc gcggatccga ctacaactac gagagcaaat    2700
tcaactacag tggtagtgga ggccgaagcg gcgggaacag ctacggctca ggcggggcat    2760
cctacaaccc aggtcacac gggggctacg gcggaggttc tgggggcggc tcctcatacc    2820
aaggcaaaca aggaggctgc tcacagtcga actacagctc ccggggtccg gccagaacta    2880
cagtggccct cccagctcct accagtcctc acaaggcggc tatggcagaa acgcagacca    2940
cagcatgaac taccagtaca gataagcccc gcgcggagat ttctaccttc tgcacttact    3000
ccccatcaga agatcgagtt ttatgcatca cagttaacat gtcagctgcc tgcgctccag    3060 gccccccgccc ccatcccgtc cacgttgctg tgtcgtgagg tgcagcgggt caccctgtgg    3120
cccgtcctgt gacccatatt tagccgtgtt tgggactccg tgtcttcaat ggtttgttag    3180
ttgccattac aactttgtct gggtagagtt tttgagtttt tgcagttcag tatccctctg    3240
tctattcaca cttcgtgtta gtggtaactc agtttgtctt taaatagtta cagaagggat    3300
acgtcatttg ttaatgcttt ttgttgaagt gagttaaacg agcttttctg tattttaatg    3360
ctttagtgtt tcagttttat aagtgaagat tttatttaa aaaccagtgg gaaagagtgg    3420
gggggttctt tttatgtctg ggtcattcag gcagtacatc tgaattaagc tgaatgtaga    3480
caaataaaga aaacaaaac tgaaa                                            3505
```

<210> SEQ ID NO 16
<211> LENGTH: 671
<212> TYPE: PRT
<213> ORGANISM: Homo sapiens

<400> SEQUENCE: 16

```
Met Arg Pro Met Arg Ile Phe Val Asn Asp Asp Arg His Val Met Ala
 1               5                  10                  15

Lys His Ser Ser Val Tyr Pro Thr Gln Glu Glu Leu Glu Ala Val Gln
                20                  25                  30

Asn Met Val Ser His Thr Glu Arg Ala Leu Lys Ala Val Ser Asp Trp
            35                  40                  45

Ile His Glu Gln Glu Lys Gly Ser Ser Glu Gln Ala Glu Ser Asp Asn
        50                  55                  60

Met Asp Val Pro Pro Glu Asp Asp Ser Lys Glu Gly Ala Gly Glu Gln
 65                  70                  75                  80

Lys Thr Glu His Met Thr Arg Thr Cys Arg Gly Val Met Arg Ala Gly
                85                  90                  95

Pro Gly Gly Gln Ser Ala Ser Tyr Ser Arg Gly Thr Trp Ile Trp Ser
               100                 105                 110
```

-continued

```
Trp Cys Cys Cys Val Arg Arg Ser Pro Gln Pro Ala Leu Leu Asp Lys
            115                 120                 125

Val Ala Asp Asn Leu Ala Ile Gln Leu Ala Ala Val Thr Glu Asp Lys
130                 135                 140

Tyr Glu Ile Leu Gln Ser Val Asp Asp Ala Ala Ile Val Ile Lys Asn
145                 150                 155                 160

Thr Lys Glu Pro Pro Leu Ser Leu Thr Ile His Leu Thr Ser Pro Val
                165                 170                 175

Val Arg Glu Glu Met Glu Lys Val Leu Ala Gly Glu Thr Leu Ser Val
            180                 185                 190

Asn Asp Pro Pro Asp Val Leu Asp Arg Gln Lys Cys Phe Ala Ala Leu
            195                 200                 205

Ala Ser Leu Arg His Ala Lys Trp Phe Gln Ala Arg Ala Asn Gly Leu
210                 215                 220

Lys Ser Cys Val Ile Val Ile Arg Val Leu Arg Asp Leu Cys Thr Arg
225                 230                 235                 240

Val Pro Thr Trp Gly Pro Leu Arg Gly Trp Pro Leu Glu Leu Leu Cys
                245                 250                 255

Glu Lys Ser Ile Gly Thr Ala Asn Arg Pro Met Gly Ala Gly Glu Ala
            260                 265                 270

Leu Arg Arg Val Leu Glu Cys Leu Ala Ser Gly Ile Val Met Pro Asp
            275                 280                 285

Gly Ser Gly Ile Tyr Asp Pro Cys Glu Lys Glu Ala Thr Asp Ala Ile
290                 295                 300

Gly His Leu Asp Arg Gln Arg Glu Asp Ile Thr Gln Ser Ala Gln
305                 310                 315                 320

His Ala Leu Arg Leu Ala Ala Phe Gly Gln Leu His Lys Val Leu Gly
                325                 330                 335

Met Asp Pro Leu Pro Ser Lys Met Pro Lys Lys Pro Lys Asn Glu Asn
            340                 345                 350

Pro Val Asp Tyr Thr Val Gln Ile Pro Pro Ser Thr Thr Tyr Ala Ile
            355                 360                 365

Thr Pro Met Lys Arg Pro Met Glu Glu Asp Gly Glu Glu Lys Ser Pro
370                 375                 380

Ser Lys Lys Lys Lys Ile Gln Lys Lys Glu Glu Lys Ala Glu Pro
385                 390                 395                 400

Pro Gln Ala Met Asn Ala Leu Met Arg Leu Asn Gln Leu Lys Pro Gly
                405                 410                 415

Leu Gln Tyr Lys Leu Val Ser Gln Thr Gly Pro Val His Ala Pro Ile
            420                 425                 430

Phe Thr Met Ser Val Glu Val Asp Gly Asn Ser Phe Glu Ala Ser Gly
            435                 440                 445

Pro Ser Lys Lys Thr Ala Lys Leu His Val Ala Val Lys Val Leu Gln
450                 455                 460

Asp Met Gly Leu Pro Thr Gly Ala Glu Gly Arg Asp Ser Ser Lys Gly
465                 470                 475                 480

Glu Asp Ser Ala Glu Glu Thr Glu Ala Lys Pro Ala Val Val Ala Pro
                485                 490                 495

Ala Pro Val Val Glu Ala Val Ser Thr Pro Ser Ala Ala Phe Pro Ser
            500                 505                 510

Asp Ala Thr Ala Glu Asn Val Lys Gln Gln Gly Pro Ile Leu Thr Lys
            515                 520                 525

His Gly Lys Asn Pro Val Met Glu Leu Asn Glu Lys Arg Arg Gly Leu
```

|  |  | 530 |  |  | 535 |  |  | 540 |  |  |  |
|---|---|---|---|---|---|---|---|---|---|---|---|

Lys Tyr Glu Leu Ile Ser Glu Thr Gly Gly Ser His Asp Lys Arg Phe
545                 550                 555                 560

Val Met Glu Val Glu Val Asp Gly Gln Lys Phe Gln Gly Ala Gly Ser
                565                 570                 575

Asn Lys Lys Val Ala Lys Ala Tyr Ala Ala Leu Ala Ala Leu Glu Lys
                580                 585                 590

Leu Phe Pro Asp Thr Pro Leu Ser Pro Leu Met Pro Thr Lys Arg Arg
            595                 600                 605

Glu Pro Gln Tyr Pro Ser Glu Gly Asp Arg Asn Leu Leu Leu Ser His
        610                 615                 620

Ile Thr Leu Ala Ser Ala Trp Glu Ala Pro Cys Thr Thr Lys Cys Pro
625                 630                 635                 640

His Pro Pro Thr Phe Glu Gly Gly Glu Glu Ala Gly Arg Ser Gly Asp
                645                 650                 655

Glu Gly Ala Gly Glu Asp Leu Val Ala Pro Thr Met Glu Ala Thr
            660                 665                 670

<210> SEQ ID NO 17
<211> LENGTH: 4168
<212> TYPE: DNA
<213> ORGANISM: Homo sapiens

<400> SEQUENCE: 17

```
ttggggtgga gcagagaagt ttctgtattc agctgcccag gcagaggaga atgggtctc      60 cacagcctga agaatgaaga cacgacagaa taaagactcg atgtcaatga ggagtggacg     120
gaagaaagag gccctgggc cccgggaaga actgagatcg aggggccggg cctcccctgg     180 agggtcagc acgtccagca gtgatggcaa agctgagaag tccaggcaga cagccaagaa     240
ggcccgagta gaggaagcct ccaccccaaa ggtcaacaag cagggtcgga gtgaggagat    300
ctcagagagt gaaagtgagg agaccaatgc caccaaaaag accaaaactg aggaactccc    360
tcggccacag tctccctccg atctggatag cttggacggg cggagcctta atgatgatgg    420
cagcagcgac cctagggata tcgaccagga caaccgaagc acgtccccca gtatctacag    480 cccctggaagt gtggagaatg actctgactc atcttctggc ctgtcccagg gcccagcccg    540 ccccctaccac ccacctccac tctttcctcc ttcccctcaa ccgccagaca gcacccctcg    600
acagccagag gctagctttg aacccatcc ttctgtgaca cccactggat atcatgctcc      660
catggagccc ccacatctc gaatgttcca ggctcctcct ggggcccctc cccctcaccc      720
acagctctat cccgggggca ctggtggagt tttgtctgga cccccaatgg gtcccaaggg     780 gggagggct gcctcatcag tgggggccc taatgggggt aagcagcacc ccccacccac      840
tactcccatt tcagtatcaa gctctgggc tagtggtgct ccccaacaa agccgcctac      900 cactccagtg ggtggtggga acctaccttc tgctccacca ccagccaact tcccccatgt    960
gacaccgaac ctgcctcccc cacctgccct gagacccctc aacaatgcat cagcctctcc   1020
ccctggcctg gggcccaac cactacctgg tcatctgccc tctccccacg ccatgggaca    1080
gggtatcggt ggacttcctc ctggcccaga gaagggccca actctggctc cttcacccca    1140
ctctctgcct cctgcttcct cttctgctcc agcgccccc atgaggtttc cttattcatc     1200
ctctagtagt agctctgcag cagcctcctc ttccagttct tcctcctctt cctctgcctc    1260
ccccttccca gcttccagg cattgcccag ctaccccac tctttccctc ccccaacaag    1320
cctctctgtc tccaatcagc cccccaagta tactcagcct tctctcccat cccaggctgt    1380
```

```
gtggagccag ggtcccccac cacctcctcc ctatggccgc ctcttagcca acagcaatgc   1440
ccatccaggc cccttccctc cctctactgg ggcccagtcc accgccacc caccagtctc    1500 aacacatcac catcaccacc agcaacagca acagcagcag cagcagcagc agcagcagca   1560
gcatcacgga aactctgggc ccctcctcc tggagcattt ccccacccac tggagggcgg    1620
tagctcccac cacgcacacc cttacgccat gtctccctcc ctggggtctc tgaggcccta   1680
cccaccaggg ccagcacacc tgcccccacc tcacagccag gtgtcctaca gccaagcagg   1740
ccccaatggc cctccagtct cttcctcttc caactcttcc tcttccactt ctcaagggtc   1800
ctacccatgt tcacacccct ccccttccca gggccctcaa ggggcgccct accctttccc   1860
accggtgcct acgtcacca cctcttcggc tacccttttcc acggtcattg ccaccgtggc   1920
ttcctcgcca gcaggctaca aaacggcctc cccacctggg ccccaccgt acggaaagag    1980 agcccgtcc ccggggcct acaagacagc caccccaccc ggatacaaac ccgggtcgcc     2040
tccctccttc cgaacgggga ccccaccggg ctatcgagga acctcgccac ctgcaggccc   2100
agggaccttc aagccgggct cgcccaccgt gggacctggg ccctgccac ctgcggggcc    2160 ctcaggcctg ccatcgctgc caccaccacc tgcggcccct gcctcagggc cgcccctgag   2220
cgccacgcag atcaaacagg agccggctga ggagtatgag accccgaga gcccggtgcc    2280 cccagcccgc agcccctcgc cccctcccaa ggtggtagat gtacccagcc atgccagtca   2340
gtctgccagg ttcaacaaac acctggatcg cggcttcaac tcgtgcgcgc gcagcgacct   2400
gtacttcgtg ccactggagg gctccaagct ggccaagaag cgggccgacc tggtggagaa   2460
ggtgcggcgc gaggccgagc agcgcgcgcg cgaagaaaag gagcgcgagc gcgagcggga   2520
acgcgagaaa gagcgcgagc gcgagaagga gcgcgagctt gaacgcagcg tgaagttggc   2580
tcaggagggc cgtgctccgg tggaatgccc atctctgggc ccagtgcccc atcgccctcc   2640
atttgaaccg ggcagtgcgg tggctacagt gccccctac ctgggtcctg acactccagc    2700
cttgcgcact ctcagtgaat atgcccggcc tcatgtcatg tctcctggca atcgcaacca   2760
tccattctac gtgcccctgg gggcagtgga cccggggctc ctgggttaca atgtcccggc   2820
cctgtacagc agtgatccag ctgcccggga gagggaacgg gaagcccgtg aacgagacct   2880
ccgtgaccgc ctcaagcctg gctttgaggt gaagcctagt gagctggaac ccctacatgg   2940
ggtccctggg ccgggcttgg atccctttcc ccgacatggg ggcctggctc tgcagcctgg   3000
cccacctggc ctgcaccctt tccccttca tccgagcctg gggcccctgg agcgagaacg    3060
tctagcgctg gcagctgggc cagccctgcg gcctgacatg tcctatgctg agcggctggc   3120
agctgagagg cagcacgcag aaagggtggc ggccctgggc aatgacccac tggcccggct   3180
gcagatgctc aatgtgactc cccatcacca ccagcactcc cacatccact cgcacctgca   3240
cctgcaccag caagatgcta tccatgcagc ctctgcctcg gtgcaccctc tcattgaccc   3300
cctggcctca gggtctcacc ttacccggat cccctaccca gctggaactc tccctaaccc   3360
cctgcttcct caccctctgc acgagaacga agttcttcgt caccagctct ttgctgcccc   3420
ttaccgggac ctgccggcct cccttttctgc ccgatgtca gcagctcatc agctgcaggc   3480
catgcacgca cagtcagctg agctgcacgcg cttggcgctg aacagcagc agtggctgca   3540 tgcccatcac ccgctgcaca gtgtgccgct gcctgcccag gaggactact acagtcacct   3600
gaagaaggaa agcgacaagc cactgtagaa cctgcgatca agagagcacc atggctccta   3660
cattggacct tggagcaccc ccaccctccc ccaccgtgc ccttggcctg ccacccagag    3720
```

-continued

```
ccaagagggt gctgctcagt tgcagggcct ccgcagctgg acagagagtg ggggagggag    3780
ggacagacag aaggccaagg cccgatgtgg tgtgcagagg tggggaggtg gcgaggatgg    3840
ggacagaaag cgcacagaat cttggaccag gtctctcttc cttgtccccc ctgcttttct    3900
cctcccccat gcccaacccc tgtggccgcc gcccctcccc tgcccgttg gtgtgattat     3960 ttcatctgtt agatgtggct gttttgcgta gcatcgtgtg ccaccctgc ccctccccga     4020 tccctgtgtg cgcgccccct ctgcaatgta tgccccttgc ccttcccca cactaataat    4080 ttatatatat aaatatctat atgacgctct taaaaaaaca tcccaaccaa aaccaaccaa    4140
acaaaaacat cctcacaact ccccagga                                      4168
```

<210> SEQ ID NO 18
<211> LENGTH: 1184
<212> TYPE: PRT
<213> ORGANISM: Homo sapiens

<400> SEQUENCE: 18

```
Met Lys Thr Arg Gln Asn Lys Asp Ser Met Ser Met Arg Ser Gly Arg
 1               5                  10                  15

Lys Lys Glu Ala Pro Gly Pro Arg Glu Glu Leu Arg Ser Arg Gly Arg
            20                  25                  30

Ala Ser Pro Gly Gly Val Ser Thr Ser Ser Ser Asp Gly Lys Ala Glu
        35                  40                  45

Lys Ser Arg Gln Thr Ala Lys Lys Ala Arg Val Glu Glu Ala Ser Thr
    50                  55                  60

Pro Lys Val Asn Lys Gln Gly Arg Ser Glu Glu Ile Ser Glu Ser Glu
65                  70                  75                  80

Ser Glu Glu Thr Asn Ala Pro Lys Lys Thr Lys Thr Glu Glu Leu Pro
                85                  90                  95

Arg Pro Gln Ser Pro Ser Asp Leu Asp Ser Leu Asp Gly Arg Ser Leu
            100                 105                 110

Asn Asp Asp Gly Ser Ser Asp Pro Arg Asp Ile Asp Gln Asp Asn Arg
        115                 120                 125

Ser Thr Ser Pro Ser Ile Tyr Ser Pro Gly Ser Val Glu Asn Asp Ser
    130                 135                 140

Asp Ser Ser Ser Gly Leu Ser Gln Gly Pro Ala Arg Pro Tyr His Pro
145                 150                 155                 160

Pro Pro Leu Phe Pro Pro Ser Pro Gln Pro Pro Asp Ser Thr Pro Arg
                165                 170                 175

Gln Pro Glu Ala Ser Phe Glu Pro His Pro Ser Val Thr Pro Thr Gly
            180                 185                 190

Tyr His Ala Pro Met Glu Pro Pro Thr Ser Arg Met Phe Gln Ala Pro
        195                 200                 205

Pro Gly Ala Pro Pro His Pro Gln Leu Tyr Pro Gly Gly Thr Gly
    210                 215                 220

Gly Val Leu Ser Gly Pro Pro Met Gly Pro Lys Gly Gly Gly Ala Ala
225                 230                 235                 240

Ser Ser Val Gly Gly Pro Asn Gly Gly Lys Gln His Pro Pro Thr
                245                 250                 255

Thr Pro Ile Ser Val Ser Ser Gly Ala Ser Gly Ala Pro Pro Thr
            260                 265                 270

Lys Pro Pro Thr Thr Pro Val Gly Gly Gly Asn Leu Pro Ser Ala Pro
        275                 280                 285

Pro Pro Ala Asn Phe Pro His Val Thr Pro Asn Leu Pro Pro Pro Pro
```

```
                    290                 295                 300
Ala Leu Arg Pro Leu Asn Asn Ala Ser Ala Ser Pro Pro Gly Leu Gly
305                 310                 315                 320

Ala Gln Pro Leu Pro Gly His Leu Pro Ser Pro His Ala Met Gly Gln
            325                 330                 335

Gly Ile Gly Gly Leu Pro Pro Gly Pro Glu Lys Gly Pro Thr Leu Ala
            340                 345                 350

Pro Ser Pro His Ser Leu Pro Pro Ala Ser Ser Ala Pro Ala Pro
        355                 360                 365

Pro Met Arg Phe Pro Tyr Ser Ser Ser Ser Ser Ser Ala Ala Ala
    370                 375                 380

Ser Ser Ser Ser Ser Ser Ser Ser Ser Ala Ser Pro Phe Pro Ala
385                 390                 395                 400

Ser Gln Ala Leu Pro Ser Tyr Pro His Ser Phe Pro Pro Thr Ser
            405                 410                 415

Leu Ser Val Ser Asn Gln Pro Pro Lys Tyr Thr Gln Pro Ser Leu Pro
            420                 425                 430

Ser Gln Ala Val Trp Ser Gln Gly Pro Pro Pro Pro Tyr Gly
        435                 440                 445

Arg Leu Leu Ala Asn Ser Asn Ala His Pro Gly Pro Phe Pro Pro Ser
450                 455                 460

Thr Gly Ala Gln Ser Thr Ala His Pro Pro Val Ser Thr His His
465                 470                 475                 480

His His Gln Gln Gln Gln Gln Gln Gln Gln Gln Gln Gln Gln Gln
            485                 490                 495

His His Gly Asn Ser Gly Pro Pro Pro Gly Ala Phe Pro His Pro
            500                 505                 510

Leu Glu Gly Gly Ser Ser His His Ala His Pro Tyr Ala Met Ser Pro
            515                 520                 525

Ser Leu Gly Ser Leu Arg Pro Tyr Pro Pro Gly Pro Ala His Leu Pro
530                 535                 540

Pro Pro His Ser Gln Val Ser Tyr Ser Gln Ala Gly Pro Asn Gly Pro
545                 550                 555                 560

Pro Val Ser Ser Ser Asn Ser Ser Ser Thr Ser Gln Gly Ser
            565                 570                 575

Tyr Pro Cys Ser His Pro Ser Pro Ser Gln Gly Pro Gln Gly Ala Pro
            580                 585                 590

Tyr Pro Phe Pro Pro Val Pro Thr Val Thr Ser Ser Ala Thr Leu
        595                 600                 605

Ser Thr Val Ile Ala Thr Val Ala Ser Ser Pro Ala Gly Tyr Lys Thr
            610                 615                 620

Ala Ser Pro Pro Gly Pro Pro Tyr Gly Lys Arg Ala Pro Ser Pro
625                 630                 635                 640

Gly Ala Tyr Lys Thr Ala Thr Pro Pro Gly Tyr Lys Pro Gly Ser Pro
            645                 650                 655

Pro Ser Phe Arg Thr Gly Thr Pro Pro Gly Tyr Arg Gly Thr Ser Pro
            660                 665                 670

Pro Ala Gly Pro Gly Thr Phe Lys Pro Gly Ser Pro Thr Val Gly Pro
        675                 680                 685

Gly Pro Leu Pro Pro Ala Gly Pro Ser Gly Leu Pro Ser Leu Pro Pro
        690                 695                 700

Pro Pro Ala Ala Pro Ala Ser Gly Pro Pro Leu Ser Ala Thr Gln Ile
705                 710                 715                 720
```

-continued

Lys Gln Glu Pro Ala Glu Tyr Glu Thr Pro Glu Ser Pro Val Pro
              725                 730                 735

Pro Ala Arg Ser Pro Ser Pro Pro Lys Val Val Asp Val Pro Ser
            740                 745                 750

His Ala Ser Gln Ser Ala Arg Phe Asn Lys His Leu Asp Arg Gly Phe
            755                 760                 765

Asn Ser Cys Ala Arg Ser Asp Leu Tyr Phe Val Pro Leu Glu Gly Ser
    770                 775                 780

Lys Leu Ala Lys Lys Arg Ala Asp Leu Val Glu Lys Val Arg Arg Glu
785             790                 795                 800

Ala Glu Gln Arg Ala Arg Glu Glu Lys Glu Arg Glu Arg Glu Arg Glu
                805                 810                 815

Arg Glu Lys Glu Arg Glu Arg Glu Lys Glu Arg Glu Leu Glu Arg Ser
                820                 825                 830

Val Lys Leu Ala Gln Glu Gly Arg Ala Pro Val Glu Cys Pro Ser Leu
        835                 840                 845

Gly Pro Val Pro His Arg Pro Pro Phe Glu Pro Gly Ser Ala Val Ala
    850                 855                 860

Thr Val Pro Pro Tyr Leu Gly Pro Asp Thr Pro Ala Leu Arg Thr Leu
865             870                 875                 880

Ser Glu Tyr Ala Arg Pro His Val Met Ser Pro Gly Asn Arg Asn His
                885                 890                 895

Pro Phe Tyr Val Pro Leu Gly Ala Val Asp Pro Gly Leu Leu Gly Tyr
                900                 905                 910

Asn Val Pro Ala Leu Tyr Ser Ser Asp Pro Ala Ala Arg Glu Arg Glu
        915                 920                 925

Arg Glu Ala Arg Glu Arg Asp Leu Arg Asp Arg Leu Lys Pro Gly Phe
    930                 935                 940

Glu Val Lys Pro Ser Glu Leu Glu Pro Leu His Gly Val Pro Gly Pro
945             950                 955                 960

Gly Leu Asp Pro Phe Pro Arg His Gly Gly Leu Ala Leu Gln Pro Gly
                965                 970                 975

Pro Pro Gly Leu His Pro Phe Pro Phe His Pro Ser Leu Gly Pro Leu
            980                 985                 990

Glu Arg Glu Arg Leu Ala Leu Ala Ala Gly Pro Ala Leu Arg Pro Asp
        995                 1000                1005

Met Ser Tyr Ala Glu Arg Leu Ala Ala Glu Arg Gln His Ala Glu Arg
    1010                1015                1020

Val Ala Ala Leu Gly Asn Asp Pro Leu Ala Arg Leu Gln Met Leu Asn
1025            1030                1035                1040

Val Thr Pro His His His Gln His Ser His Ile His Ser His Leu His
                1045                1050                1055

Leu His Gln Gln Asp Ala Ile His Ala Ala Ser Ala Ser Val His Pro
            1060                1065                1070

Leu Ile Asp Pro Leu Ala Ser Gly Ser His Leu Thr Arg Ile Pro Tyr
        1075                1080                1085

Pro Ala Gly Thr Leu Pro Asn Pro Leu Leu Pro His Pro Leu His Glu
    1090                1095                1100

Asn Glu Val Leu Arg His Gln Leu Phe Ala Ala Pro Tyr Arg Asp Leu
1105            1110                1115                1120

Pro Ala Ser Leu Ser Ala Pro Met Ser Ala Ala His Gln Leu Gln Ala
            1125                1130                1135

```
Met His Ala Gln Ser Ala Glu Leu Gln Arg Leu Ala Leu Glu Gln Gln
        1140                1145                1150
Gln Trp Leu His Ala His His Pro Leu His Ser Val Pro Leu Pro Ala
    1155                1160                1165
Gln Glu Asp Tyr Tyr Ser His Leu Lys Lys Glu Ser Asp Lys Pro Leu
    1170                1175                1180

<210> SEQ ID NO 19
<211> LENGTH: 1698
<212> TYPE: DNA
<213> ORGANISM: Homo sapiens

<400> SEQUENCE: 19
ggggatagcg atggagacgc cgggcgcatc agcgtcgtcc ttgttgcttc ccgccgcgtc     60
caggcccccg aggaagcgcg aggcgggaga ggctggggct cgacgagca agcagcgggt    120
cctggacgag gaagagtata tcgagggcct ccagacggtc atccaaaggg atttctttcc    180
tgatgtggag aagctccagg cacagaagga gtacctggaa gccgaggaga atggagactt    240
ggaacggatg cgccagattg ccatcaagtt tggctctgcc ttgggcaaga tgtcccggga    300
gcccccgcca ccctatgtga ctccagccac atttgaaacc cctgaggtgc atgcaggcac    360
tggagtggtg ggcaacaagc ccaggccccg cggccgaggc ctggaggatg gagaggctgg    420
agaggaggag gagaaggagc cgctgcccag cctagatgtc ttcctgagcc gctacacgag    480
tgaggacaat gcctccttcc aggagatcat ggaggtggcc aaggagagaa gccgggcacg    540
ccacgcttgg ctctaccagg ctgaggaaga gtttgagaag aggcagaaag ataatctcga    600
actcccgtca gcagagcacc aggccatcga gagcagccag gccagtgtgg agacctggaa    660
gtacaaggcc aagaattccc tcatgtacta tccagagggt gtccctgacg aggagcagct    720
gtttaagaag ccccggcagg tggtacataa gaacacgcgc ttccttaggg accccttcag    780
ccaagccctg agcaggtgcc agctccagca ggcagccgcc ctcaatgccc agcacaaaca    840
gggcaaggtg ggccccgatg caaggagct gatcccccag gagtccccte gagtgggtgg    900
atttggattt gttgccactc cttcccctgc ccctggtgtg aacgagtccc cgatgatgac    960
ctggggggag gttgagaaca cacccttgag agttgaaggg tcggaaacgc cctacgtgga   1020
caggacaccc ggcccagctt ttaagatcct ggagccaggc cgcagggagc ggctgggtct   1080
gaagatggcc aacgaggccg ctgccaagaa ccgggccaag aagcaggaag ccttgcggag   1140
agtgacggag aatctggcca gcctcacccc caaaggcctg agcccagcca tgtcgccagc   1200
cctacagcgc cttgtgagca ggacggccag caagtacaca gaccgggccc tgcgggccag   1260
ctacacacca tccccagcac gctccaccca cctcaagacc ccggccagtg ggctgcagac   1320
ccccacaagc acaccggcgc ctggctctgc cacgcgcacc cctctcacac aggacccggc   1380
ctccatcacg gacaacctgc tgcagctccc tgcccggcgc aaagcttcgg acttcttta   1440
gagccaggcc tgggctgggc tcatagacgc ttcacagagc ctgcagggca gctgtacacc   1500
cagcagagga ctccagcctt ctcggggccc aggcctgggc cagaagctgt tgaccatacc   1560
aggagtcact ggagaaaggg gctgtgctgg ggccagactg gcacaaggca ctcgtgccca   1620
caccacaccc cagggccttg ccaagctgtt tgctgtttaa ttggccccct gaactgtcat   1680
taaagaacac ctaggtac                                                 1698
```